US008889350B2

(12) United States Patent  
Makarov

(10) Patent No.: US 8,889,350 B2  
(45) Date of Patent: Nov. 18, 2014

(54) METHODS AND COMPOSITIONS FOR ISOLATING POLYNUCLEOTIDES

(75) Inventor: Vladimir Makarov, Ann Arbor, MI (US)

(73) Assignee: Swift Biosciences, Inc., Ann Arbor, MI (US)

( * ) Notice: Subject to any disclaimer, the term of this patent is extended or adjusted under 35 U.S.C. 154(b) by 149 days.

(21) Appl. No.: 13/073,781

(22) Filed: Mar. 28, 2011

(65) Prior Publication Data

US 2011/0288284 A1 Nov. 24, 2011

Related U.S. Application Data

(60) Provisional application No. 61/318,038, filed on Mar. 26, 2010.

(51) Int. Cl.
  *C12Q 1/68* (2006.01)
  *C12P 19/34* (2006.01)
  *C07H 21/02* (2006.01)
  *C07H 21/04* (2006.01)
  *C07H 21/00* (2006.01)

(52) U.S. Cl.
  CPC .............. *C12Q 1/683* (2013.01); *C12Q 1/6844* (2013.01); *C12Q 1/6816* (2013.01); *C12Q 1/6862* (2013.01); *C12Q 1/682* (2013.01); *C12Q 1/6876* (2013.01); *C12Q 1/686* (2013.01); *C12Q 1/6846* (2013.01); *C12Q 1/6813* (2013.01)
  USPC ......... 435/6.1; 435/6.11; 435/6.12; 435/91.1; 435/91.2; 536/23.1; 536/24.3; 536/24.33; 536/25.3

(58) Field of Classification Search
  USPC ........... 435/6.1, 6.11, 6.12, 91.1, 91.2, 91.51; 436/94, 501; 536/23.1, 24.3, 24.33, 536/25.3
  See application file for complete search history.

(56) References Cited

U.S. PATENT DOCUMENTS

| | | |
|---|---|---|
| 3,687,808 A | 8/1972 | Merigan et al. |
| 4,469,863 A | 9/1984 | Ts'o et al. |
| 4,476,301 A | 10/1984 | Imbach et al. |
| 4,845,205 A | 7/1989 | Huynh Dinh et al. |
| 4,981,957 A | 1/1991 | Lebleu et al. |
| 5,023,243 A | 6/1991 | Tullis |
| 5,034,506 A | 7/1991 | Summerton et al. |
| 5,118,800 A | 6/1992 | Smith et al. |
| 5,130,302 A | 7/1992 | Spielvogel et al. |
| 5,134,066 A | 7/1992 | Rogers et al. |

(Continued)

FOREIGN PATENT DOCUMENTS

| | | |
|---|---|---|
| EP | 1072679 A2 | 1/2001 |
| WO | WO-97/12896 A1 | 4/1997 |
| WO | WO-98/39352 A1 | 9/1998 |
| WO | WO-99/14226 A2 | 3/1999 |

OTHER PUBLICATIONS

Englisch et al., Chemically Modified Oligonucleotides as Probes and Inhibitors, *Angew. Chem. Int. Ed. Engl.*, 30:613-29 (1991).

(Continued)

*Primary Examiner* — Frank Lu  
(74) *Attorney, Agent, or Firm* — Marshall, Gerstein & Borun LLP

(57) ABSTRACT

Methods of isolating target double-stranded polynucleotides with internal single-stranded regions are provided. Compositions and kits comprising double-stranded polynucleotides with internal single-stranded regions are also provided.

17 Claims, 28 Drawing Sheets

(56) References Cited

U.S. PATENT DOCUMENTS

| | | |
|---|---|---|
| 5,166,315 A | 11/1992 | Summerton et al. |
| 5,175,273 A | 12/1992 | Bischofberger et al. |
| 5,177,196 A | 1/1993 | Meyer, Jr. et al. |
| 5,185,444 A | 2/1993 | Summerton et al. |
| 5,188,897 A | 2/1993 | Suhadolnik et al. |
| 5,194,599 A | 3/1993 | Froehler et al. |
| 5,214,134 A | 5/1993 | Weis et al. |
| 5,216,141 A | 6/1993 | Benner |
| 5,235,033 A | 8/1993 | Summerton et al. |
| 5,264,423 A | 11/1993 | Cohen et al. |
| 5,264,562 A | 11/1993 | Matteucci |
| 5,264,564 A | 11/1993 | Matteucci |
| 5,276,019 A | 1/1994 | Cohen et al. |
| 5,278,302 A | 1/1994 | Caruthers et al. |
| 5,286,717 A | 2/1994 | Cohen et al. |
| 5,319,080 A | 6/1994 | Leumann |
| 5,321,131 A | 6/1994 | Agrawal et al. |
| 5,359,044 A | 10/1994 | Cook et al. |
| 5,367,066 A | 11/1994 | Urdea et al. |
| 5,393,878 A | 2/1995 | Leumann |
| 5,399,676 A | 3/1995 | Froehler |
| 5,405,938 A | 4/1995 | Summerton et al. |
| 5,405,939 A | 4/1995 | Suhadolnik et al. |
| 5,432,272 A | 7/1995 | Benner |
| 5,434,257 A | 7/1995 | Matteucci et al. |
| 5,446,137 A | 8/1995 | Maag et al. |
| 5,453,496 A | 9/1995 | Caruthers et al. |
| 5,455,233 A | 10/1995 | Spielvogel et al. |
| 5,457,187 A | 10/1995 | Gmeiner et al. |
| 5,466,677 A | 11/1995 | Baxter et al. |
| 5,466,786 A | 11/1995 | Buhr et al. |
| 5,470,967 A | 11/1995 | Huie et al. |
| 5,476,925 A | 12/1995 | Letsinger et al. |
| 5,484,908 A | 1/1996 | Froehler et al. |
| 5,489,677 A | 2/1996 | Sanghvi et al. |
| 5,502,177 A | 3/1996 | Matteucci et al. |
| 5,514,785 A | 5/1996 | Van Ness et al. |
| 5,519,126 A | 5/1996 | Hecht |
| 5,519,134 A | 5/1996 | Acevedo et al. |
| 5,525,711 A | 6/1996 | Hawkins et al. |
| 5,527,899 A | 6/1996 | Froehler |
| 5,536,821 A | 7/1996 | Agrawal et al. |
| 5,539,082 A | 7/1996 | Nielsen et al. |
| 5,541,306 A | 7/1996 | Agrawal et al. |
| 5,541,307 A | 7/1996 | Cook et al. |
| 5,550,111 A | 8/1996 | Suhadolnik et al. |
| 5,552,540 A | 9/1996 | Haralambidis |
| 5,561,225 A | 10/1996 | Maddry et al. |
| 5,563,253 A | 10/1996 | Agrawal et al. |
| 5,565,555 A | 10/1996 | Froehler et al. |
| 5,571,799 A | 11/1996 | Tkachuk et al. |
| 5,587,361 A | 12/1996 | Cook et al. |
| 5,587,469 A | 12/1996 | Cook et al. |
| 5,594,121 A | 1/1997 | Froehler et al. |
| 5,596,086 A | 1/1997 | Matteucci et al. |
| 5,596,091 A | 1/1997 | Switzer |
| 5,602,240 A | 2/1997 | De Mesmaeker et al. |
| 5,608,046 A | 3/1997 | Cook et al. |
| 5,610,289 A | 3/1997 | Cook et al. |
| 5,614,617 A | 3/1997 | Cook et al. |
| 5,618,704 A | 4/1997 | Sanghvi et al. |
| 5,623,070 A | 4/1997 | Cook et al. |
| 5,625,050 A | 4/1997 | Beaton et al. |
| 5,633,360 A | 5/1997 | Bischofberger et al. |
| 5,645,985 A | 7/1997 | Froehler et al. |
| 5,646,269 A | 7/1997 | Matteucci et al. |
| 5,663,312 A | 9/1997 | Chaturvedula |
| 5,672,697 A | 9/1997 | Buhr et al. |
| 5,677,437 A | 10/1997 | Teng et al. |
| 5,677,439 A | 10/1997 | Weis et al. |
| 5,681,941 A | 10/1997 | Cook et al. |
| 5,714,331 A | 2/1998 | Buchardt et al. |
| 5,719,262 A | 2/1998 | Buchardt et al. |
| 5,721,218 A | 2/1998 | Froehler |
| 5,750,692 A | 5/1998 | Cook et al. |
| 5,763,588 A | 6/1998 | Matteucci et al. |
| 5,792,608 A | 8/1998 | Swaminathan et al. |
| 5,830,653 A | 11/1998 | Froehler et al. |
| 6,005,096 A | 12/1999 | Matteucci et al. |
| 2004/0143110 A1* | 7/2004 | Krolewski et al. ........... 536/23.2 |
| 2004/0219565 A1 | 11/2004 | Kauppinen et al. |
| 2007/0172919 A1* | 7/2007 | Sarfarazi et al. ............. 435/69.1 |
| 2008/0233572 A1* | 9/2008 | Noble et al. ...................... 435/6 |
| 2009/0227473 A1* | 9/2009 | Crothers ........................ 506/17 |
| 2010/0129879 A1 | 5/2010 | Ach et al. |

OTHER PUBLICATIONS

Freier et al., The ups and downs of nucleic acid duplex stability: structure-stability studies on chemically-modified DNA:RNA duplexes, *Nucleic Acids Res.*, 25:4429-43 (1997).

Martin, A new access to 2'-O-alkylated ribonucleosides and properties of 2'-O-alkylated oligoribonucleotides, *Helv. Chim. Acta*, 78:486-504 (1995).

Nielsen et al., Sequence-selective recognition of DNA by strand displacement with a thymine-substituted polyamide, *Science*, 254:1497-1500 (1991).

* cited by examiner

A.

B.

A.

B.

C.

A.

Gap

B.

A.

B.

A.

B.

A.

B.

A.

B.

A.

B.

A.

B.

A.

B.

A.

B.

A.

B.

C.

A.

B.

|  | Probe 317 | Probe 317 |
|---|---|---|
|  | qPCR Primers 338/339 | qPCR Primers 340/341 |
| pUC19 | 14.55 | 14.03 |
| pUC19 nicked | 15.46 | 14.97 |
| pUC19 UDG | 14.47 | 13.90 |
| pUC19 nicked UDG | 15.25 | 14.54 |
| dNTP UDG | 15.64 | 15.09 |
| dUTP | 14.79 | 14.24 |
| dUTP UDG | 8.58 | 7.71 |
| pUC19 10ng | 8.21 | 7.50 |
| pUC19 1ng | 10.74 | 9.86 |
| pUC19 0.1ng | 13.92 | 13.14 |
| pUC19 0.01ng | 16.08 | 15.29 |
| No Template | 24.22 | 22.60 |

C.

FIGURE 27A
FIGURE 27B
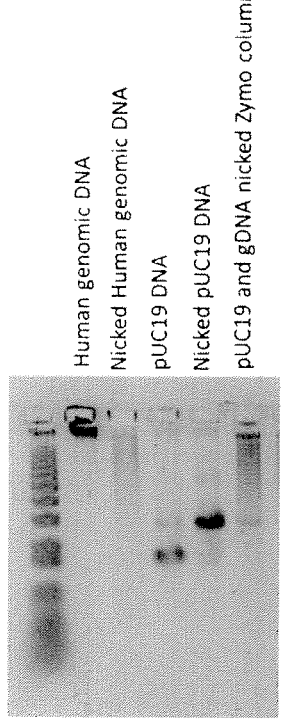
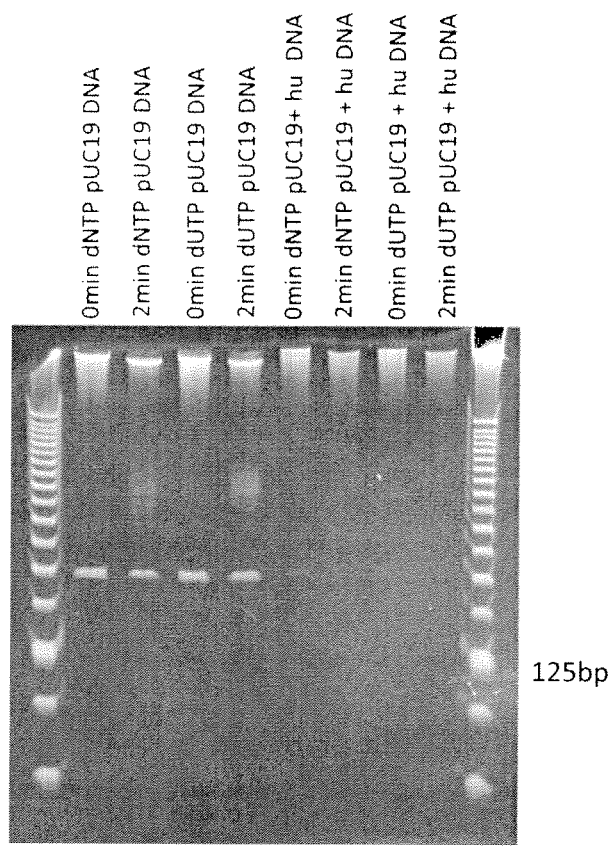

|  | Probe 317 qPCR Primers 338/339 | Probe 317 qPCR Primers 340/341 |
|---|---|---|
| pUC19 | 15.92 | 15.24 |
| pUC19 nicked | 14.50 | 13.98 |
| pUC19 UDG | 16.02 | 15.30 |
| pUC19 nicked UDG | 17.14 | 16.28 |
| pUC19 dT | 16.47 | 15.83 |
| pUC19 dU | 16.22 | 15.57 |
| pUC10 dU UDG | 9.19 | 8.40 |
| human nicked | 23.87 | 19.35 |
| human + pUC19 nicked | 20.36 | 18.56 |
| human + pUC19 dT UDG | 22.38 | 19.10 |
| human + pUC19 dU UDG | 16.56 | 15.97 |
| human + pUC19 dU | 23.03 | 18.96 |
| pUC19 10ng | 7.52 | 6.42 |
| pUC19 1ng | 10.42 | 9.62 |
| pUC19 0.1ng | 14.34 | 13.52 |
| pUC19 0.01ng | 16.82 | 16.07 |
| No Template | 23.74 | 19.05 |

SEQUENCE LISTING

```
<160> NUMBER OF SEQ ID NOS: 5

<210> SEQ ID NO 1
<211> LENGTH: 59
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (59)..(59)
<223> OTHER INFORMATION: 3' biotin

<400> SEQUENCE: 1
ttgctacagg catcgtggtg tcacgctcgt cgtttggtat ggcttcattc agctaaaaa        59

<210> SEQ ID NO 2
<211> LENGTH: 24
<212> TYPE: DNA
<213> ORGANISM: Artificial Sequence
<220> FEATURE:
<223> OTHER INFORMATION: Synthetic primer

<400> SEQUENCE: 2
taccgcacag atgcgtaagg agaa                                               24

<210> SEQ ID NO 3
<211> LENGTH: 24
<212> TYPE: DNA
<213> ORGANISM: Artificial Sequence
<220> FEATURE:
<223> OTHER INFORMATION: Synthetic primer

<400> SEQUENCE: 3
ccaacttaat cgccttgcag caca                                               24

<210> SEQ ID NO 4
<211> LENGTH: 24
<212> TYPE: DNA
<213> ORGANISM: Artificial Sequence
<220> FEATURE:
<223> OTHER INFORMATION: Synthetic primer

<400> SEQUENCE: 4
tgcaagcttg gcgtaatcat ggtc                                               24

<210> SEQ ID NO 5
<211> LENGTH: 24
<212> TYPE: DNA
<213> ORGANISM: Artificial Sequence
<220> FEATURE:
<223> OTHER INFORMATION: Synthetic primer
```

-continued

```
<400> SEQUENCE: 5
taatgcagct ggcacgacag gttt                                              24
```

METHODS AND COMPOSITIONS FOR ISOLATING POLYNUCLEOTIDES

This application claims the priority benefit of U.S. Provisional Patent Application No. 61/318,038 filed Mar. 26, 2010, the disclosure of which is incorporated by reference in its entirety.

This application contains, as a separate part of the disclosure, a Sequence Listing in computer-readable form (filename: 43310A_SeqListing.txt; created: Mar. 28, 2011; 1,254 bytes), which is incorporated by reference in its entirety.

BACKGROUND

Currently available approaches for selectively isolating large DNA fragments involve denaturing a target DNA, hybridizing complementary probes conjugated to biotin followed by isolation of the DNA-probe hybrids using streptavidin-coated beads. Another approach involves cleaving a target DNA with a restriction endonuclease, attaching biotinylated single-stranded DNA probes to the overhangs produced by the restriction endonuclease, and isolating the DNA-probe hybrids using streptavidin-coated beads. However, both of these methods suffer from many shortcomings including expense, inability to isolate large DNA fragments, and non-specific capture of unwanted DNA fragments.

Thus, there exists in the art a need to selectively isolate large DNA fragments without requiring denaturation steps to aid in targeted genomic re-sequencing projects, to improve diagnosis of genetic defects involving chromosomal aberrations, and to add to the available tools of molecular biology.

SUMMARY

In one aspect of the disclosure, there is provided a method of selecting a target double-stranded polynucleotide molecule, said target have an internal destabilized region, wherein the destabilized region comprises (i) an intact polynucleotide strand in the target double-stranded polynucleotide and (ii) a strand substantially complementary to the intact strand and with a plurality of abasic sites or mismatches, said method comprising the steps of: (a) contacting the internal destabilized region with a single-stranded polynucleotide, said single-stranded polynucleotide comprising a linker portion and a capture portion, said linker portion having a sequence sufficiently complementary to hybridize to the intact polynucleotide strand of the destabilized region of the target under appropriate conditions, and said capture portion does not hybridize to the destabilized region of the target; and (b) contacting the target with a capture substance that interacts with the capture portion of the single-stranded polynucleotide to select the target.

In some embodiments, the method further comprises the step of generating the internal destabilized region by nick-translation DNA synthesis and treating with Uracil-DNA glycosylase (UDG).

In yet another aspect of the disclosure, there is provided a method of selecting a target double-stranded polynucleotide molecule, the target having an internal single-stranded region, the method comprising the steps of: (a) contacting the internal single-stranded region with a single-stranded polynucleotide, the single-stranded polynucleotide comprising a linker portion and a capture portion, the linker portion having a sequence sufficiently complementary to hybridize to the single-stranded region of the target under appropriate conditions, and the capture portion does not hybridize to the single-stranded region of the target; and (b) contacting the target with a capture substance that interacts with the capture portion of the single-stranded polynucleotide to select the target, wherein the single stranded polynucleotide is not ligated to the target.

In yet another aspect of the disclosure, there is provided a method of selecting a target double-stranded polynucleotide molecule, said target having an internal single-stranded region, said method comprising the steps of: (a) generating the single-stranded region in the target double-stranded polynucleotide molecule by a process selected from the group consisting of nick-translation DNA synthesis and nick-mediated strand-displacement DNA synthesis, (b) contacting the internal single-stranded region with a single-stranded polynucleotide, said single-stranded polynucleotide comprising a linker portion and a capture portion, said linker portion having a sequence sufficiently complementary to hybridize to the single-stranded region of the target under appropriate conditions, and said capture portion does not hybridize to the single-stranded region of the target; and (c) contacting the target with a capture substance that interacts with the capture portion of the single-stranded polynucleotide to select the target.

In some embodiments of the method, the single-stranded polynucleotide is allele-specific.

In some embodiments of the method, the single-stranded polynucleotide is haplotype-specific.

In one aspect of the method, the internal single-stranded region is a flap.

In another aspect of the method, the internal single-stranded region is a gap.

In another aspect, the method further comprises the step of isolating the target polynucleotide molecule selected in step (b).

In another aspect, the method further comprises the step of extending the capture portion and/or the linker portion of the single-stranded polynucleotide with an additional polynucleotide sequence. In some embodiments, extending the linker portion displaces the strand substantially complementary to the intact strand and with a plurality of abasic sites or mismatches in the destabilized region. In a more specific embodiment, the step of extending the single-stranded polynucleotide adds a specific sequence. In another aspect, the method of extending the single-stranded polynucleotide adds a sequence that interacts with the capture substance. In another aspect, the sequence is added by rolling circle amplification.

In another aspect, the method further comprises the step of cleaving a phosphodiester bond of the target polynucleotide molecule.

In another aspect, the method further comprises the step of generating the single-stranded region in the target double-stranded polynucleotide molecule by cleaving a phosphodiester bond of the target double-stranded polynucleotide molecule and removing one or more bases in a single strand of the target polynucleotide molecule adjacent the phosphodiester bond that was cleaved.

In yet another aspect, the method further comprises the step of generating the single-stranded region in the target double-stranded polynucleotide molecule by a process selected from the group consisting of nick-mediated exonuclease DNA degradation, nick-translation DNA synthesis, and nick-mediated strand-displacement DNA synthesis, after the phosphodiester bond is cleaved.

In another aspect of the method, the target polynucleotide molecule is released from the capture substance. In a more specific embodiment, the target double-stranded polynucleotide molecule is released by enzymatic degradation of the capture substance. In another aspect of the method, the target double-stranded polynucleotide molecule is released by enzymatic degradation of the linker portion. In another aspect of the method, the target double-stranded polynucleotide molecule is released by enzymatic degradation of the capture portion.

In another aspect of the method, the phosphodiester bond is cleaved by a nicking endonuclease. In a more specific embodiment, the nicking endonuclease is selected from the group consisting of Nb.BbvCI, Nb.BsmI, Nb.BsrDI, Nb.BtsI, Nt.AlwI, Nt.BbvCI, Nt.BsmAI, Nt.BspQI, Nt.BstNBI and Nt.CviPII. In another aspect of the method, the nicking endonuclease is inactivated after the phosphodiester bond is cleaved. In some embodiments, the nicking endonuclease is inactivated by heat. In another embodiment, the nicking endonuclease is inactivated by its removal.

In yet another aspect of the method, the capture substance comprises a polynucleotide probe having a sequence sufficiently complementary to hybridize to the capture portion of the single-stranded polynucleotide.

In another aspect of the method, the polynucleotide probe hybridizes to the sequence added to the single-stranded polynucleotide.

In another aspect of the method, the polynucleotide probe is covalently attached to a bead. In a more specific embodiment, the bead is magnetic.

In another aspect of the method, the capture substance comprises (a) a polynucleotide probe having a sequence sufficiently complementary to hybridize to the capture portion of the single-stranded polynucleotide, the probe covalently attached to a first binding partner; and (b) a second binding partner.

In another aspect of the method, the second binding partner is attached to a bead. In a more specific embodiment, the bead is magnetic.

In another aspect of the method, the first binding partner comprises biotin and the second binding partner comprises streptavidin.

In yet another aspect of the method, the capture substance is immobilized on a solid support. In a more specific embodiment, the solid support is selected from the group consisting of a polypropylene tube, a capillary tube, and a glass slide.

Also provided herein is a method of selecting a target double-stranded polynucleotide molecule, the target having an internal single-stranded region, the method comprising the step of contacting the internal single-stranded region with a capture substance that interacts with the internal single-stranded polynucleotide to select the target.

In another aspect of the method, the internal single-stranded region is a flap.

In another aspect, the method further comprises the step of isolating the target polynucleotide molecule.

In another aspect, the method further comprises the step of generating the single-stranded region in the target double-stranded polynucleotide molecule by a process selected from the group consisting of nick-mediated strand-displacement DNA synthesis and rolling circle amplification, after the phosphodiester bond is cleaved.

In another aspect of the method, the target polynucleotide molecule is released from the capture substance. In a more specific embodiment, the target double-stranded polynucleotide molecule is released by enzymatic degradation of the capture portion and capture substance.

In yet another aspect of the method, the phosphodiester bond is cleaved by a nicking endonuclease. In a more specific embodiment, the nicking endonuclease is selected from the group consisting of Nb.BbvCI, Nb.BsmI, Nb.BsrDI, Nb.BtsI, Nt.AlwI, Nt.BbvCI, Nt.BsmAI, Nt.BspQI, Nt.BstNBI and Nt.CviPII. In some embodiments, the nicking endonuclease is inactivated by heat. In another embodiment, the nicking endonuclease is inactivated by its removal.

In another aspect of the method, the capture substance comprises a polynucleotide probe having a sequence sufficiently complementary to hybridize to the internal single-stranded region.

In another aspect of the method, the polynucleotide probe hybridizes to the sequence added to the single stranded polynucleotide. In a more specific embodiment, the polynucleotide probe is covalently attached to a bead. In another aspect, the bead is magnetic.

In another aspect of the method, the capture substance comprises: (a) a polynucleotide probe having a sequence sufficiently complementary to hybridize to the internal single-stranded region, the probe covalently attached to a first binding partner; and (b) a second binding partner.

In another aspect of the method, the second binding partner is attached to a bead. In another aspect, the first binding partner comprises biotin and the second binding partner comprises streptavidin. In another aspect, the bead is magnetic.

In another aspect of the method, the capture substance is immobilized on a solid support. In another aspect, the solid support is selected from the group consisting of a polypropylene tube, a capillary tube, and a glass slide.

Also provided is a composition comprising a substantially double-stranded polynucleotide molecule with an internal destabilized region that is associated with a single-stranded polynucleotide, said destabilized region comprising (i) an intact polynucleotide strand in the target double-stranded polynucleotide and (ii) a strand substantially complementary to the intact strand and with a plurality of abasic sites or mismatches, said single-stranded polynucleotide comprising a linker portion and a capture portion, said linker portion sufficiently complementary to the intact strand of the destabilized region to allow the linker portion and the intact strand to hybridize, and said capture portion not complementary to the substantially double-stranded polynucleotide molecule.

In another aspect, the composition further comprises a polynucleotide probe hybridized to the capture portion of the single-stranded polynucleotide.

In another aspect, the composition further comprises a bead. In a more specific aspect, the bead is magnetic.

In another aspect, the composition further comprises a polynucleotide probe hybridized to the capture portion of the single-stranded polynucleotide. In another aspect of the composition, the polynucleotide probe is covalently attached to the bead.

In another aspect of the composition, the polynucleotide probe is biotinylated.

In another aspect, the composition further comprises a streptavidin-coated bead.

A kit is also provided comprising (a) a single-stranded polynucleotide comprising a linker portion and a capture portion, the linker portion having a sequence sufficiently complementary to hybridize to a single-stranded region of a substantially double-stranded target polynucleotide molecule under appropriate conditions, and the capture portion not complementary to the single-stranded region of the target; (b) a capture substance that interacts with the capture portion of the single-stranded polynucleotide, and (c) a DNA polymerase.

In another aspect, the kit comprises a nicking endonuclease. In a more specific aspect, the nicking endonuclease is selected from the group consisting of Nb.BbvCI, Nb.BsmI, Nb.BsrDI, Nb.BtsI, Nt.AlwI, Nt.BbvCI, Nt.BsmAI, Nt.BspQI, Nt.BstNBI and Nt.CviPII.

In another aspect, the kit comprises an exonuclease. In a more specific aspect, the exonuclease is a 5' exonuclease or a 3' exonuclease.

In another aspect, the kit comprises a DNA polymerase. In a more specific aspect, the DNA polymerase is selected from the group consisting of Pfu DNA polymerase, Vent DNA polymerase, Vent (exo-) DNA polymerase, Deep Vent DNA polymerase, Deep Vent (exo-) DNA polymerase, E. Coli DNA Polymerase I, T7 DNA polymerase, reverse transcriptase, Taq DNA polymerase, DyNAzyme™ Ext DNA polymerase, Sequenase™, Klenow fragment, and Bst polymerase large fragment.

In another aspect, the kit comprises a dNTP mix, the dNTP mix comprising dTTP, dATP, dCTP, and dGTP. In another aspect, the kit comprises a dNTP mix, the dNTP mix comprising dUTP, dATP, dCTP, and dGTP. In another aspect, the kit comprises a dNTP mix, the dNTP mix comprising dTTP, dUTP, dATP, dCTP, and dGTP.

In another aspect, the kit further comprises a uracil-DNA Glycosylase (UDG) enzyme and an abasic endonuclease. In a specific aspect, the abasic endonuclease is selected from the group consisting of APE1, endonuclease III(Nth), endonuclease IV, endonuclease VIII, T4 endonuclease V, Tma endonuclease III, and Tth endonuclease IV.

In another aspect of the kit, the capture substance comprises a polynucleotide probe having a sequence sufficiently complementary to hybridize to the capture portion of the single-stranded polynucleotide. In a more specific aspect, the polynucleotide probe is covalently attached to a bead. In another aspect, the polynucleotide probe is covalently attached to biotin. In yet another aspect, the capture substance further comprises a streptavidin-coated bead. In another aspect, the bead is magnetic.

A method is provided for selecting a target double-stranded polynucleotide molecule, the target having an internal single-stranded region, the method comprising the step of contacting the internal single-stranded region with a capture substance that interacts with the internal single-stranded polynucleotide to select the target.

Other features and advantages of the present disclosure will become apparent from the following detailed description. It should be understood, however, that the detailed description and the specific examples, while indicating preferred embodiments of the disclosure, are given by way of illustration only, because various changes and modifications within the spirit and scope of the disclosure will become apparent to those skilled in the art from this detailed description.

BRIEF DESCRIPTION OF THE DRAWINGS

FIG. 27A is an agarose gel of nicked pUC19 (Target DNA) and human genomic DNA and mixtures thereof. FIG. 27B displays the results of a nick-translation reaction incorporating uracil into a target polynucleotide (pUC19) in the presence of human genomic DNA.

DETAILED DESCRIPTION

Figure 1:
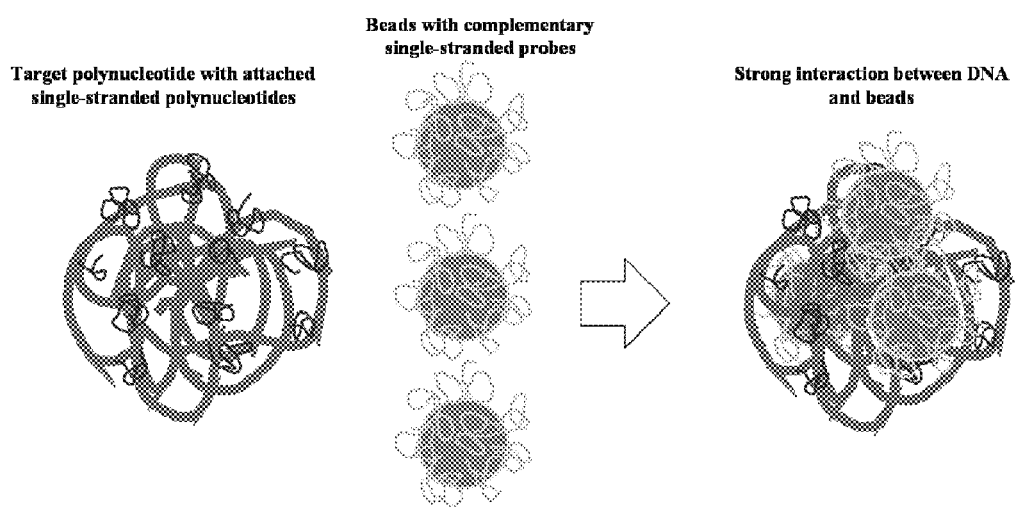
FIG. 1 is an illustration of a target double-stranded polynucleotide molecule with internal single-stranded regions attached to single-stranded polynucleotides. In the presence of beads with complementary single-stranded probes attached, the beads and the target polynucleotide interact.
Figure 2:
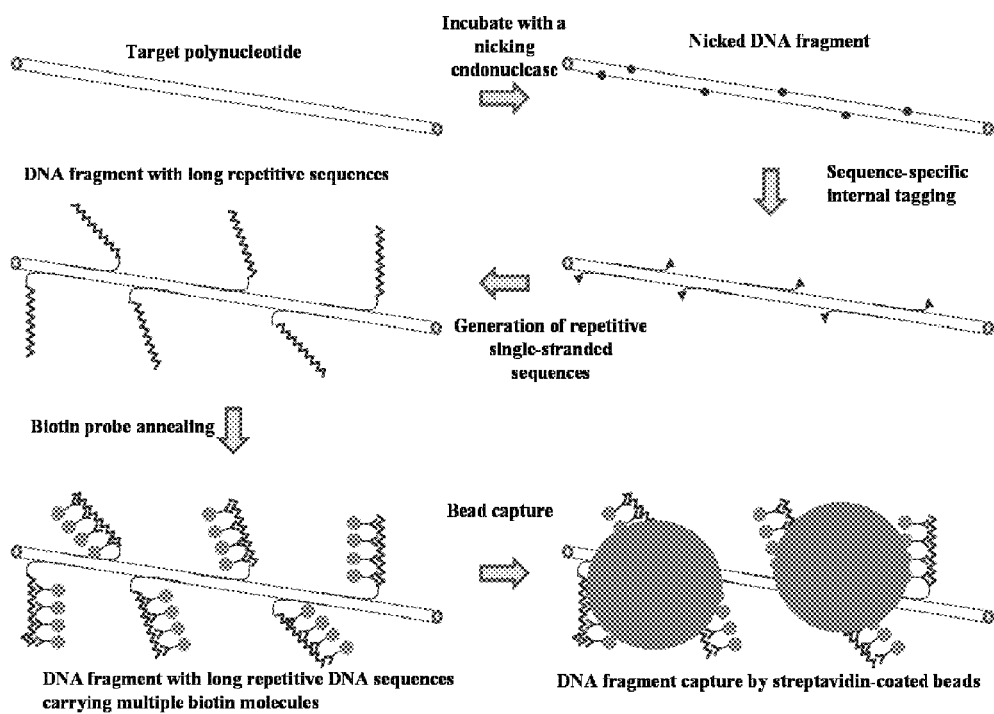
FIG. 2 is a schematic of one aspect of the claimed methods wherein the capture substance comprises single-stranded probes attached to biotin and streptavidin-coated beads.
Figure 3:
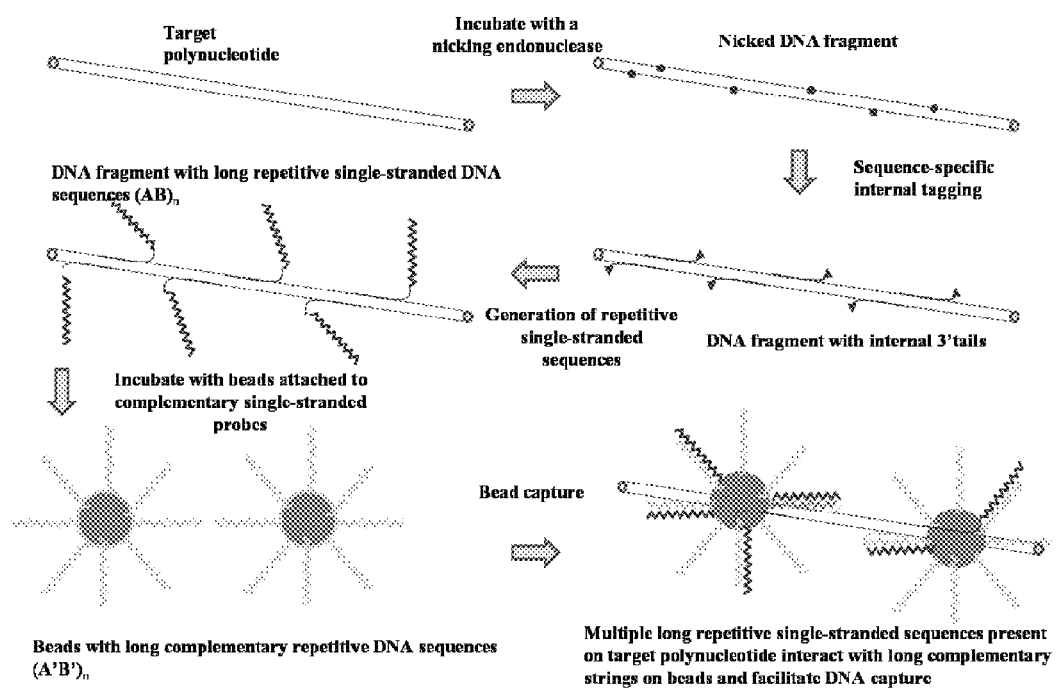
FIG. 3 is a schematic a second aspect of the claimed methods wherein the capture substance comprises single-stranded probes attached to beads.
Figure 4:
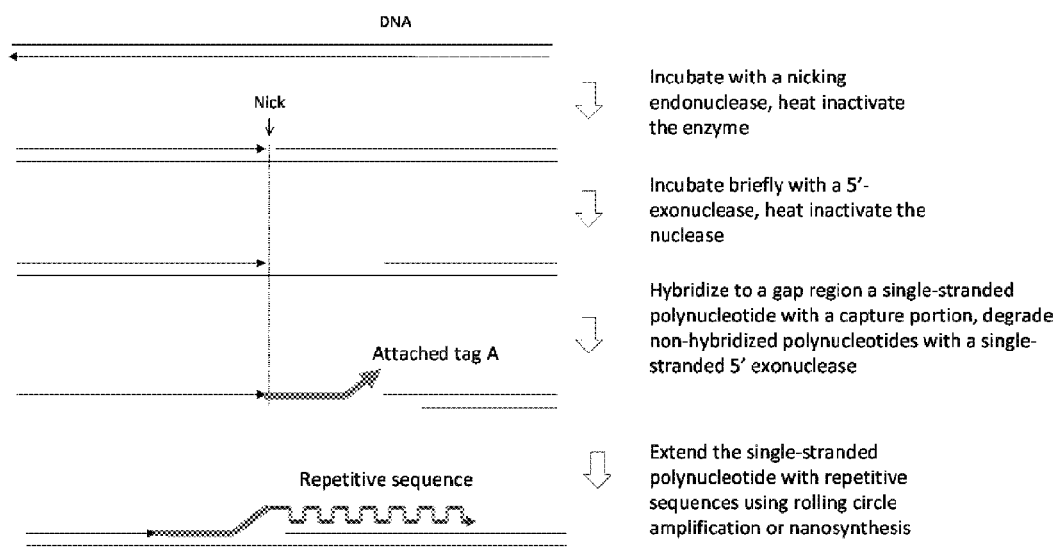
FIG. 4 is a schematic of single-stranded region generation in the target polynucleotide utilizing limited nick-mediated 5' exonuclease treatment.
Figure 5:
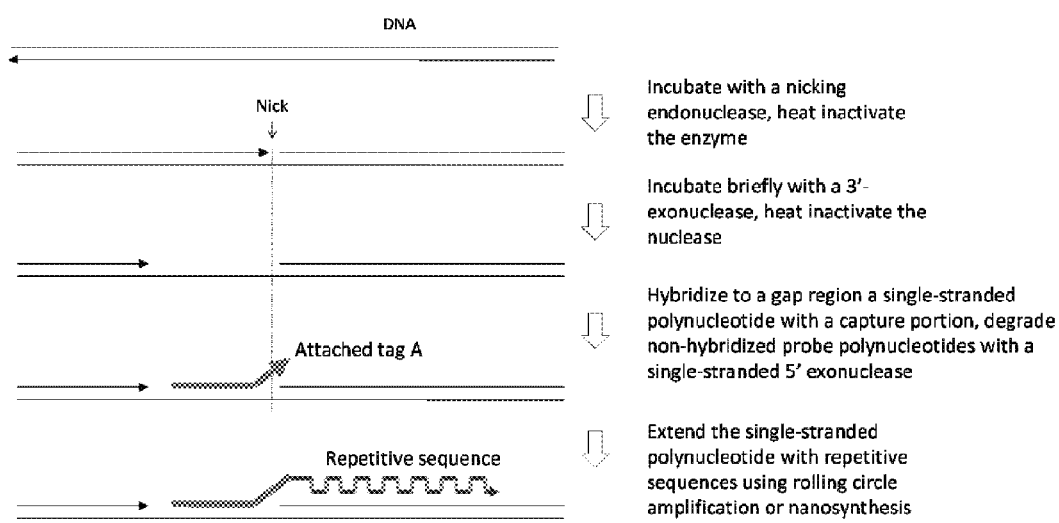
FIG. 5 is a schematic of single-stranded region generation in the target polynucleotide utilizing limited nick-mediated 3' exonuclease treatment.
Figure 6:
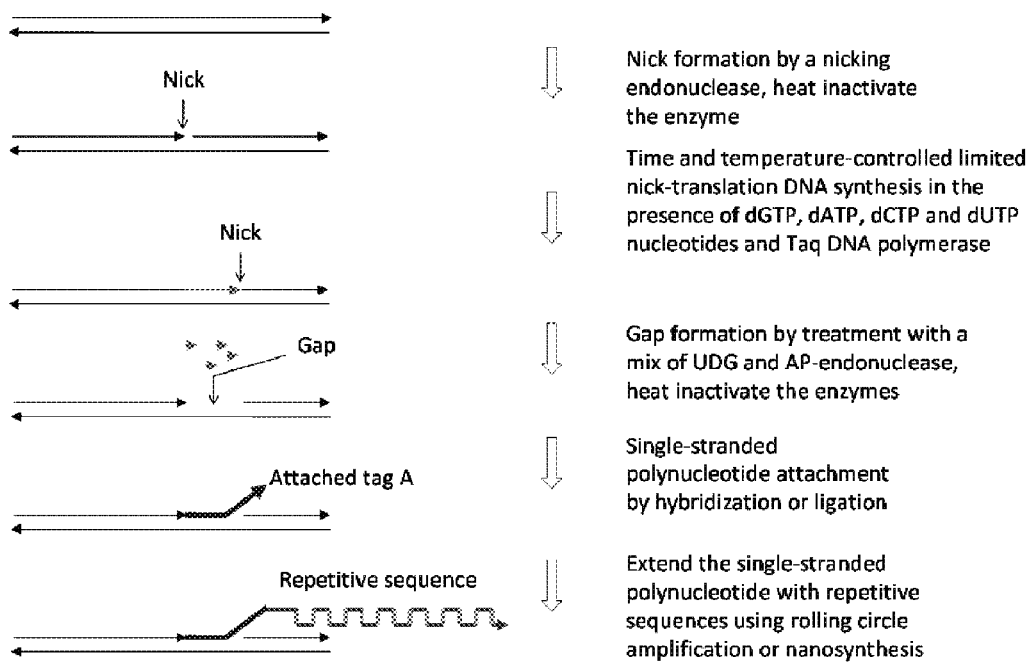
FIG. 6 is a schematic of single-stranded region generation in the target polynucleotide utilizing limited DNA nick-translation synthesis.
Figure 7:
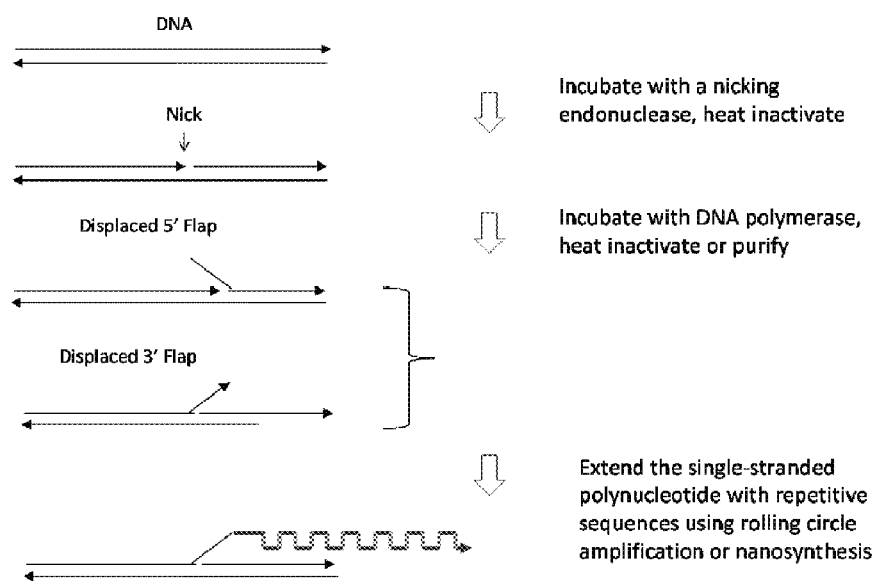
FIG. 7 is a schematic of single-stranded region generation in the target polynucleotide utilizing limited strand-displacement DNA synthesis.

Provided herein is a method of selecting a target double-stranded polynucleotide molecule by internally tagging the target with single-stranded polynucleotides and capturing the target with a substance that interacts with the single-stranded polynucleotide. The method is useful in various aspects to allow the capture of large, double-stranded polynucleotides for use in molecular biology, re-sequencing projects, and diagnosis of genetic abnormalities involving chromosomal aberrations.

I. Definitions

A "target double-stranded polynucleotide molecule" is defined as any double-stranded polynucleotide including without limitation, a synthetic polynucleotide, a naturally-occurring polynucleotide, a chimeric polynucleotide that is a combination of a naturally-occurring polynucleotide and a synthetic polynucleotide, double stranded-RNA, chromosomal DNA, plasmid DNA, viral DNA, mitochondrial DNA, phage DNA, bacterial DNA, or fragment thereof, sought to be selected by the practitioner of the disclosed methods. The target double-stranded polynucleotide molecule is, in various aspects, about 100, about 120, about 140, about 160, about 180, about 200, about 250, about 300, about 350, about 400, about 450, about 500, about 600, about 700, about 800, about 900, about 1000, about 1100, about , about 1200, about 1300, about 1400, about 1500, about 1600, about 1700, about 1800, about 1900, about 2000, about 2500, about 3000, about 3500, about 4000, about 4500, about 5000, about 6000, about 7000, about 8000, about 9000, about 10,000, about 15,000, about 20,000, about 30,000, about 40,000, about 50,000, about 60,000, about 70,000, about 80,000, about 90,000, about 100,000, about 150,000, about 200,000, about 250,000, about 300,000, about 350,000, about 400,000, about 450,000, about 500,000, about 750,000, about 1,000,000, about 1,250,000, about 1,500,000, about 1,750,000, about 2,000,000, about 2,500,000, about 3,000,000, about 4,000,000, about 5,000,000, about 6,000,000, about 7,000,000, about 8,000,000, about 9,000,000, about 10,000,000 or more bases in length. It will be understood that the term "about" as used herein means "approximately."

A "nicking endonuclease" is understood in the art to mean an enzyme that recognizes a double stranded polynucleotide and cleaves only one phosphodiester bond on one strand of the double stranded polynucleotide.

As used herein, the term "capture substance" includes any molecule, compound, or mixture that interacts with a target polynucleotide molecule.

"Polymerase" is understood in the art to mean an enzyme or other catalyst capable of catalyzing a reaction leading to a target-sequence-dependent incorporation of a nucleotide at a 3'-end of a polynucleotide when the polynucleotide is annealed a complementary polynucleotide. Exemplary polymerases include but are not limited to Pfu DNA polymerase, Vent DNA polymerase, Vent (exo-) DNA polymerase, Deep Vent DNA polymerase, Deep Vent (exo-) DNA polymerase, *E. coli* polymerase I, T7 DNA polymerase, reverse transcriptase, Taq DNA polymerase, DyNAzyme™ Ext DNA polymerase, Sequenase™ Klenow fragment, and Bst polymerase large fragment.

Methods for polynucleotide hybridization and washing are well known in the art and can be found in standard references in molecular biology such as those cited herein. In general, hybridizations are usually carried out in solutions of high ionic strength (6×SSC or 6×SSPE) at a temperature 20° C. to 25° C. below the melting temperature ($T_m$). High stringency wash conditions are often determined empirically in preliminary experiments, but usually involve a combination of salt and temperature that is approximately 12° C. to 20° C. below the $T_m$. One example of high stringency wash conditions is 1×SSC at 60° C. Another example of high stringency wash conditions is 0.1×SSPE, 0.1% SDS at 42° C. (Meinkoth and Wahl, *Anal. Biochem.*, 138:267-284, 1984). An example of even higher stringency wash conditions is 0.1×SSPE, 0.1% SDS at 50° C. to 65° C. In another non-limiting example, high stringency washing is carried out under conditions of 1×SSC and 60° C. As is well recognized in the art, various combinations of factors can result in conditions of substantially equivalent stringency. Such equivalent conditions are within the scope of the present disclosure.

By the terms "interact" or "associate", it is meant herein that two substances or compounds (e.g., primer and template; chemical moiety and nucleotide) are bound (e.g., attached, hybridized, joined, annealed, or covalently linked) to one another sufficiently that the intended assay can be conducted. By the terms "specific" or "specifically," it is meant herein that two components bind selectively to each other compared to other compounds. The parameters required to achieve specific interactions are determined routinely, e.g., using conventional methods in the art.

A "flap" is defined as a polynucleotide that protrudes from a substantially double-stranded polynucleotide. A flap will result from strand displacement during DNA synthesis by a DNA polymerase without 5' to 3' exonuclease activity. The flap is complementary to the sequence immediately 3' of the protrusion (or immediately 5' in the case of a 5' flap) and will engage in strand exchange with the strand of the same sequence (as pictured in FIG. 8A). According to the various embodiments of the disclosure, the flap is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, about 65, about 70, about 75, about 80, about 85, about 90, about 95, about 100, about 110, about 120, about 130, about 140, about 150, about 160, about 170, about 180, about 190, about 200 or more bases in length.

Figure 8:
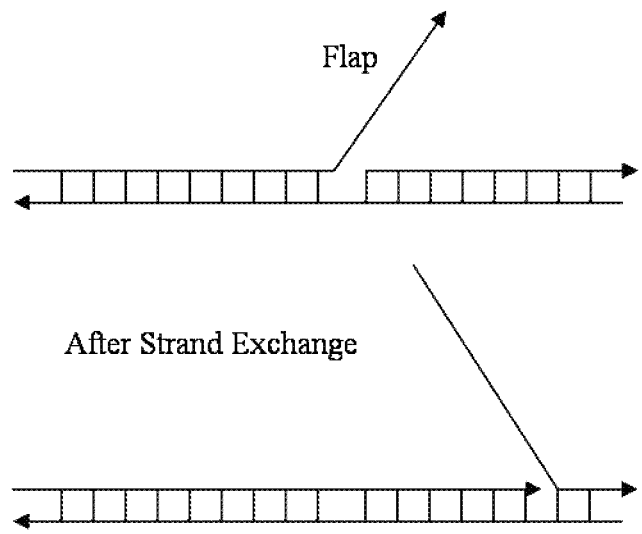
FIG. 8 is a schematic of (A) a target double-stranded polynucleotide with a "flap" structure (both before and after strand exchange) and (B) a target double-stranded polynucleotide with a "gap."
Figure 8:
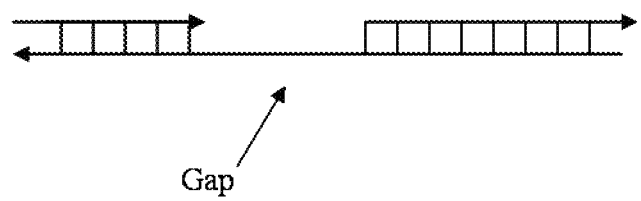

A "gap" is defined as a region of a substantially double-stranded polynucleotide lacking one or more consecutive bases on one strand (illustrated in FIG. 8B). According to the various embodiments of the disclosure, the gap is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, about 65, about 70, about 75, about 80, about 85, about 90, about 95, about 100, about 110, about 120, about 130, about 140, about 150, about 160, about 170, about 180, about 190, about 200 or more bases in length.

A "linker portion" is defined as a segment of a single-stranded polynucleotide used in the methods of the disclosure having a sequence that is sufficiently complementary to interact with a target polynucleotide (illustrated below) under appropriate conditions. According to the various embodiments of the disclosure, the linker portion is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, about 65, about 70, about 75, about 80, about 85, about 90, about 95, about 100, about 110, about 120, about 130, about 140, about 150 or more bases in length.

A "capture portion" is defined as the segment of a single-stranded polynucleotide used in the methods of the disclosure that interacts with a capture substance, generally by hybridizing with a complementary polynucleotide sequence present in the capture substance (illustrated below). According to the various embodiments of the disclosure, the capture portion is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, about 65, about 70, about 75, about 80, about 85, about 90, about 95, about 100, about 110, about 120, about 130, about 140, about 150, about 160, about 170, about 180, about 190, about 200, about 250, about 300, about 400, about 500, about 750, about 1000, about 1500, about 2000, about 3000, about 4000, about 5000, about 7500, about 10,000, about 20,000, about 30,000, about 40,000, about 50,000, about 75,000, about 100,000 or more bases in length.

Figure 9:
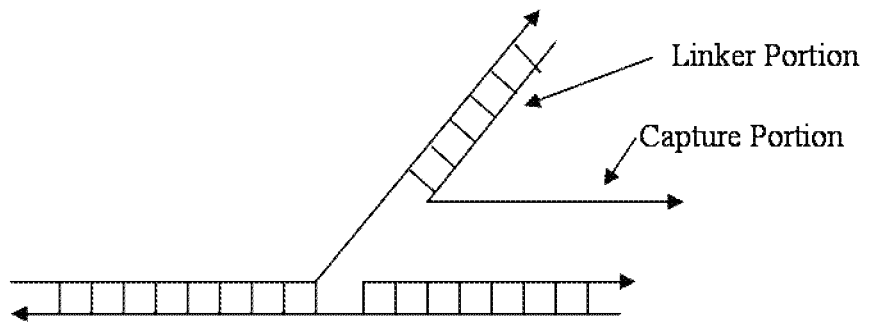
FIG. 9A is a schematic of a single-stranded polynucleotide comprising a linker portion (shown hybridizing to a flap on the target polynucleotide) and a capture portion.
FIG. 9B is a schematic of a single-stranded polynucleotide comprising a linker portion (shown hybridizing to a gap on the target polynucleotide) and a capture portion.
FIG. 9C is a schematic of a single-stranded polynucleotide comprising a linker portion (shown hybridizing to a gap on the target polynucleotide) and a capture portion (shown hybridizing to a complementary sequence attached to a capture substance).
Figure 9:
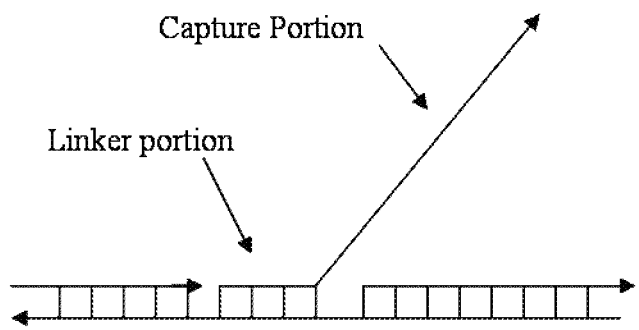
Figure 9:
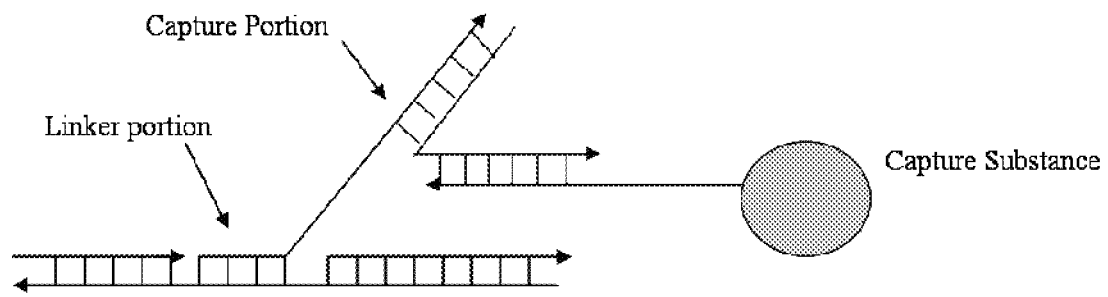

In one aspect, a single-stranded polynucleotide comprising a linker portion (shown hybridizing to a flap on the target) and a capture portion is shown in FIG. 9A.

In another aspect, a single-stranded polynucleotide comprising a linker portion (shown hybridizing to a gap on the target) and a capture portion is shown in FIG. 9B.

In another aspect, a single-stranded polynucleotide comprising a linker portion (shown hybridizing to a gap on the target) and a capture portion (shown hybridizing to a complementary sequence attached to a capture substance) is shown in FIG. 9C.

A "bead" of the disclosure comprises virtually any insoluble or solid material. For example, and without limitation, the bead is comprised of silica gel, glass (e.g. controlled-pore glass (CPG)), nylon, Wang resin, Merrifield resin, Sephadex/Sepharose, cellulose, magnetic beads, a metal surface (e.g. steel, gold, silver, aluminum, silicon and copper), a plastic material (e.g., polyethylene, polypropylene, polyamide, polyester, polyvinylidenedifluoride (PVDF)) and the like. Beads can be swellable, e.g., polymeric beads such as Wang resin, or non-swellable, e.g., CPG).

A "solid support" is defined as a material having a rigid or semi-rigid surface. Such materials will preferably take the form of plates or slides, pellets, disks, capillary tubes or other convenient forms, although other forms may be used. In some embodiments, at least one surface of the solid support will be substantially flat. The solid support in various aspects is biological, non-biological, organic, inorganic, or a combination of any of these, existing as particles, strands, precipitates, gels, sheets, tubing, spheres, containers, capillaries, pads, slices, films, plates, slides, etc. The solid support is thus, in one aspect, flat but in other aspects, the support has alternative surface configurations. For example, in certain aspects, the solid support has raised or depressed regions on which reactions including, but not limited to, hybridization, ligation, and cleavage take place. In some embodiments, the solid support is chosen to provide appropriate light-absorbing characteristics. For example, the support in some aspects is a polymerized Langmuir Blodgett film, functionalized glass, Si, Ge, GaAs, GaP, $SiO_2$, $SiN_4$, modified silicon, or any one of a variety of gels or polymers such as (poly)tetrafluoroethylene, (poly)vinyliden-difluoride, polystyrene, polycarbonate, or combinations thereof. Other suitable solid support materials will be readily apparent to those of skill in the art. In certain aspects, the surface of the solid support includes reactive groups, which in various aspects are carboxyl, amino, hydroxyl, or thiol. In other aspects, the surface is optically transparent and in another aspect, the surface has Si—H functionalities, such as are found on silica surfaces. The solid support comprises, in various aspects, an array of ordered sets of dsDNA and/or ssDNA fragments that are covalently or non-covalently attached to the solid support. In this way the target polynucleotide molecule is captured on the surface of the solid support via hybridization with the attached DNA.

An "allele" refers to one or more forms of a gene at a given locus on a chromosome (i.e., alternative sequences of the same gene). As used herein, "allele-specific" refers to the ability of a polynucleotide sequence (e.g., the single-stranded polynucleotide) to distinguish (i.e., hybridize with) one allele from an alternative allele.

As used herein, "haplotype" is a combination of alleles at different loci on the chromosome that are typically transmitted (i.e., inherited) together. As used herein, "haplotype-specific" refers to the ability of a polynucleotide sequence (e.g., the single-stranded polynucleotide) to distinguish (i.e., hybridize with) one haplotype from an alternative haplotype.

A "single-nucleotide polymorphism" or "SNP" is a DNA sequence variation occurring when a single nucleotide in the genome differs between members of a biological species or paired chromosomes in an individual.

A "destabilized region" refers to a portion of the target double-stranded polynucleotide that exhibits reduced affinity between the two complementary strands as compared to identical strands with perfect complementarity. In some embodiments, a region is destabilized because a plurality of sites in the region are abasic. In some embodiments, a region is destabilized because a plurality of sites comprise non-complementary bases. In some embodiments, the destabilized region is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, about 65, about 70, about 75, about 80, about 85, about 90, about 95, about 100, about 120, about 140, about 160, about 180, about 200, about 250, about 300, about 350, about 400, about 450, about 500, about 600, about 700, about 800, about 900, about 1000, about 1100, about , about 1200, about 1300, about 1400, about 1500, about 1600, about 1700, about 1800, about 1900, about 2000 or more bases in length. A destabilized region is substantially double-stranded and comprises an intact polynucleotide strand and a strand substantially complementary to the intact strand and with a plurality of abasic sites or mismatches. The reduced stability of the strand-strand interaction, compared to the same intact polynucleotide hybridized to a strand having 100% complementarity, allows for invasion of the single-stranded polynucleotide, which will bind more strongly due to full complementarity.

It must be noted that as used herein and in the appended claims, the singular forms "a," "and," and "the" include plural referents unless the context clearly dictates otherwise. Thus, for example, reference to "an internal single-stranded region" includes a plurality of such regions.

II. Polynucleotides and Modified Polynucleotides

As used herein, the term "polynucleotide" as a target molecule, is used interchangeably with the term oligonucleotide. "Polynucleotide" refers to a plurality of individual nucleotides linked together in a single molecule. The term "nucleotide" or its plural as used herein is interchangeable with modified forms as discussed herein and otherwise known in the art. In certain instances, the art uses the term "nucleobase" which embraces naturally-occurring nucleotides as well as modifications of nucleotides that can be polymerized.

Methods of making polynucleotides having a predetermined sequence are well-known in the art. See, e.g., Sambrook et al., Molecular Cloning: A Laboratory Manual (2nd ed. 1989) and F. Eckstein (ed.) Oligonucleotides and Analogues, 1st Ed. (Oxford University Press, New York, 1991).

In various aspects, methods provided include use of polynucleotides which are DNA, modified DNA, RNA, modified RNA or combinations of the two types. Modified forms of polynucleotides are also contemplated for methods and compositions of the invention which include those having at least one modified internucleotide linkage. Modified polynucleotides or oligonucleotides are described in detail herein below.

Specific examples of modified polynucleotides include those containing modified backbones or non-natural internucleoside linkages. Polynucleotides having modified backbones include those that retain a phosphorus atom in the backbone and those that do not have a phosphorus atom in the backbone. Modified polynucleotides that do not have a phosphorus atom in their internucleoside backbone are considered to be within the meaning of "polynucleotides."

Modified polynucleotides backbones containing a phosphorus atom include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Also contemplated are polynucleotides having inverted polarity comprising a single 3' to 3' linkage at the 3'-most internucleotide linkage, i.e. a single inverted nucleoside residue which may be abasic (the nucleotide is missing or has a hydroxyl group in place thereof). Salts, mixed salts and free acid forms are also contemplated. Representative United States patents that teach the preparation of the above phosphorus-containing linkages include, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, the disclosures of which are incorporated by reference herein.

Modified polynucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages; siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and CH2 component parts. See, for example, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, the disclosures of which are incorporated herein by reference in their entireties.

In still other embodiments, polynucleotide mimetics wherein both one or more sugar and/or one or more internucleotide linkage of the nucleotide units are replaced with "non-naturally occurring" groups. In one aspect, this embodiment contemplates a peptide nucleic acid (PNA). In PNA compounds, the sugar-backbone of an oligonucleotide is replaced with an amide containing backbone. See, for example U.S. Pat. Nos. 5,539,082; 5,714,331; and 5,719,262, and Nielsen et al., 1991, Science, 254: 1497-1500, the disclosures of which are herein incorporated by reference.

In still other embodiments, polynucleotides are provided with phosphorothioate backbones and oligonucleosides with heteroatom backbones, and including —CH2-NH—O—CH2, —CH2-N(CH3)-O—CH2-, —CH2-O—N(CH3)-CH2-, —CH2-N(CH3)-N(CH3)-CH2- and —O—N(CH3)-

CH2-CH2- described in U.S. Pat. Nos. 5,489,677, and 5,602,240. Also contemplated are polynucleotides with morpholino backbone structures described in U.S. Pat. No. 5,034,506.

In various forms, the linkage between two successive monomers in the oligo consists of 2 to 4, desirably 3, groups/atoms selected from —CH2, —O—, —S—, —NRH—, >C=O, >C=NRH, >C=S, —Si(R")2-, —SO—, —S(O)2-, —P(O)2-, —PO(BH3)-, —P(O,S)—, —P(S)2-, —PO(R")—, —PO(OCH3)-, and —PO(NHRH)—, where RH is selected from hydrogen and C1-4-alkyl, and R" is selected from C1-6-alkyl and phenyl. Illustrative examples of such linkages are —CH2-CH2-CH2-, —CH2-CO—CH2-, —CH2-CHOH—CH2-, —O—CH2-O—, —O—CH2-CH2-, —O—-CH2-CH=(including R5 when used as a linkage to a succeeding monomer), —CH2-CH2-O—, —NRH—CH2-CH2-, —CH2-CH2-NRH—, —CH2-NRH—CH2-, —O—CH2-CH2-NRH—, —NRH—OC—O—, —NRH—CO—NRH—, —NRH—CS—NRH—, —NRH—C(=NRH)—NRH—, —NRH—CO—CH2-NRH—O—CO—O—, —O—CO—CH2-O—, —O—CH2-CO—O—, —CH2-CO—NRH—, —O—CO—NRH—, —NRH—CO—CH2-, —O—CH2-CO—NRH—, —O—CH2-CH2-NRH—, —CH=N—O—, —CH2-NRH—O—, —CH2-O—N=(including R5 when used as a linkage to a succeeding monomer), —CH2-O—NRH—, —CO—NRH—CH2-, —CH2-NRH—O—, —CH2-NRH—CO—, —O—NRH—CH2-, —O—NRH, —O—CH2-S—, —S—CH2-O—, —CH2-CH2-S—, —O—CH2-CH2-S—, —S—CH2-CH= (including R5 when used as a linkage to a succeeding monomer), —S—CH2-CH2-, —S—CH2-CH2-O—, —S—CH2-CH2-S—, —CH2-S—CH2-, —CH2-SO—CH2-, —CH2-SO2-CH2-, —O—SO—O—, —O—S(O)2-O—, —O—S(O)2-CH2-, —O—S(O)2-NRH—, —NRH—S(O)2-CH2-; —O—S(O)2-CH2-, —O—P(O)2-O—, —O—P(O,S)—O—, —O—P(S)2-O—, —S—P(O)2-O—, —S—P(O,S)—O—, —S—P(S)2-O—, —O—P(O)2-S—, —O—P(O,S)—S—, —O—P(S)2-S—, —S—P(O)2-S—, —S—P(O,S)—S—, —S—P(S)2-S—, —O—PO(R")—O—, —O—PO(OCH3)—O—, —O—PO(OCH2CH3)-O—, —O—PO(OCH2CH2S—R)—O—, —O—PO(BH3)-O—, —O—PO(NHRN)—O—, —O—P(O)2-NRHH—, —NRH—P(O)2-O—, —O—P(O,NRH)—O—, —CH2-P(O)2-O—, —O—P(O)2-CH2-, and —O—Si(R")2-O—; among which —CH2-CO—NRH—, —CH2-NRH—O—, —S—CH2-O—, —O—P(O)2-O—, —O—P(—O,S)—O—, —O—P(S)2-O—, —NRHP(O)2-O—, —O—P(O,NRH)—O—, —O—PO(R")—O—, —O—PO(CH3)-O—, and —O—PO(NHRN)—O—, where RH is selected form hydrogen and C1-4-alkyl, and R" is selected from C1-6-alkyl and phenyl, are contemplated. Further illustrative examples are given in Mesmaeker et. al., 1995, Current Opinion in Structural Biology, 5: 343-355 and Susan M. Freier and Karl-Heinz Altmann, 1997, Nucleic Acids Research, vol 25: pp 4429-4443.

Still other modified forms of polynucleotides are described in detail in U.S. patent application NO. 20040219565, the disclosure of which is incorporated by reference herein in its entirety.

Modified polynucleotides also optionally contain one or more substituted sugar moieties. In certain aspects, oligonucleotides comprise one of the following at the 2' position: OH; F; O—, S—, or N-alkyl; O—, S—, or N-alkenyl; O—, S—or N-alkynyl; or O-alkyl-O-alkyl, wherein the alkyl, alkenyl and alkynyl may be substituted or unsubstituted C1 to C10 alkyl or C2 to C10 alkenyl and alkynyl. Other embodiments include O[(CH2)nO]mCH3, O(CH2)nOCH3, O(CH2)nNH2, O(CH2)nCH3, O(CH2)nONH2, and O(CH2)nON[(CH2)nCH3]2, where n and m are from 1 to about 10. Other oligonucleotides comprise one of the following at the 2' position: C1 to C10 lower alkyl, substituted lower alkyl, alkenyl, alkynyl, alkaryl, aralkyl, O-alkaryl or O-aralkyl, SH, SCH3, OCN, Cl, Br, CN, CF3, OCF3, SOCH3, SO2CH3, ONO2, NO2, N3, NH2, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. In one aspect, a modification includes 2'-methoxyethoxy (2'-O—CH2CH2OCH3, also known as 2'-O-(2-methoxyethyl) or 2'-MOE) (Martin et al., 1995, Helv. Chim. Acta, 78: 486-504) i.e., an alkoxyalkoxy group. Other modifications include 2'-dimethylaminooxyethoxy, i.e., a O(CH2)2ON(CH3)2 group, also known as 2'-DMAOE, as described in examples herein below, and 2'-dimethylaminoethoxyethoxy (also known in the art as 2'-O-dimethyl-amino-ethoxy-ethyl or 2'-DMAEOE), i.e., 2'-O—CH2-O—CH2-N(CH3)2, also described in examples herein below.

Still other modifications include 2'-methoxy (2'-O—CH3), 2'-aminopropoxy (2'-OCH2CH2CH2NH2), 2'-allyl (2'-CH2-CH=CH2), 2'-O-allyl (2'-O—CH2-CH=CH2) and 2'-fluoro (2'-F). The 2'-modification may be in the arabino (up) position or ribo (down) position. In one aspect, a 2'-arabino modification is 2'-F. Similar modifications may also be made at other positions on the oligonucleotide, for example, at the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. See, for example, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, the disclosures of which are incorporated by reference in their entireties herein.

In one aspect, a modification of the sugar includes Locked Nucleic Acids (LNAs) in which the 2'-hydroxyl group is linked to the 3' or 4' carbon atom of the sugar ring, thereby forming a bicyclic sugar moiety. The linkage is in certain aspects is a methylene (—CH2-)n group bridging the 2' oxygen atom and the 4' carbon atom wherein n is 1 or 2. LNAs and preparation thereof are described in WO 98/39352 and WO 99/14226.

Polynucleotides also include base modifications or substitutions. As used herein, "unmodified" or "natural" bases include the purine bases adenine (A) and guanine (G), and the pyrimidine bases thymine (T), cytosine (C) and uracil (U). Modified bases include other synthetic and natural bases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified bases include tricyclic pyrimidines such as phenoxazine cytidine(1H-pyrimido[5,4-b][1,4]benzoxazin-2(3H)- one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido [5,4-b][1,4]benzox-azin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified bases may also include those in which the purine or pyrimidine base is replaced with other heterocycles, for example 7-deazaadenine, 7-deazaguanosine, 2-aminopyridine and 2-pyridone. Further bases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., 1991, Angewandte Chemie, International Edition, 30: 613, and those disclosed by Sanghvi, Y. S., Chapter 15, Antisense Research and Applications, pages 289-302, Crooke, S. T. and Lebleu, B., ed., CRC Press, 1993. Certain of these bases are useful for increasing the binding affinity and include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. and are, in certain aspects combined with 2'-O-methoxyethyl sugar modifications. See, U.S. Pat. Nos. 3,687,808; 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,830,653; 5,763,588; 6,005,096; 5,750,692 and 5,681,941, the disclosures of which are incorporated herein by reference.

A "modified base" or other similar term refers to a composition which can pair with a natural base (e.g., adenine, guanine, cytosine, uracil, and/or thymine) and/or can pair with a non-naturally occurring base. In certain aspects, the modified base provides a Tm differential of 15, 12, 10, 8, 6, 4, or 2° C. or less. Exemplary modified bases are described in EP 1 072 679 and WO 97/12896.

By "nucleobase" is meant the naturally occurring nucleobases adenine (A), guanine (G), cytosine (C), thymine (T) and uracil (U) as well as non-naturally occurring nucleobases such as xanthine, diaminopurine, 8-oxo-N6-methyladenine, 7-deazaxanthine, 7-deazaguanine, N4,N4-ethanocytosin, N',N'-ethano-2,6-diaminopurine, 5-methylcytosine (mC), 5-(C3-C6)-alkynyl-cytosine, 5-fluorouracil, 5-bromouracil, pseudoisocytosine, 2-hydroxy-5-methyl-4-tr-iazolopyridin, isocytosine, isoguanine, inosine and the "non-naturally occurring" nucleobases described in Benner et al., U.S. Pat. No. 5,432,272 and Susan M. Freier and Karl-Heinz Altmann, 1997, Nucleic Acids Research, vol. 25: pp 4429-4443. The term "nucleobase" thus includes not only the known purine and pyrimidine heterocycles, but also heterocyclic analogues and tautomers thereof. Further naturally and non-naturally occurring nucleobases include those disclosed in U.S. Pat. No. 3,687,808 (Merigan, et al.), in Chapter 15 by Sanghvi, in Antisense Research and Application, Ed. S. T. Crooke and B. Lebleu, CRC Press, 1993, in Englisch et al., 1991, Angewandte Chemie, International Edition, 30: 613-722 (see especially pages 622 and 623, and in the Concise Encyclopedia of Polymer Science and Engineering, J. I. Kroschwitz Ed., John Wiley & Sons, 1990, pages 858-859, Cook, Anti-Cancer Drug Design 1991, 6, 585-607, each of which are hereby incorporated by reference in their entirety). The term "nucleosidic base" or "base unit" is further intended to include compounds such as heterocyclic compounds that can serve like nucleobases including certain "universal bases" that are not nucleosidic bases in the most classical sense but serve as nucleosidic bases. Especially mentioned as universal bases are 3-nitropyrrole, optionally substituted indoles (e.g., 5-nitroindole), and optionally substituted hypoxanthine. Other desirable universal bases include, pyrrole, diazole or triazole derivatives, including those universal bases known in the art.

III. Target Molecules, Cells, Proteins, and Structures

A worker of ordinary skill in the art will readily appreciate that any target, including for example and without limitation, a molecule, whole cell, protein, or organelle, to which a single-stranded polynucleotide can be attached can be selected according to the methods of the disclosure.

In various aspects, a target molecule for use with the methods of the invention is a single stranded polynucleotide. In another aspect, the target molecule is a substantially double-stranded polynucleotide molecule that has internal single-single stranded regions with free 3' ends. By "substantially double-stranded" it is meant that greater than about 75%, greater than about 80%, greater than about 85%, greater than about 90%, greater than about 95%, greater than about 98%, or greater than about 99% of the target polynucleotide is double stranded. In another aspect, the target substantially double-stranded polynucleotide molecule is about 100, about 120, about 140, about 160, about 180, about 200, about 250, about 300, about 350, about 400, about 450, about 500, about 600, about 700, about 800, about 900, about 1000, about 1100, about , about 1200, about 1300, about 1400, about 1500, about 1600, about 1700, about 1800, about 1900, about 2000, about 2500, about 3000, about 3500, about 4000, about 4500, about 5000, about 6000, about 7000, about 8000, about 9000, about 10,000, about 15,000, about 20,000, about 30,000, about 40,000, about 50,000, about 60,000, about 70,000, about 80,000, about 90,000, about 100,000, about 150,000, about 200,000, about 250,000, about 300,000, about 350,000, about 400,000, about 450,000, about 500,000, about 750,000, about 1,000,000, about 1,250,000, about 1,500,000, about 1,750,000, about 2,000,000, about 2,500,000, about 3,000,000, about 4,000,000, about 5,000,000, about 6,000,000, about 7,000,000, about 8,000,000, about 9,000,000, about 10,000,000 or more bases in length.

In one aspect, the single-stranded region is a gap. Without intending to limit the scope of the disclosure, a substantially double-stranded molecule with an internal single-stranded gap has the structure illustrated in FIG. 10A. In some embodiments, the internal single-stranded region is located at a terminus of the substantially double-stranded molecule, wherein the single-stranded region extends into an internal region of the double-stranded molecule.

Figure 10:
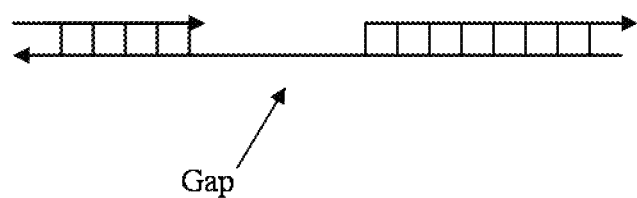
FIG. 10A is a schematic of a substantially double-stranded target polynucleotide with an internal single-stranded gap.
FIG. 10B is a schematic of the target molecule of 10A with an attached single-stranded polynucleotide, wherein the single-stranded polynucleotide comprises a linker portion and a capture portion.
Figure 10:
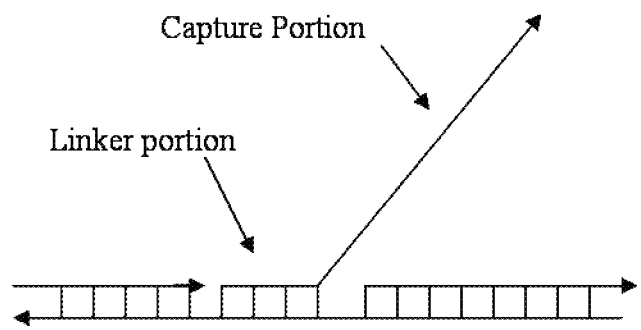

Without intending to limit the scope of the disclosure, the target molecule with an attached single-stranded polynucleotide, wherein the single-stranded polynucleotide comprises a linker portion and a capture portion, can comprise the structure illustrated in FIG. 10B.

In various aspects, the 3' single strand terminus of the target molecule is 100% complementary to the linker portion of the single-stranded polynucleotide of the method, or alternatively, the 3' single-stranded terminus of the target molecule is less than 100% complementary to the linker portion of the single-stranded polynucleotide of the method.

Figure 11:
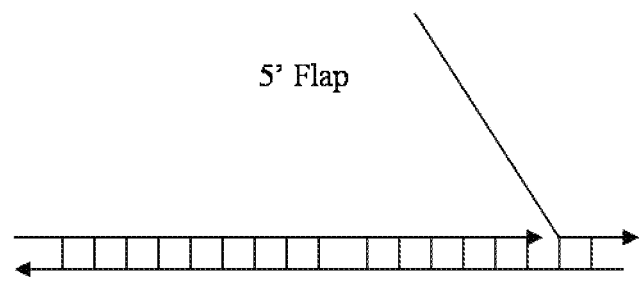
FIG. 11 is a schematic of a target molecule that is a substantially double-stranded molecule that has an internal single-stranded flap, (A) before and (B) after strand exchange.
Figure 11:
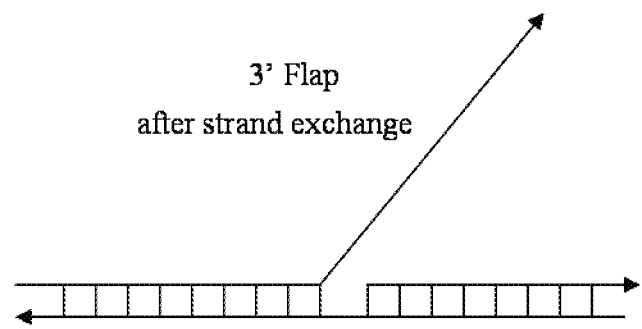

In various aspects, the target molecule is a substantially double-stranded molecule that has internal single-stranded flaps. Without intending to limit the scope of the disclosure, a substantially double-stranded molecule with an internal single-stranded flap can comprise the structure illustrated in FIG. 11A or 11B.

In either embodiment, the internal single-stranded region of the target molecule is sufficiently complementary to a linker portion of a single-stranded polynucleotide to allow for hybridization to the linker portion sequence (described below).

As will be understood by those of skill in the art, a substantially double-stranded target molecule can be denatured into complementary single-stranded DNA molecules according to known methods. The methods and compositions for isolating large double-stranded target polynucleotides disclosed herein are also useful for isolating large single-stranded target molecules IV. Generating the Single-stranded Region of the Target Polynucleotide In some aspects of the disclosure, a target polynucleotide molecule has at least one region that is single stranded. In instances wherein the target polynucleotide molecule is double stranded, the single stranded region may be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, about 65, about 70, about 75, about 80, about 85, about 90, about 95, about 100 or more bases in length.

In some aspects of the disclosure, a phosphodiester bond is cleaved on one strand of the target polynucleotide molecule. In specific aspects, the phosphodiester bond is cleaved by a nicking endonuclease. Exemplary commercially available nicking endonucleases include, but are not limited to, Nb.BbvCI, Nb.BsmI, Nb.BsrDI, Nb.BtsI, Nt.AlwI, Nt.BbvCI, Nt.BsmAI, Nt.BspQI, Nt.BstNBI and Nt.CviPII.

Figure 12:
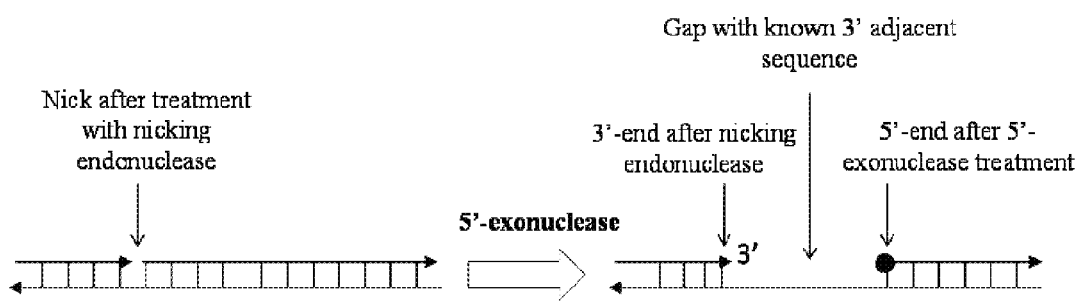
FIG. 12 is a schematic of a single-stranded region in a target polynucleotide generated by nick-mediated exonuclease DNA degradation with (A) a 5'-exonuclease or (B) a 3'-exonuclease.
Figure 12:
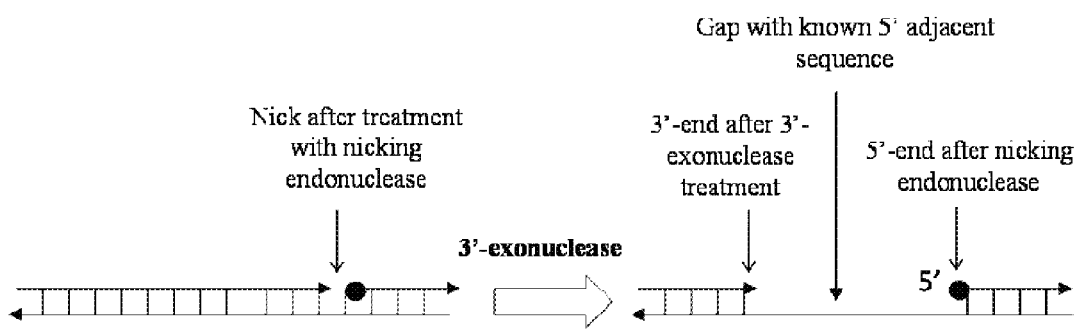

In various embodiments of the disclosure, a single-stranded region is generated on the target polynucleotide molecule by nick-mediated exonuclease DNA degradation, nick-translation DNA synthesis, or nick-mediated strand-displacement DNA synthesis. In one aspect, the single-stranded region is generated by nick-mediated exonuclease DNA degradation (illustrated in FIG. 12). Briefly, after a phosphodiester bond is cleaved by a nicking endonuclease, the target polynucleotide molecule is incubated with an exonuclease for 1 second, 2 seconds, 3 seconds, 4 seconds, 5 seconds, 6 seconds, 7 seconds, 8 seconds, 9 seconds, 10 seconds, 11 seconds, 12 seconds, 13 seconds, 14 seconds, 15 seconds, 16 seconds, 17 seconds, 18 seconds, 19 seconds, 20 seconds, 21 seconds, 22 seconds, 23 seconds, 24 seconds, 25 seconds, 26 seconds, 27 seconds, 28 seconds, 29 seconds, 30 seconds, 31 seconds, 32 seconds, 33 seconds, 34 seconds, 35 seconds, 36 seconds, 37 seconds, 38 seconds, 39 seconds, 40 seconds, 41 seconds, 42 seconds, 43 seconds, 44 seconds, 45 seconds, 46 seconds, 47 seconds, 48 seconds, 49 seconds, 50 seconds, 51 seconds, 52 seconds, 53 seconds, 54 seconds, 55 seconds, 56 seconds, 57 seconds, 58 seconds, 59 seconds, 60 seconds, about 1 minute 5 seconds, about 1 minute 5 seconds, about 1 minute 5 seconds, about 1 minute 10 seconds, about 1 minute 15 seconds, about 1 minute 20 seconds, about 1 minute 25 seconds, about 1 minute 30 seconds, about 1 minute 35 seconds, about 1 minute 40 seconds, about 1 minute 45 seconds, about 1 minute 50 seconds, about 1 minute 55 seconds, about 2 minutes, about 2 minutes 10 seconds, about 2 minutes 20 seconds, about 2 minutes 30 seconds, about 2 minutes 40 seconds, about 2 minutes 50 seconds, about 3 minutes, about 3 minutes 15 seconds, about 3 minutes 30 seconds, about 3 minutes 45 seconds, about 4 minutes, about 4 minutes 30 seconds, about 4 minutes 45 seconds, about 5 minutes, about 5 minutes 15 seconds, about 5 minutes 30 seconds, about 5 minutes 45 seconds, about 6 minutes, about 6 minutes 15 seconds, about 6 minutes 30 seconds, about 6 minutes 45 seconds, about 7 minutes, about 7 minutes 15 seconds, about 7 minutes 30 seconds, about 7 minutes 45 seconds, about 8 minutes, about 8 minutes 15 seconds, about 8 minutes 30 seconds, about 8 minutes 45 seconds, about 9 minutes, about 9 minutes 15 seconds, about 9 minutes 30 seconds, about 9 minutes 45 seconds, about 10 minutes or more. In one aspect, the exonuclease is a 3' exonuclease. In another aspect, the exonuclease is a 5' exonuclease. In some aspects, the exonuclease is heat inactivated to stop exonuclease activity. The single-stranded region generated by the exonuclease may be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, about 65, about 70, about 75, about 80, about 85, about 90, about 95, about 100 or more bases in length. As will be understood by one of skill in the art, the desired length of the single stranded region can be regulated by varying the amount of time the target polynucleotide is exposed to the exonuclease.

In one aspect, the single-stranded region is generated by nick-translation DNA synthesis. Briefly, after a phosphodiester bond is cleaved by a nicking endonuclease, the target polynucleotide molecule is incubated with dGTP, dATP, dCTP, and dUTP nucleotides and a DNA polymerase with 5' to 3' exonuclease activity (e.g. Taq polymerase) for 1 second, 2 seconds, 3 seconds, 4 seconds, 5 seconds, 6 seconds, 7 seconds, 8 seconds, 9 seconds, 10 seconds, 11 seconds, 12 seconds, 13 seconds, 14 seconds, 15 seconds, 16 seconds, 17 seconds, 18 seconds, 19 seconds, 20 seconds, 21 seconds, 22 seconds, 23 seconds, 24 seconds, 25 seconds, 26 seconds, 27 seconds, 28 seconds, 29 seconds, 30 seconds, 31 seconds, 32 seconds, 33 seconds, 34 seconds, 35 seconds, 36 seconds, 37 seconds, 38 seconds, 39 seconds, 40 seconds, 41 seconds, 42 seconds, 43 seconds, 44 seconds, 45 seconds, 46 seconds, 47 seconds, 48 seconds, 49 seconds, 50 seconds, 51 seconds, 52 seconds, 53 seconds, 54 seconds, 55 seconds, 56 seconds, 57 seconds, 58 seconds, 59 seconds, 60 seconds, about 1 minute 5 seconds, about 1 minute 5 seconds, about 1 minute 5 seconds, about 1 minute 10 seconds, about 1 minute 15 seconds, about 1 minute 20 seconds, about 1 minute 25 seconds, about 1 minute 30 seconds, about 1 minute 35 seconds, about 1 minute 40 seconds, about 1 minute 45 seconds, about 1 minute 50 seconds, about 1 minute 55 seconds, about 2 minutes, about 2 minutes 10 seconds, about 2 minutes 20 seconds, about 2 minutes 30 seconds, about 2 minutes 40 seconds, about 2 minutes 50 seconds, about 3 minutes, about 3 minutes 15 seconds, about 3 minutes 30 seconds, about 3 minutes 45 seconds, about 4 minutes, about 4 minutes 30 seconds, about 4 minutes 45 seconds, about 5 minutes, about 5 minutes 15 seconds, about 5 minutes 30 seconds, about 5 minutes 45 seconds, about 6 minutes, about 6 minutes 15 seconds, about 6 minutes 30 seconds, about 6 minutes 45 seconds, about 7 minutes, about 7 minutes 15 seconds, about 7 minutes 30 seconds, about 7 minutes 45 seconds, about 8 minutes, about 8 minutes 15 seconds, about 8 minutes 30 seconds, about 8 minutes 45 seconds, about 9 minutes, about 9 minutes 15 seconds, about 9 minutes 30 seconds, about 9 minutes 45 seconds, about 10 minutes or more. Next, in some embodiments, the single-stranded gap is generated by incubating the target polynucleotide with a Uracil-DNA glycosylase (UDG) and an Apurinic/Apyrimidinic endonuclease (AP endonuclease). UDG catalyzes the release of free uracil from uracil-containing DNA while AP endonuclease catalyzes a nick in the phosphodiester backbone of the sites at which UDG removed the uracil bases, thereby generating a single stranded gap in the region of new DNA synthesis. In various embodiments, the single stranded region generated by nick-translation DNA synthesis is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, about 65, about 70, about 75, about 80, about 85, about 90, about 95, about 100, about 110, about 120, about 130, about 140, about 150, about 160, about 170, about 180, about 190, about 200 or more bases in length. In some embodiments, after incubation with the DNA polymerase, the target polynucleotide is incubated with the same nicking endonuclease from the first step. After incubation with UDG and AP endonuclease, a 3' end with a known sequence is thereby generated. As will be understood by one of skill in the art, the desired length of the single stranded region can be regulated by varying the amount of time the target polynucleotide is exposed to the DNA polymerase and dGTP, dATP, dCTP, dUTP mixture.

Figure 13:
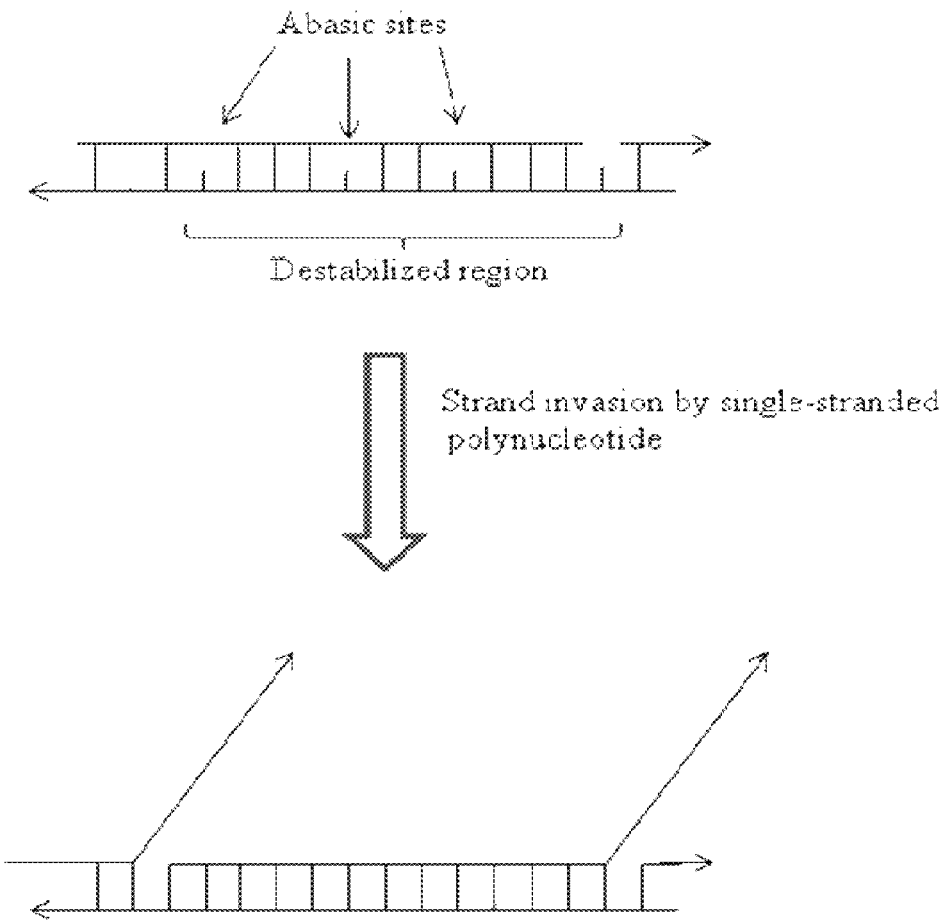
FIG. 13A is a schematic of an internal destabilized region of a target polynucleotide generated by nick-translation DNA synthesis and Uracil-DNA glycosylase (UDG) treatment. The Figure also depicts strand invasion by the single-stranded polynucleotide.
FIG. 13B depicts an internal destabilized region at the terminus of a target polynucleotide.
Figure 13:
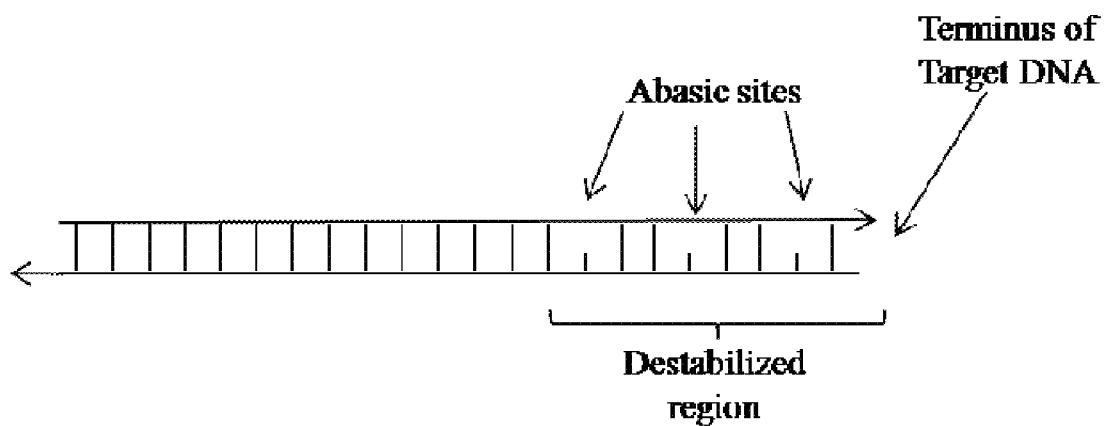

In an alternative embodiment, nick-translation DNA synthesis is used to generate an internal destabilized region, wherein the destabilized region comprises an intact polynucleotide strand and a strand substantially complementary to the intact strand and with a plurality of abasic sites or mismatches. In this embodiment, a phosphodiester bond is cleaved by a nicking endonuclease, the target polynucleotide molecule is incubated with dGTP, dATP, dCTP, and dUTP nucleotides and a DNA polymerase with 5' to 3' exonuclease activity. In some embodiments, the internal destabilized region is generated by incubating the target polynucleotide with a Uracil-DNA glycosylase (UDG). Treating the nick-translated DNA with UDG results in abasic sites on one strand of the target polynucleotide, thereby generating a destabilized region due to reduced base-pairing at the sites lacking uracil bases (depicted in FIG. 13). The reduced stability of the strand-strand interaction allows for invasion of the single-stranded polynucleotide, which will bind more strongly due to full complementarity (depicted in FIG. 13A).

In an alternative embodiment, after a phosphodiester bond is cleaved by a nicking endonuclease, the target polynucleotide molecule is incubated with dGTP, dATP, dCTP, and dTTP nucleotides and a DNA polymerase with 5' to 3' exonuclease activity (e.g. Taq polymerase) for 1 second, 2 seconds, 3 seconds, 4 seconds, 5 seconds, 6 seconds, 7 seconds, 8 seconds, 9 seconds, 10 seconds, 11 seconds, 12 seconds, 13 seconds, 14 seconds, 15 seconds, 16 seconds, 17 seconds, 18 seconds, 19 seconds, 20 seconds, 21 seconds, 22 seconds, 23 seconds, 24 seconds, 25 seconds, 26 seconds, 27 seconds, 28 seconds, 29 seconds, 30 seconds, 31 seconds, 32 seconds, 33 seconds, 34 seconds, 35 seconds, 36 seconds, 37 seconds, 38 seconds, 39 seconds, 40 seconds, 41 seconds, 42 seconds, 43 seconds, 44 seconds, 45 seconds, 46 seconds, 47 seconds, 48 seconds, 49 seconds, 50 seconds, 51 seconds, 52 seconds, 53 seconds, 54 seconds, 55 seconds, 56 seconds, 57 seconds, 58 seconds, 59 seconds, 60 seconds, or more, at which time the polymerase reaction is spiked with dUTP at a concentration of between 0.3 mM-2 mM. The result is incorporation of uracil bases in the polymerization product at a region downstream from the nick site. Thus, subsequent treatment of the nick-translated product with UDG or UDG/AP as described above will result in a destabilized region or a single-stranded region, respectively, downstream of the nick site, as compared to immediate incorporation of uracil bases.

In another embodiment, the destabilized region is created by first cleaving a phosphodiester bond of a target double-stranded polynucleotide with a nicking endonuclease. Next, the target polynucleotide molecule is incubated with a DNA polymerase with 5' to 3' exonuclease activity and a mixture of dNTPs, wherein at least one of the four dNTPs is present in a limited amount, such that the DNA polymerase incorporates a plurality of mismatches, thereby resulting in a destabilized region.

In another embodiment, the internal destabilized region is located at a terminus of the substantially double-stranded molecule (depicted in FIG. 13B). The location of the internal destabilized region is also "internal" because the region necessarily extends into the internal region of the double-stranded molecule.

In one aspect, the single-stranded region is generated by nick-mediated strand-displacement DNA synthesis Briefly, after a phosphodiester bond is cleaved by a nicking endonuclease, the target polynucleotide molecule is incubated with a DNA polymerase lacking 5' to 3' exonuclease activity but possessing strand-displacing activity (e.g. Klenow fragment, Bst polymerase large fragment, Vent DNA polymerase, Vent (exo-) DNA polymerase, Deep Vent DNA polymerase, Deep Vent (exo-) DNA polymerase, DyNAzyme™ Ext DNA polymerase, Sequenase™, etc.) and dGTP, dATP, dCTP, and dTTP for 1 second, 2 seconds, 3 seconds, 4 seconds, 5 seconds, 6 seconds, 7 seconds, 8 seconds, 9 seconds, 10 seconds, 11 seconds, 12 seconds, 13 seconds, 14 seconds, 15 seconds, 16 seconds, 17 seconds, 18 seconds, 19 seconds, 20 seconds, 21 seconds, 22 seconds, 23 seconds, 24 seconds, 25 seconds, 26 seconds, 27 seconds, 28 seconds, 29 seconds, 30 seconds, 31 seconds, 32 seconds, 33 seconds, 34 seconds, 35 seconds, 36 seconds, 37 seconds, 38 seconds, 39 seconds, 40 seconds, 41 seconds, 42 seconds, 43 seconds, 44 seconds, 45 seconds, 46 seconds, 47 seconds, 48 seconds, 49 seconds, 50 seconds, 51 seconds, 52 seconds, 53 seconds, 54 seconds, 55 seconds, 56 seconds, 57 seconds, 58 seconds, 59 seconds, 60 seconds, about 1 minute 5 seconds, about 1 minute 5 seconds, about 1 minute 5 seconds, about 1 minute 10 seconds, about 1 minute 15 seconds, about 1 minute 20 seconds, about 1 minute 25 seconds, about 1 minute 30 seconds, about 1 minute 35 seconds, about 1 minute 40 seconds, about 1 minute 45 seconds, about 1 minute 50 seconds, about 1 minute 55 seconds, about 2 minutes, about 2 minutes 10 seconds, about 2 minutes 20 seconds, about 2 minutes 30 seconds, about 2 minutes 40 seconds, about 2 minutes 50 seconds, about 3 minutes, about 3 minutes 15 seconds, about 3 minutes 30 seconds, about 3 minutes 45 seconds, about 4 minutes, about 4 minutes 30 seconds, about 4 minutes 45 seconds, about 5 minutes, about 5 minutes 15 seconds, about 5 minutes 30 seconds, about 5 minutes 45 seconds, about 6 minutes, about 6 minutes 15 seconds, about 6 minutes 30 seconds, about 6 minutes 45 seconds, about 7 minutes, about 7 minutes 15 seconds, about 7 minutes 30 seconds, about 7 minutes 45 seconds, about 8 minutes, about 8 minutes 15 seconds, about 8 minutes 30 seconds, about 8 minutes 45 seconds, about 9 minutes, about 9 minutes 15 seconds, about 9 minutes 30 seconds, about 9 minutes 45 seconds, about 10 minutes or more. Strand exchange will periodically expose a single-stranded region with a 3' end. In various embodiments, the single-stranded region generated by using this method is 1, 2, 3, 4, 5, 6, 7, 8, 9, 10, 11, 12, 13, 14 , 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, about 65, about 70, about 75, about 80, about 85, about 90, about 95, about 100, about 110, about 120, about 130, about 140, about 150, about 160, about 170, about 180, about 190, about 200 or more bases in length. As will be understood by one of skill in the art, the desired length of the single stranded region can be regulated by varying the amount of time the target polynucleotide is exposed to the DNA polymerase and dGTP, dATP, dCTP, dUTP mixture as well as varying the temperature at which the reaction takes place.

According to some embodiments, an alternative version of the nick-mediated strand-displacement DNA synthesis step is envisioned. First, a phosphodiester bond on one strand of the double stranded target molecule is cleaved by a nicking endonuclease. Next, the target polynucleotide molecule is incubated with a DNA polymerase lacking 5' to 3' exonuclease activity and a mixture of dGTP, dCTP, and dTTP. Next, the target polynucleotide is incubated with the polymerase and a mixture of dCTP, dTTP, and dATP. Next, the target polynucleotide is incubated with the polymerase and a mixture of dGTP, dTTP, and dATP. Finally, the target polynucleotide is incubated with the polymerase and a mixture of dCTP, dGTP, and dATP. A person of skill in the art will recognize that the steps utilizing the four different dNTP mixtures can be performed in any order. Analysis of 20 arbitrarily selected lambda DNA sites demonstrated that the four-step polymerization scheme just described would result in 10 extension products in the range of 19-37 bases, 2 extension products between 15 and 17 bases, and 8 extension products between 6 and 12 bases. Thus, it is expected that at least 50% of phosphodiester bond cleavages created by nicking endonucleases followed by strand-displacement DNA synthesis as just described will result in internal 3' DNA tails of more than 20 bases.

V. Allele- or SNP-Specific Haplotype Capture

Figure 14:
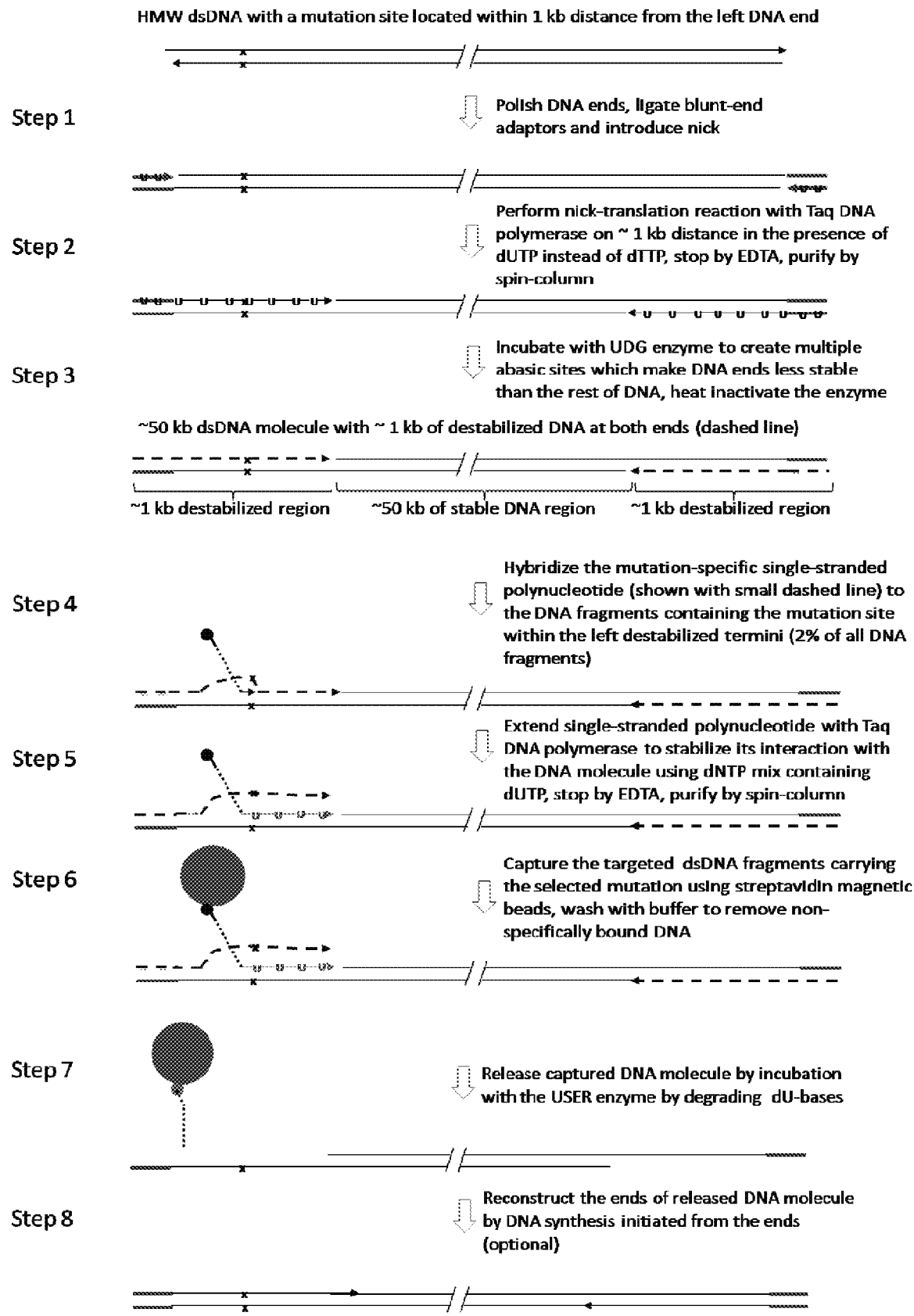
FIG. 14 is a flow diagram of a procedure for allele-specific isolation of target double-stranded polynucleotides.

Current methods, including PCR, array hybridization and next generation sequencing, can determine genotypes for millions of SNPs across a genome. None of these methods, however, allow linkage or phase information of SNPs, i.e., haplotype information, which is critical for genetic analysis of disease and other complex traits. The few methods that exist for haplotype determination, such as chromosome sorting, cell hybrid analysis and single clone/molecule analysis are laborious. The method described in FIG. 14 allows capture of large DNA fragments for haplotype analysis in an allele- or SNP-specific way. This method is used to efficiently partition a diploid locus into its haploid counterparts in a rapid single tube format. Following capture of large fragments of DNA flanking the SNP or allele of interest, SNP genotyping of the captured product is performed by conventional methods. In addition, SNP-specific capture can be followed by bisulfite treatement to reveal methylation patterns for analysis of epigenetic modifications in a haplotype-specific way.

In various embodiments, the methods disclosed herein are useful for isolating specific alleles, haplotypes, and/or polynucleotides having at least one specific mutation. Similarly, the methods disclosed herein are useful for isolating target DNA from particular species or subspecies in a microbial population. A flow diagram for allele-specific or mutation-specific capture of DNA is presented in FIG. 14. Genomic DNA preparations generated by methods known in the art result in a population of DNA fragments of a desired length. In some aspects, the DNA fragments are about 50 kilobases (kb) in length. In some embodiments, the DNA is randomly fragmented. In some embodiments, the DNA fragments are generated by random fragmentation/shearing due to mechanical forces. In some embodiments, the DNA fragments are generated by an enzyme capable of cleaving phosphodiester bonds. In some embodiments, the enzyme is a restriction endonuclease. In some embodiments, the enzyme is a nickase. In some embodiments, the enzyme is DNaseI. A particular mutation will be present within 1 kb of the end of a DNA fragment in approximately 4% of all DNA fragments with the mutation. Genomic DNA preparations containing fragments are treated to generate blunt ends to which adaptor sequences with nickase sequences are ligated using techniques well known and routinely practiced in the art. The DNA is then treated with the appropriate nickase. Next, a nick-translation reaction is performed as described above to incorporate uracil into the newly synthesized DNA strand over a desired length. In some aspects, this length is 1 kb. The DNA is incubated with UDG to generate abasic sites, thereby generating a destabilized region. An allele-specific, mutation-specific, haplotype-specific, species-specific, or SNP-specific single-stranded polynucleotide comprising a linker portion and a capture portion is then hybridized to the target DNA under appropriate conditions. The single-stranded polynucleotide displaces the strand with abasic sites in the destabilized region because the single-stranded polynucleotide hybridizes to the complementary strand with greater affinity than the strand with abasic sites. The linker portion is complementary to the region comprising the mutation such that the linker portion does not hybridize to a non-mutated sequence in a manner efficient enough to function as a primer for DNA synthesis. In some embodiments, the nucleotide at or near the 3'end of the single-stranded polynucleotide is SNP-specific, such that the single-stranded polynucleotide will more efficiently function as a primer for DNA synthesis when the linker portion is complementary to the target polynucleotide (i.e., SNP-containing polynucleotide) but will not efficiently function as a primer when the linker portion is less than complementary (i.e., includes at least a single mismatch), with a non-target polynucleotide (i.e., a "wild-type" polynucleotide). Next, the linker portion of the single-stranded polynucleotide is extended by a DNA polymerase, again incorporating uracil instead of thymine. Next, the target DNA is isolated by interaction of the capture portion with a capture substance. In some aspects and without limitation, the capture portion includes biotin and the capture substance is streptavidin. Finally, the captured target DNA is released with cleavage of the linker portion of the single-stranded polynucleotide. In some embodiments, cleavage is performed using UDG/AP. As will be appreciated by a person of skill in the art, the procedure outlined above can be carried out by targeting either strand of the target double-stranded polynucleotide.

Figure 15:
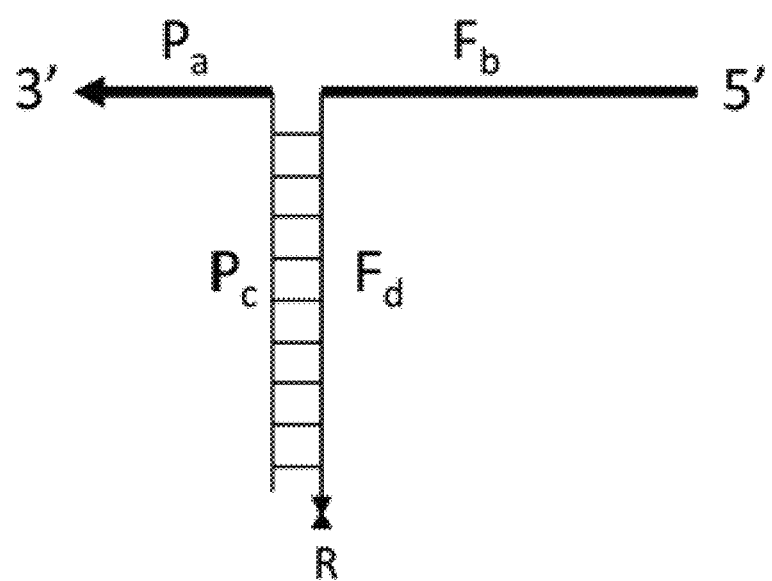
FIG. 15 is a schematic of an alternative single-stranded polynucleotide comprising a linker portion and a capture portion.

In various embodiments, the "single-stranded polynucleotide" comprising a linker portion and a capture portion is a primer pair which comprises a first polynucleotide and a second polynucleotide, the first polynucleotide comprising a first domain [Pa] that is complementary to a first target polynucleotide region and a second domain [Pc] comprising a unique polynucleotide sequence, and the second polynucleotide comprising a first domain [Fb] that is complementary to a second target polynucleotide region and a second domain [Fd] comprising a polynucleotide sequence sufficiently complementary to the second domain of the first polynucleotide such that the second domain of the first polynucleotide and the second domain of the second polynucleotide will hybridize under appropriate conditions. In some embodiments, the second domain of the first polynucleotide comprises the capture portion. In some embodiments, the second polynucleotide is comprised of RNA. The structural relationship of the basic polynucleotide combination is shown in FIG. 15. In methods for isolating a specific allele or a polynucleotide have a specific mutation, the region Pa of the first polynucleotide of the primer pair has a sequence that is complementary to the specific allele or the region in the double-stranded target polynucleotide with the specific mutation, such that the region Pa will hybridize to the desired allele or specific mutation with the ability to prime a polymerase reaction, and Pa will not hybridize to an undesired allele or a region in the double-stranded polynucleotide that does not include the specific mutation efficiently enough to prime a polymerase reaction.

In some embodiments, the procedure described above and outlined in FIG. 14 is carried out using the single-stranded polynucleotide structure of FIG. 15.

VI. Extending Single-stranded Polynucleotides

According to some embodiments, the single-stranded polynucleotides comprising a linker portion and a capture portion are extended. According to embodiments wherein the single-stranded region of the target polynucleotide is a flap, the flap is extended. In some embodiments the extension of the single-stranded polynucleotides or flaps adds specific sequences. In some embodiments, the sequences added by extension comprise simplified base compositions. To prevent or minimize intramolecular interactions, in some embodiments, the extended sequences comprise primarily C and T bases. In other embodiments, the extended sequences comprise primarily G and A bases. In other embodiments, the extended sequences comprise primarily one base. In yet other embodiments, the sequence added by extension interacts with the capture substance.

According to various embodiments, the extension of the single-stranded polynucleotides or flaps is performed using the methods and devices disclosed in Example 4.

Figure 16:
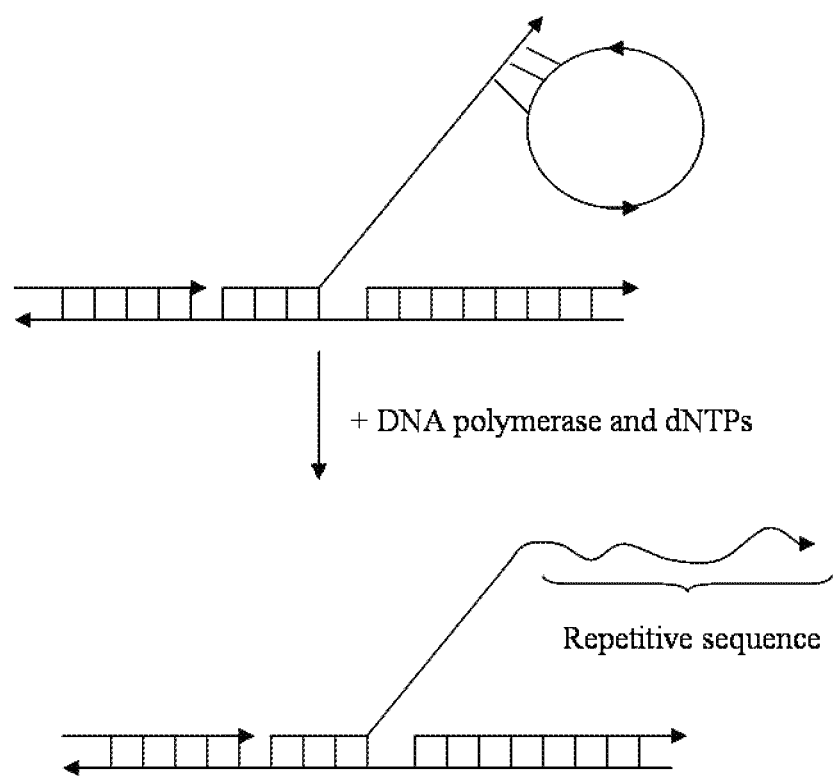
FIG. 16 is a schematic of rolling circle DNA amplification to add repetitive sequences to the 3' end of a single-stranded polynucleotide.

Rolling circle amplification (RCA) is a unique example of primer extension reaction where multiple rounds of replication of a circular polynucleotide template can be achieved without thermal denaturation of double stranded polynucleotides or additional enzymes. The product of RCA is a repetitive sequence $(cA)_n$ where A is a sequence of the circular template and cA is its complement. According to some embodiments, the rolling circle amplification technique is used to extend single-stranded polynucleotides. Rolling circle amplification is well-known in the art. Briefly, the 3' end of a single-stranded polynucleotide of the disclosure anneals to a circular DNA template and functions as a primer to allow a DNA polymerase to extend the single-stranded polynucleotide with a repetitive sequence (illustrated in FIG. 16).

Because the DNA template is circular, the DNA polymerase will continue to polymerize until the reaction is stopped by chemically-inactivating the reaction, by heat-inactivating the polymerase, or by exhaustion of the dNTP substrate pool.

VII. Capture Substance

Figure 17:
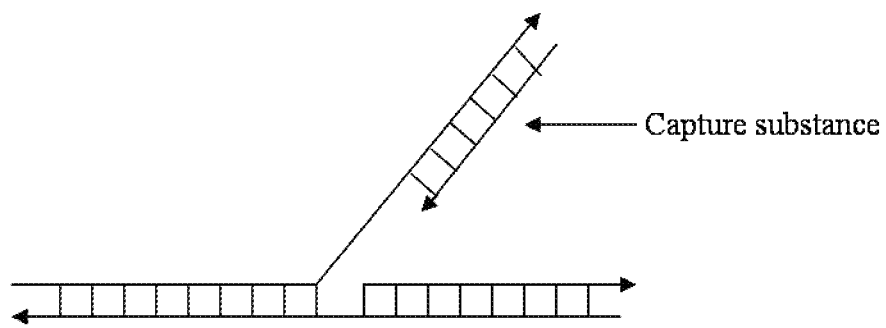
FIG. 17A is a schematic of a capture substance interacting with a target polynucleotide, wherein the capture substance comprises a single-stranded polynucleotide that is capable of interacting (i.e. hybridizing) with a single-stranded region of the target polynucleotide molecule.
In FIG. 17B, the capture substance is attached to biotin.
Figure 17:
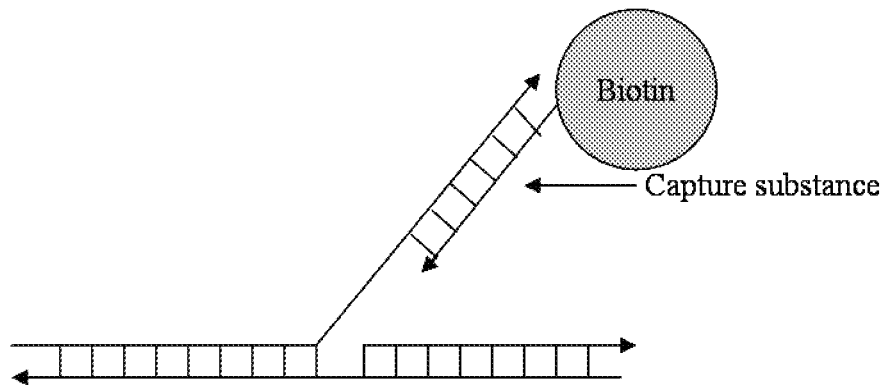

In some aspects, the capture substance comprises a single-stranded polynucleotide that is capable of interacting (i.e. hybridizing) with a single-stranded region of the target polynucleotide molecule, as illustrated in FIG. 17A.

In other aspects, the single-stranded polynucleotide of the capture substance is covalently attached to a biotin molecule, as illustrated in FIG. 17B.

The biotin may be attached at either the 3' or the 5' end of the single-stranded polynucleotide. Attachment of biotin may be achieved by any method known in the art. In some aspects, the capture substance further comprises a bead coated with streptavidin, as illustrated in FIG. 18A.

Beads used to perform the methods of the disclosure may be any type of bead commonly used in molecular biology, including but not limited to agarose, sepharose, or magnetic beads. In a specific aspect, the streptavidin-coated bead is magnetic.

Figure 18:
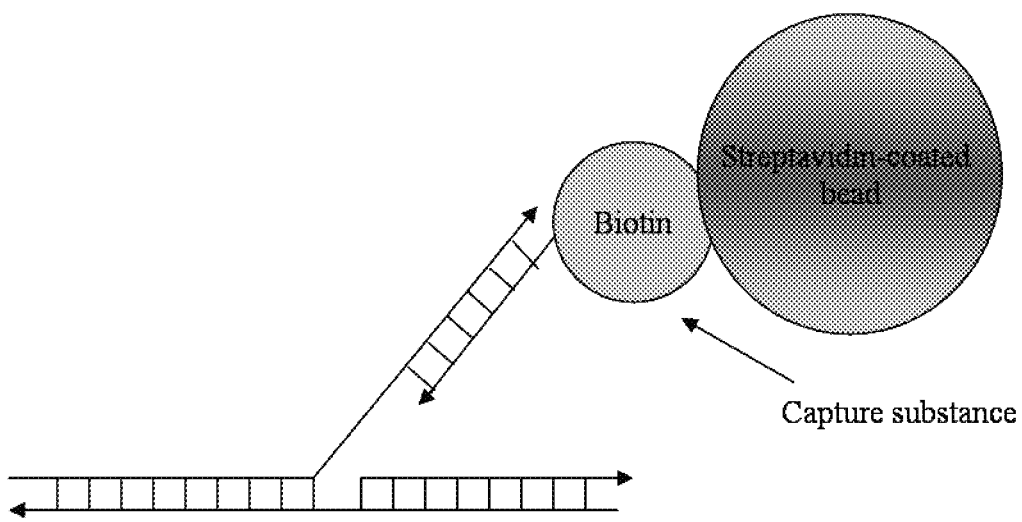
FIG. 18A is a schematic of a capture substance comprising the biotinylated polynucleotide of FIG. 17 and a bead coated with streptavidin.
FIG. 18B is a schematic of a capture substance comprising a single-stranded polynucleotide directly attached to a bead.
Figure 18:
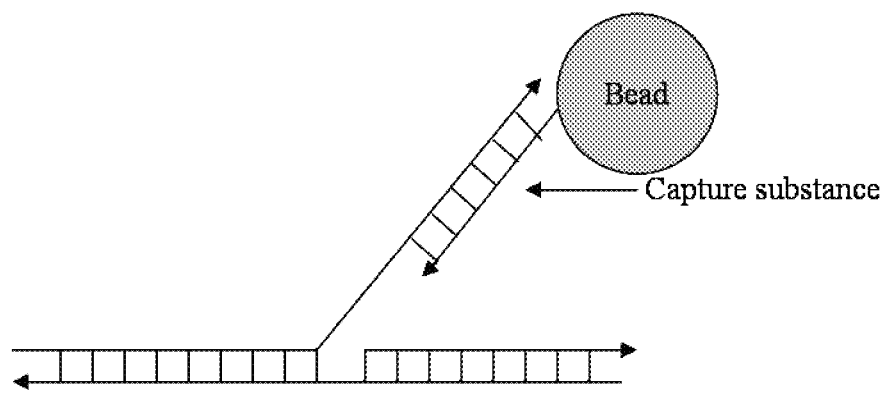

In some aspects of the disclosure, the capture substance comprises a single-stranded polynucleotide capable of interacting (i.e. hybridizing) with a single-stranded region of the target polynucleotide molecule wherein the single-stranded polynucleotide is covalently attached to a bead, as illustrated in FIG. 18B.

In some aspects, the bead is magnetic.

Figure 19:
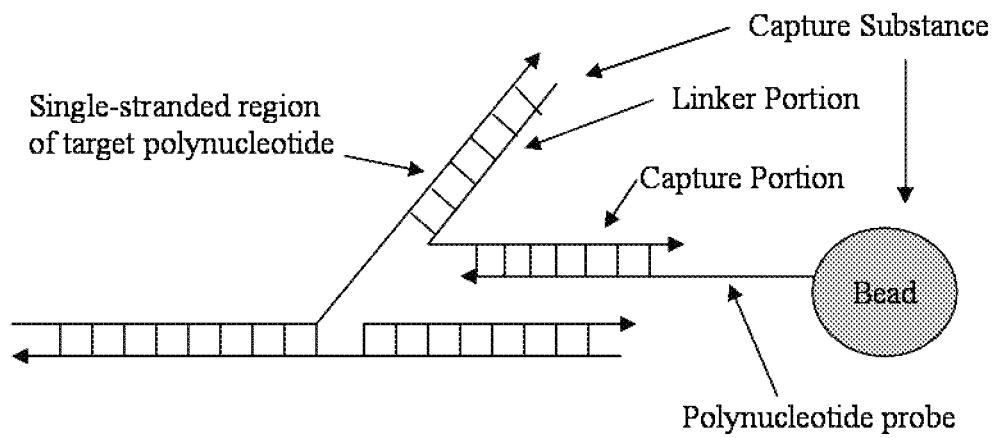
FIG. 19A is a schematic of a substantially double-stranded target polynucleotide bound to a single-stranded polynucleotide comprising a linker portion and a capture portion, the linker portion hybridizing with the single-stranded region of the target polynucleotide and the capture portion hybridizing with a single-stranded probe which is covalently attached to a bead.
FIG. 19B is a schematic of a substantially double-stranded target polynucleotide bound to a single-stranded polynucleotide comprising a linker portion and a capture portion, the linker portion hybridizing with the single-stranded region of the target polynucleotide and the capture portion hybridizing with a single-stranded probe which is covalently attached to a bead.
Figure 19:
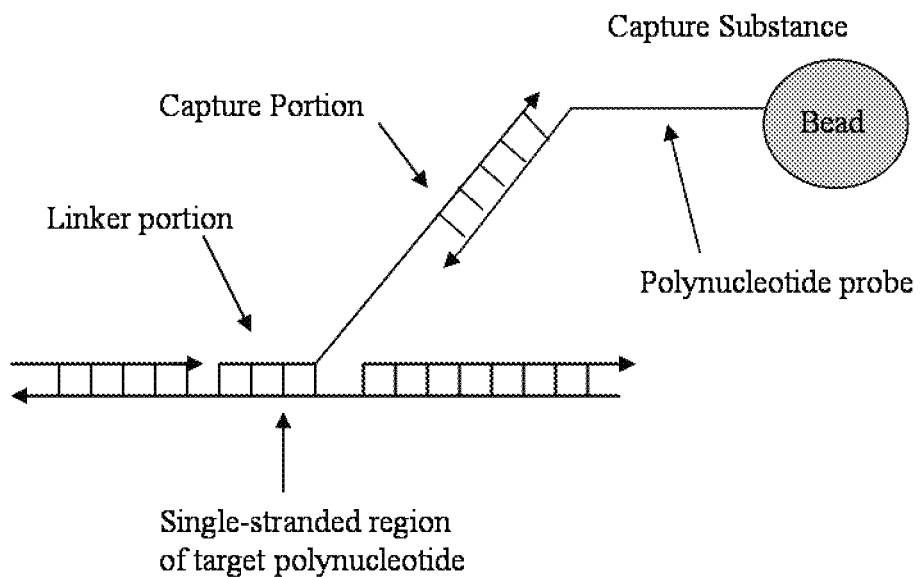

In some aspects of the disclosure, the capture substance comprises a single-stranded polynucleotide capable of interacting (i.e. hybridizing) with a single-stranded region of the target polynucleotide molecule, wherein the single-stranded region is a flap. The single-stranded polynucleotide may comprise a linker portion and a capture portion, the linker portion hybridizing with the single-stranded region of the target polynucleotide and the capture portion hybridizing with a single-stranded probe which is covalently attached to a bead, as illustrated in FIG. 19A.

In some embodiments of the disclosure, the capture substance comprises a single-stranded polynucleotide capable of interacting (i.e. hybridizing) with a single-stranded region of the target polynucleotide molecule, wherein the single-stranded region is a gap. The single-stranded polynucleotide may comprise a linker portion and a capture portion, the linker portion hybridizing with the single-stranded region of the target polynucleotide and the capture portion hybridizing with a single-stranded probe which is covalently attached to a bead, as illustrated in FIG. 19B.

In some embodiments, the internal single-stranded region comprises a 5' flap. In these embodiments the single-stranded polynucleotide comprising a linker portion and a capture portion comprises a modified stem-loop structure, as illustrated in FIG. 20A.

Figure 20:
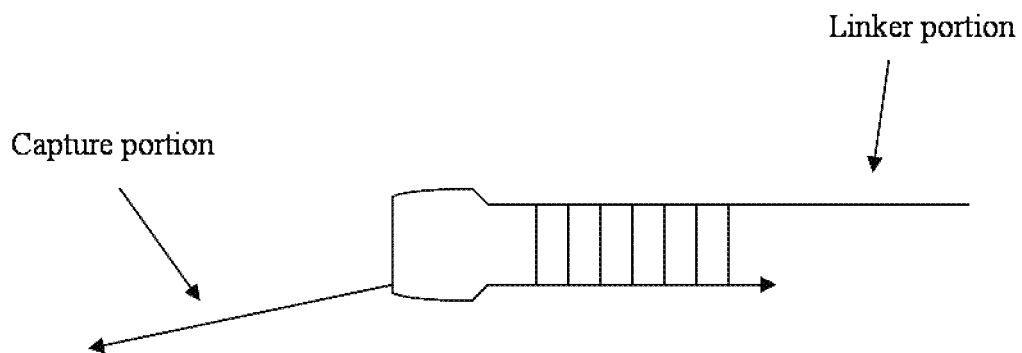
FIG. 20A is a schematic of a single-stranded polynucleotide comprising a linker portion and a capture portion, wherein the linker portion comprises a modified stem-loop structure.
FIG. 20B is a schematic of the single-stranded polynucleotide of FIG. 20A interacting with a target polynucleotide and a capture substance.
Figure 20:
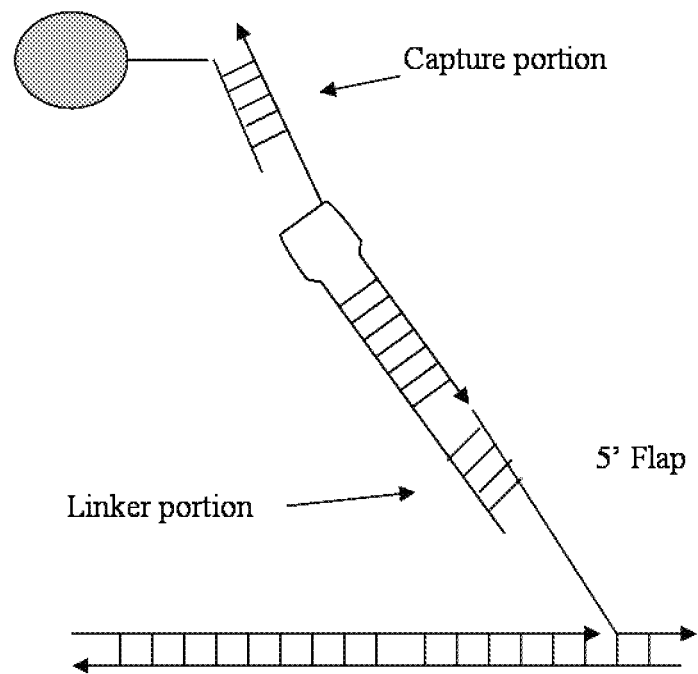

As with the previously described single-stranded polynucleotides comprising a linker portion and a capture portion, the modified stem-loop structure comprises a linker portion that is complementary to the 5' flap and a capture portion that interacts with a capture substance, as illustrated in FIG. 20B.

The capture portion of the modified stem-loop structure may be extended by the methods described earlier to incorporate repetitive sequences that allow for greater amount of capture substance binding.

Figure 21:
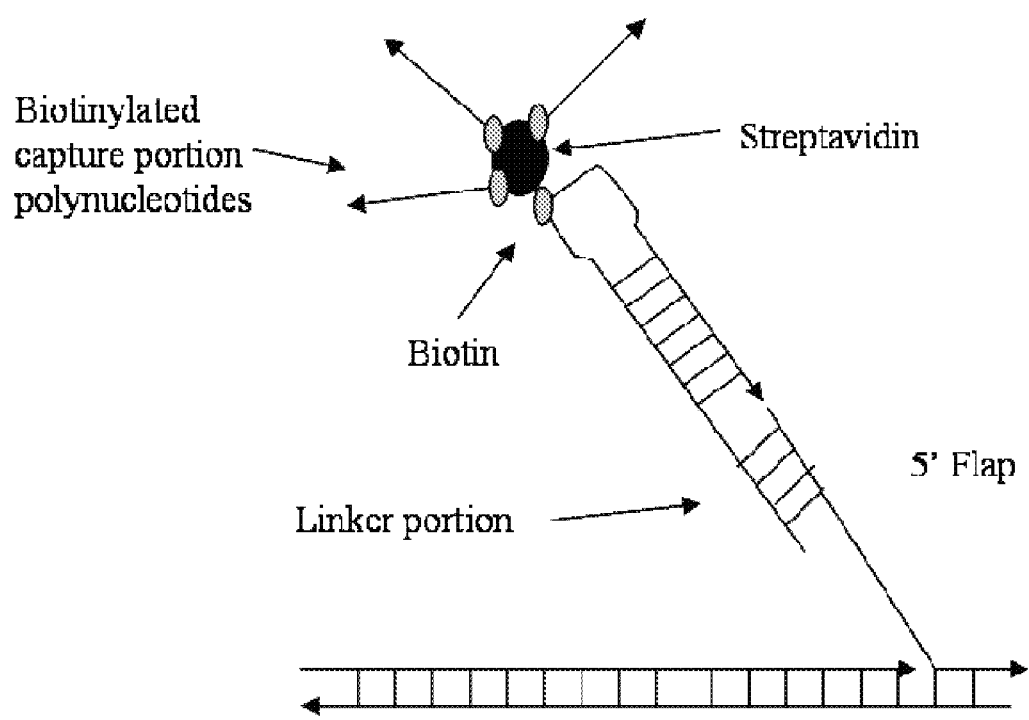
FIG. 21 is a schematic of the modified stem-loop structure of FIG. 19 further comprising a biotin molecule covalently attached to the stem-loop structure.

In another embodiment, the modified stem-loop structure comprises a biotin molecule covalently attached to the stem-loop structure. Up to 3 capture portion polynucleotides can be associated with the stem-loop structure by utilizing biotinylated capture portion polynucleotides, as illustrated in FIG. 21.

In some embodiments, the polynucleotide probe is attached to a first binding partner. The first binding partner may be any molecule capable of interacting with a second binding partner. For example, in some embodiments, the first binding partner is biotin and the second binding partner is streptavidin. In another embodiment, the first binding partner is an antigen and the second binding partner is an antibody that recognizes the antigen. A person of skill in the art will recognize that the polynucleotide probe may be attached to any molecule that interacts in a specific manner with another molecule or substance to carry out disclosed methods.

In some aspects of the methods, a single-stranded polynucleotide probe is covalently attached to a bead. The single-stranded probe comprises a sequence complementary to the capture substance. When combined with the methods of extending a single-stranded polynucleotide described above, it is apparent that the 3' end of the capture portion may be extended to incorporate repetitive sequences, thus allowing the practitioner to attach multiple polynucleotide probes, thereby increasing the specificity and avidity for the target polynucleotide.

In one aspect, the single-stranded probe of the capture substance is extended by rolling circle amplification to generate a repetitive polynucleotide sequence complementary to the extended capture portion of the single-stranded polynucleotide attached to the target polynucleotide. In another aspect, the single-stranded probe of the capture substance is extended by the methods and devices described in Appendix A to generate a repetitive polynucleotide sequence complementary to the extended capture portion of the single-stranded polynucleotide attached to the target polynucleotide.

Figure 22:
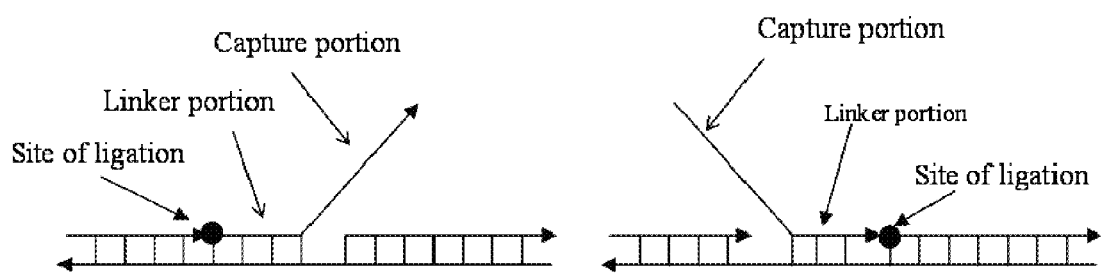
FIG. 22 is a schematic of a single-stranded polynucleotide of the capture substance ligated to the target polynucleotide by a DNA ligase.

In various aspects, the single-stranded polynucleotide of the capture substance is ligated to the target polynucleotide by a DNA ligase, as illustrated in FIG. 22.

In some aspects of the methods, the polynucleotide probe is attached to a solid support. In one aspect, the solid support is a polypropylene tube. Attaching the polynucleotide probe to a polypropylene tube allows a practitioner to use the probe-conjugated tubes for easy isolation of target polynucleotides. In another aspect, the solid support is a glass slide. Attaching the polynucleotide probe to a glass slide allows a practitioner of the disclosed methods to create an array of target polynucleotides for further study.

The above illustrations are solely intended to explain the disclosed methods and compositions. The illustrations are not intended to limit the claims in any manner. A person of skill in the art will appreciate that increasing the number of single-stranded regions will allow for increased specificity and avidity for a particular target polynucleotide.

VIII. Releasing the Target Polynucleotide

In some methods of the disclosure, the target double-stranded polynucleotide molecule is released from the capture substance. In another embodiment, the target polynucleotide is released by enzymatic degradation of the hybridized capture portion and polynucleotide probe described above. Briefly, in one aspect, the capture portion is comprised of RNA. In another aspect, the linker portion is comprised of RNA. In either aspect, incubation with RNase H will destroy RNA within the RNA/DNA hybrid, thus releasing the target polynucleotide.

Figure 23:
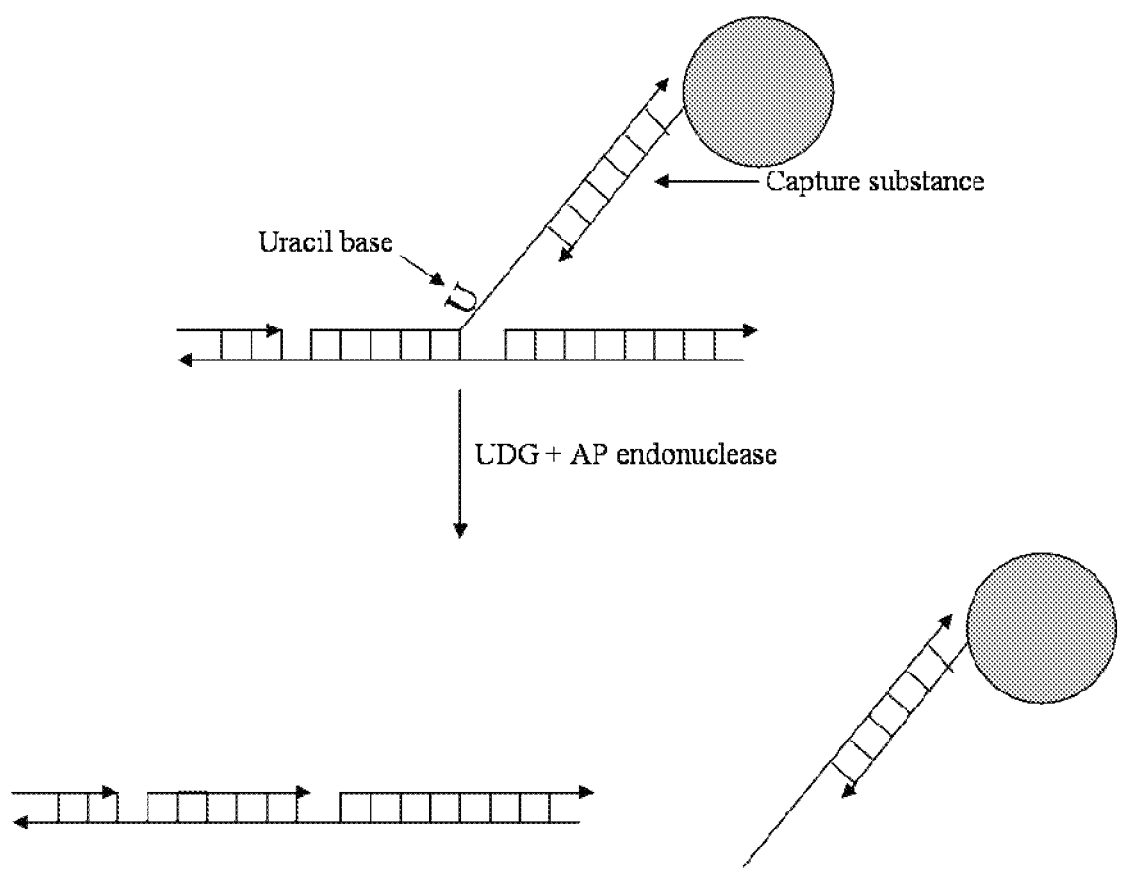
FIG. 23 is a schematic of target polynucleotide release from capture substance by treatment of the target polynucleotide/capture substance complex with Uracil-DNA glycosylase (UDG) and an Apurinic/Apyrimidinic endonuclease (AP endonuclease). In the embodiments utilizing release by UDG/AP treatment, a uracil base is incorporated in the single-stranded polynucleotide comprising a capture portion and a linker portion.

In yet another embodiment, the target polynucleotide is released by treatment of the target polynucleotide/capture substance complex with Uracil-DNA glycosylase (UDG) and an Apurinic/Apyrimidinic endonuclease (AP endonuclease). In the embodiments utilizing release by UDG/AP treatment, a uracil base is incorporated in the single-stranded polynucleotide comprising a capture portion and a linker portion as depicted in FIG. 23.

In yet another embodiment, the polynucleotide target is released by subjecting the target polynucleotide/capture substance complex to conditions that disrupt the hybridization of the linker portion to the target polynucleotide while allowing the target polynucleotide to remain double-stranded, i.e., by altering temperature and buffer conditions that disfavor the linker/target hybrid. Such conditions can readily be determined by a person of skill in the art.

IX. Compositions

Also contemplated within the scope of the invention is a composition comprising a substantially double-stranded polynucleotide molecule with an internal single-stranded region that is associated with a single-stranded polynucleotide, the single-stranded polynucleotide comprising a linker portion and a capture portion, the linker portion sufficiently complementary to the single-stranded region to allow the linker portion and the single-stranded region to hybridize, and the capture portion not complementary to the substantially double-stranded polynucleotide molecule.

Figure 24:
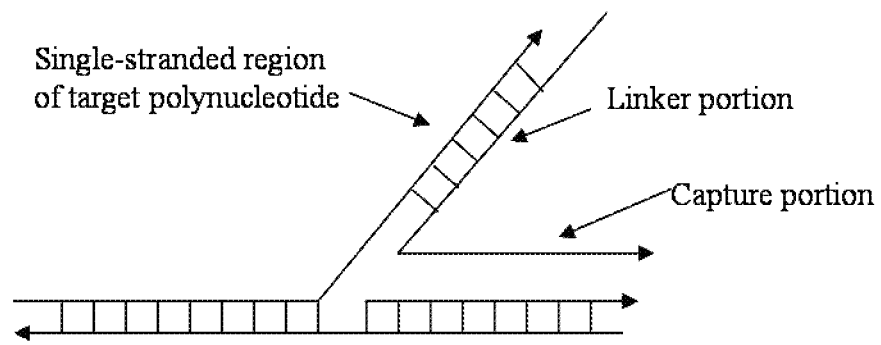
FIG. 24A is a schematic of a single-stranded region of the target polynucleotide as a "flap" interacting with a single-stranded polynucleotide with a capture portion and a linker portion.
FIG. 24B is a schematic of a single-stranded region of the target polynucleotide as a "gap" interacting with a single-stranded polynucleotide with a capture portion and a linker portion.
Figure 24:
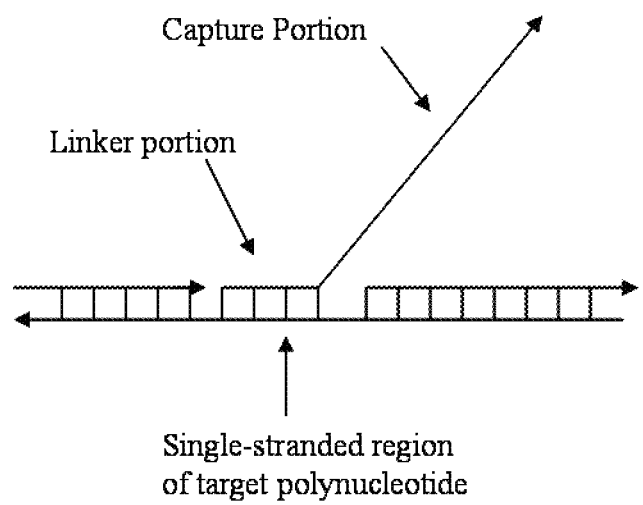

In some embodiments, the single-stranded region of the target polynucleotide is a flap, as illustrated in FIG. 24A. In another embodiment, the single stranded region is a gap, as illustrated in FIG. 24B.

In some embodiments, the composition further comprises a polynucleotide probe hybridized to the capture portion of the single-stranded polynucleotide. In a specific embodiment, the polynucleotide probe is hybridized to a bead. In a more specific embodiment, the bead is magnetic.

In some embodiments of the composition, the polynucleotide probe is hybridized to the single-stranded region of the flap.

In some embodiments, the polynucleotide probe is attached to a first binding partner. The first binding partner may be any molecule capable of interacting with a second binding partner. For example, in some embodiments, the first binding partner is biotin and the second binding partner is streptavidin. In another embodiment, the first binding partner is an antigen and the second binding partner is an antibody that recognizes the antigen. A person of skill in the art will recognize that the polynucleotide probe may be attached to any molecule that interacts in a specific manner with another molecule or substance to create the disclosed compositions.

X. Kits

The invention further provides kits comprising a single-stranded polynucleotide comprising a linker portion and a capture portion, the linker portion having a sequence sufficiently complementary to hybridize to a single-stranded region of a substantially double-stranded target polynucleotide molecule under appropriate conditions, and the capture portion not complementary to the single-stranded region of the target; and a capture substance that interacts with the capture portion of the single-stranded polynucleotide.

The invention is further described in the following examples. The examples serve only to illustrate the invention and are not intended to limit the scope of the invention in any way.

EXAMPLES

Example 1 pUC19 Capture by Gap Creation Using Nick-translation DNA Synthesis

Materials Used in the Experiments:

| Reagent | Source | Catalog Number |
| --- | --- | --- |
| NEB Buffer 2 | NEB | B7002S |
| Nb.BsrDI | NEB | R0648S |
| MgCl2 | NEB | 0011004 |
| Taq Mg-free buffer | NEB | 0011005 |
| dATP | Invitrogen | 55082 |
| dGTP | Invitrogen | 55084 |
| dCTP | Invitrogen | 55083 |
| dTTP | Invitrogen | 55085 |
| dUTP | Promega | U119A |
| Taq polymerase | NEB | M0320L |
| 100X BSA | NEB | B9001S |
| BsrDI | NEB | R05745 |
| SYBR Green | Bio-Rad | 170-8882 |
| SYBR Gold | Invitrogen | S-11494 |
| 25bp ladder | Invitrogen | 10488-022 |
| 1kb ladder | Invitrogen | 10787-018 |
| pUC19 | NEB | N3041L |
| human genomic DNA | in-house blood prep | |
| 6% TBU polyacrylamide gel | Invitrogen | EC68652BOX |
| M-270 DynaBeads | Invitrogen | 653.05 |
| USER | NEB | M55055 |
| TE Buffer | Teknova | T0227 |
| QIAQuick PCR Purification kit | Qiagen | 28106 |
| Genomic DNA Clean and Concentrator | Zymo Research | D4010 |
| UDG | NEB | B0280S |

To illustrate the utility of the DNA capture system, capture of pUC19 DNA following single-stranded gap creation by nick-translation DNA synthesis was carried out according to the following procedure.

Step 1: Nicking

A water bath was warmed to 64° C. NEB Buffer 2 and pUC19 were thawed at room temperature. A 400 uL nicking reaction was set up with NEB enzyme Nb.BsrDI: 332 uL water, 40 uL buffer 2, 20 uL pUC19 DNA (20 ug total), 8 uL Nb.BsrDI. The mixture was gently vortexed and incubated 1 hour at 64° C.

Step 2: Purification of Nicking Reaction

Qiagen's QIAquick PCR Purification kit was used (with modifications), the nicked pUC19 was split between two tubes, 200 uL per tube. 1mL Buffer PB was added per tube, inverted, and transfered to a column. The tubes were centrifuged at 11,000×g for 20 seconds and the waste was decanted. The reactions were washed once with 750 uL Buffer PE, centrifuged at 11,000×g for 1 minute, and the waste was decanted. The reactions were washed once with 250 uL Buffer PE, centrifuged at 11,000×g for 1 minute, and the waste was decanted. The tubes were centrifuge at 16,000×g for 1 minute, and the waste was decanted. The grooves in the column were aspirated by keeping the tip still while turning the tube. The column was transferred to a new microcentrifuge tube and eluted once with 30 uL Buffer EB. After buffer addition to column and incubation for one minute, the tubes were centrifuged at 11,000×g for 20 seconds. An additional 20 uL Buffer EB was added to the column. After buffer addition to column and incubation for one minute, the tubes were centrifuged at 11,000×g for 20 seconds. The eluted products were combined and the DNA concentration was analyzed on NanoDrop, and adjusted to 100 ng/uL with Buffer EB.

Step 3: Nick Translation

Controls utilized included reactions with dNTP only (i.e., no dU incorporation) and reactions with no nick translation (i.e., no Taq addition). A thermocycler was set to 50° C. A 20 uL nick translation reaction was set up for the dNTP controls. Each reaction contained the following: 8.5 uL water, 4 uL nicked DNA (400 ng total), 2.5 uL 3 mM $MgCl_2$, 2 uL Taq Mg-free buffer, 1 uL 10 mM dT/A/G/C, 2 uL 10 U Taq polymerase. One tube was set up without Taq polymerase and one tube with Taq polymerase. A 40 uL nick translation reaction was prepared for the dUTP samples. Each reaction contained the following: 17 uL water, 8 uL nicked DNA (800 ng total), 5 uL 3 mM $MgCl_2$, 4 uL Taq Mg-free buffer, 2 uL 10 mM dU/A/G/C, 4 uL 10 U Taq polymerase. One tube was prepared without Taq polymerase and one tube with Taq polymerase. Tubes were placed in the warm thermocycler and reactions were allowed to proceed for 2 minutes at 50° C. Reactions were stopped by adding 1 uL of 0.5M EDTA to the dNTP tubes and 2 uL of 0.5M EDTA to the dUTP tubes, and flicking tubes to mix. The reactions were column purified as described above for nicking, but eluted one time with 20 uL Buffer EB for dNTP controls and two times with 20 uL for dUTP samples.

Step 4: Verification of Nick Translation Success by Restriction Endonuclease Digestion 10 uL of the dNTP controls and dUTP samples were digested with NEB's restriction endonuclease BsrDI. A 14 uL reaction contained the following: 10 uL nick translated product (200 ng total), 2 uL NEB Buffer 2, 1 uL 20× BSA, 1 uL BsrDI. The reactions were allowed to proceed at 64° C. for 2 hours. Samples were run on a 6% denaturing Tris-Boric Acid-Urea polyacrylamide gel. To each sample was added 14 uL formamide buffer and heat at 95° C. for 5 minutes. 20 uL was loaded onto the gel. The ladder was a 25 bp ladder. 1 uL of ladder stock was added to 20 uL formamide buffer and heated at 95° C. for 5 minutes. 10 uL of ladder was loaded onto the gel on each end of the samples. The gel was run at 150V for 20-30 minutes and stained with SYBR Gold.

Figure 25:
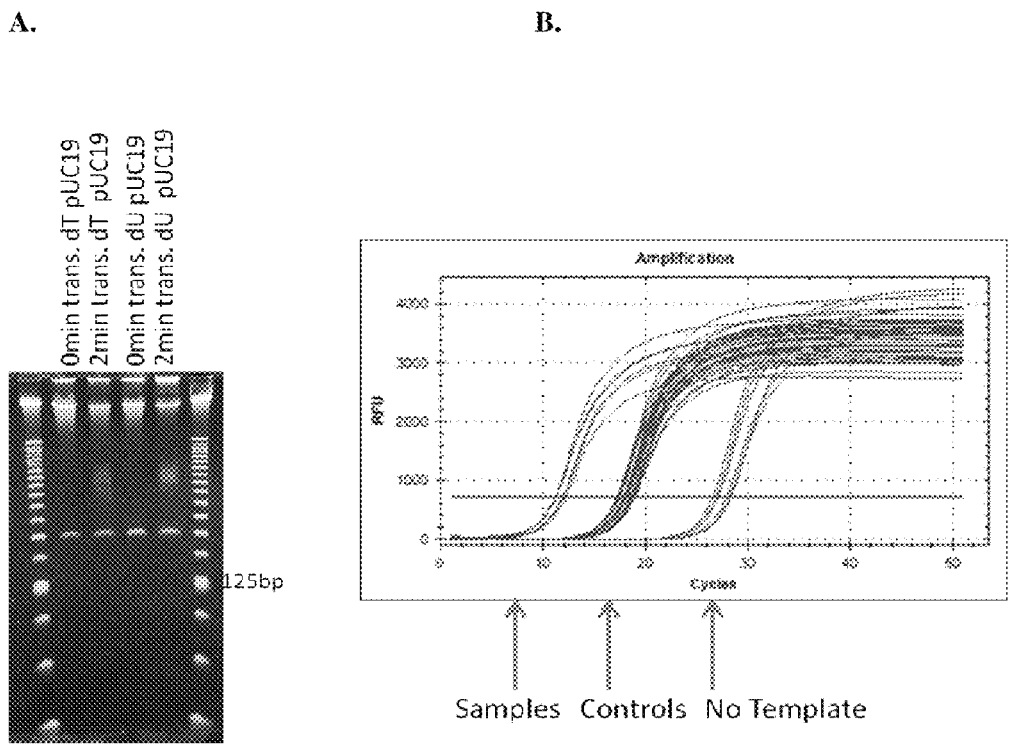
FIG. 25A displays the results of a nick-translation reaction incorporating uracil into a target polynucleotide (pUC19).
FIG. 25B displays the results of a qPCR reaction of the USER-treated, captured target polynucleotide by measuring SYBR green fluorescence.
FIG. 25C is an agarose gel of the captured target polynucleotide.
Figure 25:
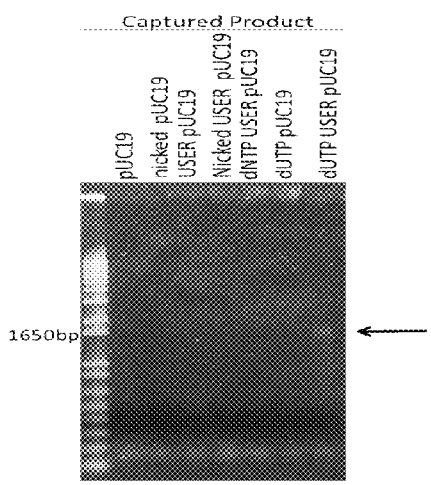

Results are shown in FIG. 25A. Nick translation was successful for both controls and samples and the rate of nick translation for dUTP was the same as that for dNTP.

Step 5: Treatment of Samples with USER

A thermocycler was warmed to 37° C. 10 uL of purified dNTP controls, dUTP samples, pUC19, and nicked pUC19 were treated with NEB enzyme USER (200 ng DNA in each reaction). USER (uracil-specific excision reagent) is a mixture of Uracil DNA glycosylase (UDG) and the DNA glycosylase-lyase Endonuclease VIII. 1 uL of USER was added to each tube and incubated at 37° C. for 1 hour. Following the 1 hour incubation, temperature was increased to 50° C. and the samples were incubated for 2 minutes to dissociate bases.

Step 6: Capture

Capture probes were diluted to 4 uM in TE buffer. 10 uL of DNA was added to 10 uL 1× binding buffer and 1 uL 4 uM capture probe. The capture probe sequence was:

```
                                    (SEQ ID NO: 1)
TTGCTACAGGCATCGTGGTGTCACGCTCGTCGTTTGGTATGGCTTCATTC

AGCTAAAAA/3Bio/.
```

A capture reaction was set up for the following controls and samples: pUC19; Nicked pUC19; pUC19 USER-treated; pUC19 nicked and USER-treated; dUTP—no USER treatment; dUTP—USER-treated; dNTP—USER-treated. The reactions were incubated at room temperature for 1 hour. Invitrogen M-270 DynaBeads were washed three times with 80 uL 1× Binding Buffer (10 uL of beads per reaction). 10 uL washed beads were added to each reaction. The reactions were incubated with gentle shaking at room temperature for 1 hour. Beads were washed three times with 1× Binding Buffer then two times with TE buffer by placing samples in magnet, removing supernatant, then adding 100 uL of the appropriate buffer for each wash. After the final wash, 50 uL TE buffer was added.

Step 7: qPCR of Captured Product

Four reactions per sample were set up using the following amounts per 21 uL reaction: 12.5 uL SYBR Green, 3 uL of each 1.6 uM primer mix 1 and primer mix 2, 5.5 uL water. Captured DNA was diluted by adding 10 uL of capture to 90 uL water. 96 uL of mix was aliquoted to a tube per DNA sample. 4 uL of DNA was added to the mix. Components were flicked to mix and then aliquoted to 25 uL per well of a PCR plate. A "no template" (i.e., no DNA) reaction was included as a control. Reactions were set up in triplicate. Total DNA per reaction was 3.4 ng. Cycling conditions: 95° C. for 1 minute—1 cycle. Then 50 cycles of: 95° C. for 15 seconds and 62° C. for 1 minute. A Melt Curve analysis step was included to ensure primers were not self-annealing. Primer 1 mix was primer TACCGCACAGATGCGTAAGGAGAA (SEQ ID NO: 2) and primer CCAACTTAATCGCCTTG-CAGCACA (SEQ ID NO: 3). Primer 2 mix was primer TGCAAGCTTGGCGTAATCATGGTC (SEQ ID NO: 4) and primer TAATGCAGCTGGCACGACAGGTTT (SEQ ID NO: 5).

The results are illustrated in FIG. 25B. The capture samples were detected 6 cycles before controls, indicating successful capture of DNA.

Step 8: Verification of Capture on 1% Agarose Gel

The remaining captured product was heated at 95° C. for 30 seconds and placed in a magnet, and the supernatant was quickly removed. 10 uL of the eluted capture product was run on a 1% agarose gel.

Results are illustrated in FIG. 25C. The procedure led to the successful capture of the target DNA, and the captured product was approximately 1.6 kb.

Example 2 pUC19 Capture by Displacement

Figure 26:
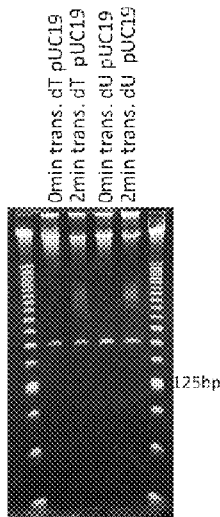
FIG. 26A displays the results of a nick-translation reaction incorporating uracil into a target polynucleotide (pUC19).
FIG. 26B displays the results of a qPCR reaction of the UDG-treated, captured target polynucleotide by measuring SYBR green fluorescence.
FIG. 26C is an agarose gel of the captured target polynucleotide.
Figure 26:
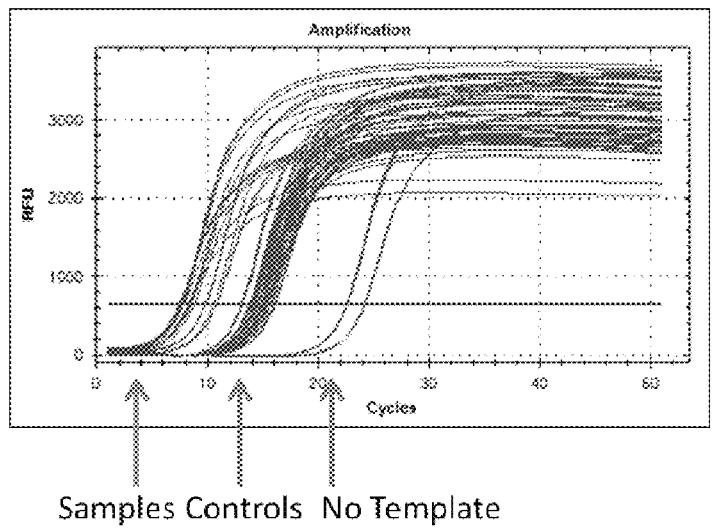
Figure 26:
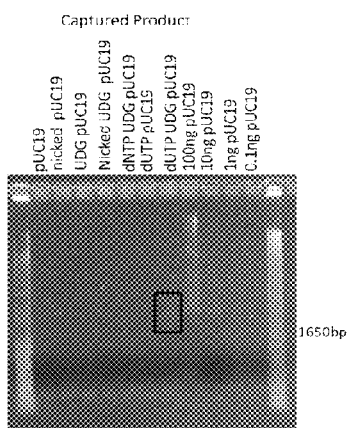

Steps 1-4 were executed as described above for Example 1. The success of the nick translation reaction was demonstrated by gel electrophoresis and is illustrated in FIG. 26A.

Step 5: Treatment of Nick Translated Products with Uracil DNA Glycosylase (UDG)

A thermocycler was heated to 37° C. UDG was diluted 1:5 in 10× UDG Buffer to achieve 1 U/uL. 1 uL of diluted UDG was added to 10 uL (200 ng) of purified nick translated product and the controls pUC19 and pUC19-nicked. Samples were incubated at 37° C. for 10 minutes. 1 uL of 100 mM NaCl and 1 uL of capture probe (same capture probe used in Example 1) were added to each reaction and heated at 50° C. for 5 minutes.

Step 6: Capture

The capture step was set up as described above in Example 1 for the following controls and samples: pUC19; Nicked pUC19; pUC19 UDG-treated; pUC19 nicked and UDG-treated; dUTP—no UDG treatment; dUTP—UDG-treated; dNTP—UDG-treated. The qPCR and gel analysis was performed as described above in Example 1, Steps 7 and 8. A series of pUC19 dilutions in qPCR was performed to quantitate the amount of pUC19 captured in the samples.

The results of this experiment are illustrated in FIG. 26B. The results demonstrate that UDG-treated samples are successfully captured. The UDG-treated samples were detected 6 cycles ahead of controls. The gel analysis shown in FIG. 26C provides a visualization of the captured product.

Example 3 pUC19 Capture in Presence of Human Genomic DNA

Step 1: Nicking

A water bath was warmed to 64° C. NEB Buffer 2 and pUC19 were thawed at room temperature and flicked to mix components in tube. A 400 uL nicking reaction was set up with NEB enzyme Nb.BsrDI as follows: 302.6 uL water, 40 uL NEB Buffer 2, 47.3 uL human genomic DNA (10 ug total), 2 uL pUC19 (200 ng total), 8 uL Nb.BsrDI. The mixtures were gently vortexed then incubated 2 hours at 64° C.

Step 2: Purification of Nicking Reaction

The Zymo Research Genomic DNA Clean and Concentrator Kit manufacturer's instructions were followed. 800 uL ChIP DNA Binding Buffer was added to the 400 uL digest and the mixture was inverted several times. 1 mL was added to the column and centrifuged 30 seconds at 14,000 rcf. The supernatant was then decanted. The remaining 200 uL of digest was loaded onto the column and centrifuge 30 seconds at 14,000 rcf, followed by decanting of the supernatant. 200 uL wash buffer was added to the column and centrifuged 1 minute at 14,000 rcf, followed by a repeat wash. A 10 uL pipet was used to remove traces around the edge of the column. To elute, the column was transferred to a clean microcentrifuge tube, 20 uL of water was added and allowed to sit at room temperature for 1 minute, then centrifuged 30 seconds at 14,000 rcf. DNA concentration was determined on NanoDrop and adjusted to 100 ng/uL. Samples were run on a 1% agarose gel at 10V overnight. FIG. 27A illustrates the results of this experiment. The gel demonstrates the presence of nicked pUC19 and human gDNA.

Step 3: Nick Translation

Controls utilized included reactions with dNTP only (i.e., no dU incorporation) and reactions with no nick translation (i.e., no Taq addition). A thermocycler was set to 50° C. 20 uL nick translation reactions were set up for the dNTP controls: 10.5 uL water, 2 uL DNA (200 ng total), 2.5 uL 3 mM MgCl$_2$, 2 uL Taq Mg-free buffer, 1 uL 10 mM dT/A/G/C, 2 uL 10 U Taq polymerase. One tube was set up without Taq polymerase and one tube with Taq polymerase for each pUC19 and the human gDNA/pUC19 mix. 40 uL nick translation reactions were set up for the dUTP samples: 21 uL water, 4 uL DNA (400 ng total), 5 uL 3 mM MgCl2, 4 uL Taq Mg-free buffer, 2 uL 10 mM dU/A/G/C, 4 uL 10 U Taq polymerase. One tube was set up without Taq polymerase and one tube with Taq polymerase for each pUC19 and human gDNA/pUC19 mix. Tubes were placed in the warm thermocycler and reactions were allowed to go 2 minutes at 50° C. Reactions were stopped by adding 1 uL of 0.5M EDTA to the dNTP tubes and 2 uL of 0.5M EDTA to the dUTP tubes, and flicking tubes to mix. Reactions were column purified with the Zymo Research Genomic DNA Clean and Concentrator kit as described above for nicking, but eluted one time with 20 uL water for dNTP controls and two times with 20 uL water for dUTP samples.

Step 4: Verification of Nick Translation Success by Restriction Endonuclease Digestion A digest of 10 uL of dNTP controls and dUTP samples was set up with NEB's restriction endonuclease BsrDI by adding 2 uL NEB Buffer 2, 1 uL 20× BSA, and 1 uL BsrDI to the 10 uL (100 ng) nick translated product. The samples were incubated at 64° C. for 2 hours. Digested samples were run on a 6% denaturing Tris-Boric Acid-Urea polyacrylamide gel. To each sample was added 14 uL formamide buffer and heat at 95° C. for 5 minutes. 20 uL was loaded onto the gel. The ladder was a 25 bp ladder: 1 uL of ladder stock was added to 20 uL formamide buffer and heated at 95° C. for 5 minutes. 10 uL of ladder was loaded onto the gel on each end of the samples. The gel was run at 150V for 20-30 minutes and stained with SYBR Gold.

FIG. 27B illustrates the results of this experiment. The results demonstrate that nick translation was successful for pUC19-only controls and the rate of nick translation for dUTP is the same as that for dNTP. However, nick translation could not be observed for human genomic DNA. It is possible that nick translation occurred, but may not be visible on a gel.

Step 5: Treatment of Nick Translated Products with UDG

A thermocycler was set to 37° C. UDG was diluted 1:5 in 10× UDG Buffer to achieve 1 U/uL. 1 uL of diluted UDG was added to 10 uL (100 ng) of purified nick translated product and the controls pUC19 and pUC19-nicked. Samples were incubated at 37° C. for 10 minutes. 1 uL of 100 mM NaCl and 1 uL of capture probe (same capture probe used in Example 1) were added to each reaction and heated at 50° C. for 5 minutes.

Step 6: Capture

The capture reaction was performed as described above in Example 1 for the following controls and samples: pUC19; Nicked pUC19; pUC19 UDG-treated; pUC19 nicked and UDG-treated; pUC19 dUTP—no UDG treatment; pUC19 dUTP—UDG-treated; pUC19 dNTP—UDG-treated; Human gDNA nicked; Human+pUC19 nicked; Human+pUC19 nicked dUTP; Human gDNA+pUC19 nicked and UDG-treated dNTP; Human gDNA+pUC19 nicked and UDG-treated dUTP. A qPCR reaction was set up as described above in Example 1, Step 7. A series of pUC19 dilutions was included in the qPCR to quantitate the amount of pUC19 captured in samples.

Figure 27C:
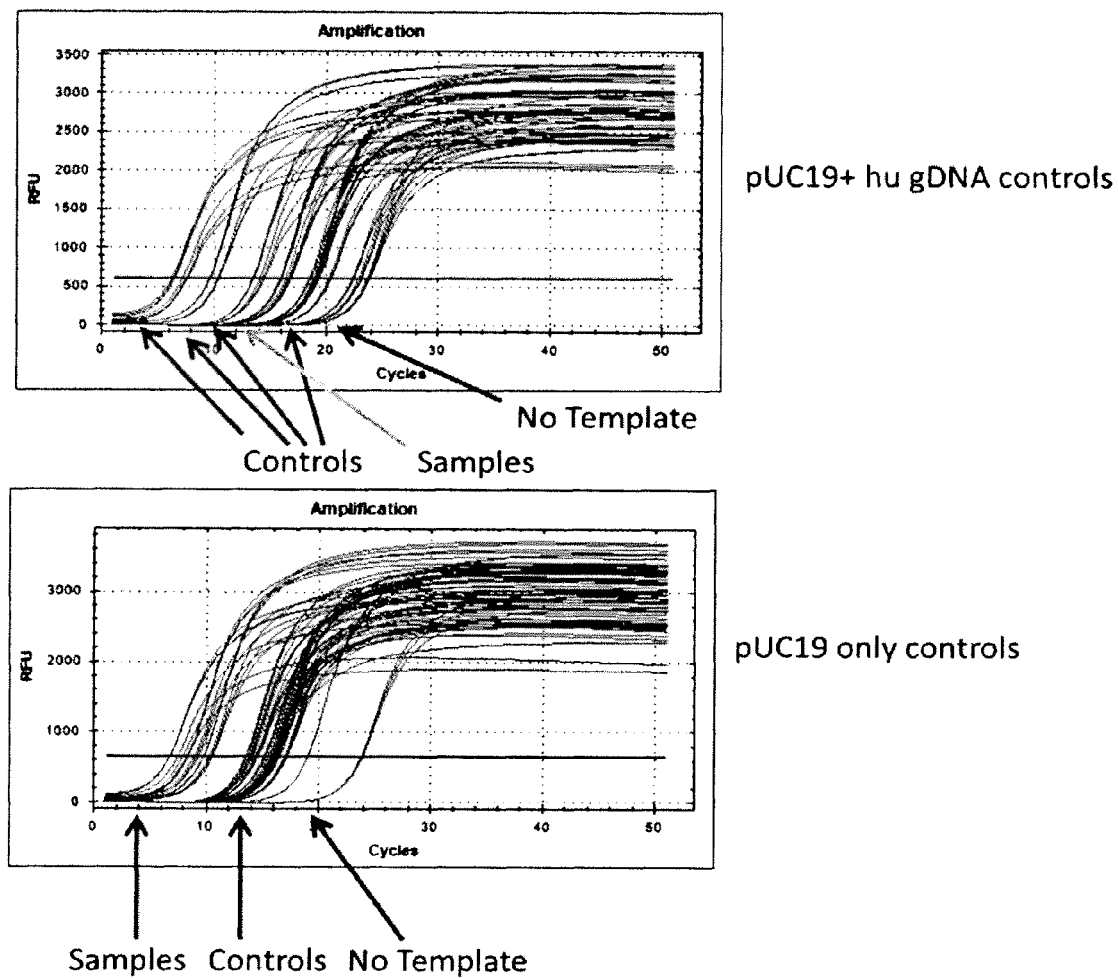
FIG. 27C displays the results of a qPCR reaction of the UDG-treated, captured target polynucleotide (pUC19, in the presence of human genomic DNA) by measuring SYBR green fluorescence.

The results of this experiment are shown in FIG. 27C. pUC19 is in fact being captured, but at background levels. Further refinement is necessary. Potential improvements to the procedure include adjustment of the target DNA levels (e.g., increase the amount of pUC19 DNA as compared to the human genomic DNA), and increasing the amount of Taq polymerase in the nick-translation reaction to make more Taq available at the nick sites on the pUC19 target DNA as opposed to the human DNA nick sites.

Example 4

Extension of Single-stranded Polynucleotides

In some aspects, a polynucleotide device that catalyzes addition of one or more polynucleotide sequences to the 3' end of single-stranded polynucleotide molecule in the presence of a polymerase is utilized. Without being bound by a specific mechanism, the device functions by first hybridizing to a target sequence at a single stranded region of the device. This single stranded region, the primer sequence P, is adjacent a double stranded region formed by hybridization between product sequence Y, positioned 5' to primer sequence P, and sequence Y' which is all or in part complementary to product sequence Y. In the presence of a polymerase and under appropriate conditions, the target sequence is extended to add a sequence complementary to sequence Y, with product sequence Y serving as a template for polymerase activity. As the target sequence is extended, it displaces sequence Y' in the duplex region of the device. Extension of the target sequence continues until a replication blocking group R is reached. When extension of the target sequence is complete, strand migration of sequence Y' displaces the extended target sequence (now in duplex form with product sequence Y) and the double stranded duplex between sequence Y and sequence Y' is restored. The extended target sequence is then dissociated from the device. This process is in one aspect repeated with the same or a different device as long as the product of the extension process terminates with a sequence that can hybridize to the primer sequence P of the same device or a different device.

In one aspect, the devise is synthesized using standard oligonucleotide synthesis techniques. The device is useful in various aspects to add specific polynucleotide sequences to a single stranded molecule such as, for example and without limitation, ABCDEF wherein each of A, B, C, D, E and F are unique polynucleotide sequences. Alternatively, the device provided is useful in other aspects to create repetitive sequences such as XXXXXX wherein X is a specific polynucleotide sequence at the terminus of a target molecule. In still another aspect, the device is used to add polynucleotide sequences combinations such as (ABCDEF)$_n$ to a target molecule. In yet another aspect, the device and methods of its use provided extend evenly all polynucleotide termini in population of target molecules.

In some embodiments, single-stranded polynucleotides are extended using a device with the following properties. The device is for extension of a single-stranded target molecule and is a polynucleotide comprising Structure I:

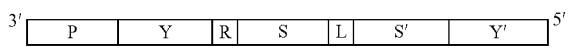

Structure I wherein:
P is a primer sequence;
Y is product sequence;
R is replication blocking group;
S is a stem sequence;
L is a loop region;
S' is a sequence which hybridizes to S;
Y' is a sequence which hybridizes to Y; and
wherein Y, R, S, L, S', and Y' form a hairpin structure.

In other aspects, the device for extension of a single stranded target molecule, the device comprises a first polynucleotide of Structure 2:

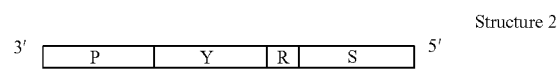

Structure 2 and a second poly nucleotide of Structure 3:

Structure 3 wherein:
P is a primer sequence;
Y is product sequence;
R is replication blocking group;
S is a stem sequence;
Y' is a sequence which hybridizes to Y;
S' is a sequence which hybridizes to S;

In one aspect of the device, sequence S and sequence S' form a duplex structure which is stable at a temperature between about 60° C. and about 75° C.

In another aspect of the device, sequence P is about 6 to bases about 30 bases in length.

In another aspect of the device, sequence Y consists of a sequence P$_Y$ which is identical to priming sequence P. In an alternative aspect of the device, sequence Y comprises a sequence P$_Y$ which is identical to priming sequence P.

In yet another aspect of the device, sequence Y further comprises a tag sequence T which is different from the sequence P$_Y$ and sequence T is located 3' to sequence P$_Y$ and 5' to primer sequence P.

In another aspect of the device, sequence T is about 15 bases to about 50 bases in length.

In still another aspect of the device, sequence Y consists of an added sequence A which is not identical to priming sequence P. In some embodiments, sequence A is about 15 bases to about 50 bases in length.

In another aspect, the device comprises a 3' blocking group F which blocks extension of a sequence of the device, wherein blocking group F is located 3' to sequence P in the device. In various embodiments, blocking group F is an amino group, a phosphate, or a dideoxynucleotide.

In another aspect, the device comprises a sequence X located 5' to sequence Y' and sequence X comprises a nucleotide sequence of about 1 base to about 25 bases in length, wherein sequence X (i) does not hybridize to sequence P, (ii) hybridizes to at least a portion of sequence P, or (iii) hybridizes to at least a portion of sequence P and to at least a portion of sequence Y.

In another aspect of the device, R is an abasic site, a modified base, a base which is absent from product sequence Y is present in a reaction mixture at a limiting concentration. In some embodiments, the modified base comprises a chemical moiety which sterically hinders a polymerase activity to or beyond R. In another embodiment, the modified base is a base which is cross-linked to another base of the oligonucleotide. In still another embodiment, the modified base is cross-linked to a base of S'. In yet another embodiment, the abasic site does not specifically bind to a base of sequence S' or sequence Y'

In another aspect of the device sequence S comprises a GC content between about 70% and about 100%.

In some aspects, a method of extending a single stranded target molecule is utilized, the method comprising contacting the single stranded target molecule with an extension reaction mixture comprising (i) a device as provided herein and/or a composition as provided herein, (ii) a polymerase, and (iii) free nucleotides, whereupon an extension reaction product is generated, wherein an extension product of the reaction comprises the single stranded target molecule with a 3' sequence complementary to product sequence Y of the device.

In one aspect of the method, the extension reaction mixture comprises a device wherein product sequence Y consists of a sequence A of about 20 bases to about 30 bases in length, and the extension product includes a 3' terminal sequence complementary to sequence A.

In another aspect of the method, the extension reaction mixture comprises a device wherein product sequence Y of the oligonucleotide consists of a sequence $P_Y$ which is identical to primer sequence P of the device, whereupon the target molecule sequence is complementary to the primer sequence P and the reaction product has a 3' terminal sequence that is complementary to the primer sequence P.

In another aspect of the methods, the extension reaction mixture comprises a device wherein product sequence Y of the device comprises sequence $P_Y$ which is identical to primer sequence P of the device and further comprises a tag sequence T which is different from the sequence of sequence $P_Y$ and sequence T is located 3' to $P_Y$.

In another aspect of the method, the extension reaction mixture comprises a plurality of devices of as described herein, wherein the plurality comprises at least three subsets of devices, wherein each device of a subset comprises a sequence Y sequence which is (i) the same as sequence Y of another device of the same subset and (ii) different from sequence Y of a device of another subset of the plurality, wherein the extension product has a 3' terminus which comprises a sequence which is complementary to each of sequence Y of the plurality.

II. Structural Features

A. Primer Sequence P

As discussed above, the primer sequence P is the sequence in the device through which the 3' end of the target molecule hybridizes to the device. In one aspect, the 3' end of the target molecule and primer sequence P are 100% complementary. In another aspect, the 3' end of the target molecule and primer sequence P are less than 100% complementary but still sufficiently complementary so that the two sequence will stably hybridize under appropriate conditions to all polymerase extension of the target molecule.

In various aspects, priming sequence P is from X bases to Y bases in length, wherein X is 1, 2, 3, 4, 5, 6, 7, 8, 9, 10, 11, 12, 13, 14, or 15 and Y is about 20, about 25, about 30, about 35 about 40, about 45, about 50, about 55, about 60, about 65, about 70, about 75, about 80, about 85 about 90, about 95 or about 100. In one aspect, priming sequence P in the device is about 5 bases to about 15 bases in length or alternatively, priming sequence P in the device is about 5 bases to about 30, about 5 bases to about 45 bases or about 5 bases to about 60 bases in length. In various other embodiments, priming sequence P is 5 bases, 6 bases, 7 bases, 8 bases, 9 bases, 10 bases, 11 bases, 12 bases, 13 bases, 14 bases, 15 bases, 16 bases, 17 bases, 18 bases, 19 bases, 20 bases, 21 bases, 22 bases, 23 bases, 24 bases, 25 bases, 26 bases, 27 bases, 28 bases, 29 bases, 30 bases, 31 bases, 32 bases, 33 bases, 34 bases, 35 bases, 36 bases, 37 bases, 38 bases, 39 bases, 40 bases, 41 bases, 42 bases, 43 bases, 44 bases, 45 bases, 46 bases, 47 bases, 48 bases, 49 bases, 50 bases, 51 bases, 52 bases, 53 bases, 54 bases, 55 bases, 56 bases, 57 bases, 58 bases, 59 bases, 60 bases, 61 bases, 62 bases, 63 bases, 64 bases, 65 bases, 66 bases, 67 bases, 68 bases, 69 bases, 70 bases, 71 bases, 72 bases, 73 bases, 74 bases, 75 bases, 76 bases, 77 bases, 78 bases, 79 bases, 80 bases, 81 bases, 82 bases, 83 bases, 84 bases, 85 bases, 86 bases, 87 bases, 88 bases, 89 bases, 90 bases, 91 bases, 92 bases, 93 bases, 94 bases, 95 bases, 96 bases, 97 bases, 98 bases, 99 bases, 100 bases or more bases in length.

B. Product Sequence Y

Product sequence Y is a polymerase template in the device; the complement of product sequence Y is the sequence that is added to the extended target molecule.

Product sequence Y, in certain aspects, is from X bases to Y bases in length, wherein X is 1, 2, 3, 4, 5, 6, 7, 8, 9, 10, 11, 12, 13, 14, 15, 16, 17, 18, 19, 20, 21, 22, 23, 24, or 25 and Y is about 30, about 35 about 40, about 45, about 50, about 55, about 60, about 65, about 70, about 75, about 80, about 85 about 90, about 95 or about 100. In other aspects, product sequence Y is about 10 bases to about 75 bases in length. Alternatively, sequence Y is about 10 bases to about 70 bases, about 10 bases to about 65 bases, about 10 bases to about 60 bases, about 10 bases to 55 bases, about 10 bases to about 50 bases in length, about 10 bases to about 45 bases in length, about 10 bases to about 40 bases in length, about 10 bases to about 35 bases in length, about 10 bases to about 30 bases in length, about 10 bases to about 25 bases in length, about 10 bases to about 20 bases in length or about 10 bases to about 15 bases in length. In various other embodiments, the product sequence Y is 5 bases, 6 bases, 7 bases, 8 bases, 9 bases, 10 bases, 11 bases, 12 bases, 13 bases, 14 bases, 15 bases, 16 bases, 17 bases, 18 bases, 19 bases, 20 bases, 21 bases, 22 bases, 23 bases, 24 bases, 25 bases, 26 bases, 27 bases, 28 bases, 29 bases, 30 bases, 31 bases, 32 bases, 33 bases, 34 bases, 35 bases, 36 bases, 37 bases, 38 bases, 39 bases, 40 bases, 41 bases, 42 bases, 43 bases, 44 bases, 45 bases, 46 bases, 47 bases, 48 bases, 49 bases, 50 bases, 51 bases, 52 bases, 53 bases, 54 bases, 55 bases, 56 bases, 57 bases, 58 bases, 59 bases, 60 bases, 61 bases, 62 bases, 63 bases, 64 bases, 65 bases, 66 bases, 67 bases, 68 bases, 69 bases, 70 bases, 71 bases, 72 bases, 73 bases, 74 bases, 75 bases, 76 bases, 77 bases, 78 bases, 79 bases, 80 bases, 81 bases, 82 bases, 83 bases, 84 bases, 85 bases, 86 bases, 87 bases, 88 bases, 89 bases, 90 bases, 91 bases, 92 bases, 93 bases, 94 bases, 95 bases, 96 bases, 97 bases, 98 bases, 99 bases, 100 bases or more bases in length.

1. Sequence $P_Y$

In certain aspects, the product sequence Y consists of a sequence $P_Y$ which is identical to priming sequence P. Alternatively, product sequence Y comprises a sequence $P_Y$ which is identical to priming sequence P. In embodiments wherein the product sequence Y is $P_Y$, extension of the target molecule results in the complement of the primer sequence P being added to the target molecule. Because the resulting extension product terminates at its 3' end with a sequence that is complementary to the priming sequence P (cP), the target molecule can be extended multiple times in the same reaction mixture, each extension reaction adding a sequence to the target that is complementary to the primer sequence P (cP).

In various aspects, sequence $P_Y$ is from X bases to Y bases in length, wherein X is 1, 2, 3, 4, 5, 6, 7, 8, 9, 10, 11, 12, 13, 14, or 15 and Y is about 20, about 25, about 30, about 35 about 40, about 45, about 50, about 55, about 60, about 65, about 70, about 75, about 80, about 85 about 90, about 95 or about 100. In one aspect, sequence $P_Y$ in the device is about 5 bases to about 15 bases in length or alternatively, sequence $P_Y$ in the device is about 5 bases to about 30, about 5 bases to about 45 bases or about 5 bases to about 60 bases in length. In various other embodiments, sequence $P_Y$ is 5 bases, 6 bases, 7 bases, 8 bases, 9 bases, 10 bases, 11 bases, 12 bases, 13 bases, 14 bases, 15 bases, 16 bases, 17 bases, 18 bases, 19 bases, 20 bases, 21 bases, 22 bases, 23 bases, 24 bases, 25 bases, 26 bases, 27 bases, 28 bases, 29 bases, 30 bases, 31 bases, 32 bases, 33 bases, 34 bases, 35 bases, 36 bases, 37 bases, 38 bases, 39 bases, 40 bases, 41 bases, 42 bases, 43 bases, 44 bases, 45 bases, 46 bases, 47 bases, 48 bases, 49 bases, 50 bases, 51 bases, 52 bases, 53 bases, 54 bases, 55 bases, 56 bases, 57 bases, 58 bases, 59 bases, 60 bases, 61 bases, 62 bases, 63 bases, 64 bases, 65 bases, 66 bases, 67 bases, 68 bases, 69 bases, 70 bases, 71 bases, 72 bases, 73 bases, 74 bases, 75 bases, 76 bases, 77 bases, 78 bases, 79 bases, 80 bases, 81 bases, 82 bases, 83 bases, 84 bases, 85 bases, 86 bases, 87 bases, 88 bases, 89 bases, 90 bases, 91 bases, 92 bases, 93 bases, 94 bases, 95 bases, 96 bases, 97 bases, 98 bases, 99 bases, 100 bases or more in length.

2. Tag Sequence T

In certain aspects, product sequence Y comprises a sequence $P_Y$ and tag sequence T which is different from the sequence of $P_Y$. As above, $P_Y$ is identical to primer sequence P. Tag sequence T is located 3' to $P_Y$ and 5' to P (3'-P-T-$P_Y$-5'). In embodiments wherein product sequence Y is 3'-P-T-$P_Y$-5', the target sequence is extended from the complement of primer sequence P (cP), which hybridizes to primer sequence P, to include the complement of tag sequence T (cT), and the complement of sequence $P_Y$ (c$P_Y$) which is the same as the complement of primer sequence P. As in reactions where product sequence Y is $P_Y$, the extension product of this reaction has a 3' sequence 5'-cP-cT-c$P_Y$-3' and since the cPY sequence portion of the extension product is complementary to primer sequence P, the extended target sequence can be further extended multiple times in the same reaction mixture to add multiple copies of 5-'cT-c$P_Y$-3' to the target molecule.

The tag sequence T is, in various embodiments, from X bases to Y bases in length, wherein X is 1, 2, 3, 4, 5, 6, 7, 8, 9, 10, 11, 12, 13, 14, or 15 and Y is about 20, about 25, about 30, about 35 about 40, about 45, about 50, about 55, about 60, about 65, about 70, about 75, about 80, about 85 about 90, about 95 or about 100. In other aspects, tag sequence T is about 10 bases to about 75 bases in length, about 10 bases to about 70 bases, about 10 bases to about 65 bases, about 10 bases to about 60 bases, about 10 bases to 55 bases, or about 10 bases to about 50 bases in length, about 10 bases to about 45 bases in length, about 10 bases to about 40 bases in length, about 10 bases to about 35 bases in length, about 10 bases to about 30 bases in length, about 10 bases to about 25 bases in length, about 10 bases to about 20 bases in length or about 10 bases to about 15 bases in length. In other embodiments, tag sequence T is 5 bases, 6 bases, 7 bases, 8 bases, 9 bases, 10 bases, 11 bases, 12 bases, 13 bases, 14 bases, 15 bases, 16 bases, 17 bases, 18 bases, 19 bases, 20 bases, 21 bases, 22 bases, 23 bases, 24 bases, 25 bases, 26 bases, 27 bases, 28 bases, 29 bases, 30 bases, 31 bases, 32 bases, 33 bases, 34 bases, 35 bases, 36 bases, 37 bases, 38 bases, 39 bases, 40 bases, 41 bases, 42 bases, 43 bases, 44 bases, 45 bases, 46 bases, 47 bases, 48 bases, 49 bases, 50 bases, 51 bases, 52 bases, 53 bases, 54 bases, 55 bases, 56 bases, 57 bases, 58 bases, 59 bases, 60 bases, 61 bases, 62 bases, 63 bases, 64 bases, 65 bases, 66 bases, 67 bases, 68 bases, 69 bases, 70 bases, 71 bases, 72 bases, 73 bases, 74 bases, 75 bases, 76 bases, 77 bases, 78 bases, 79 bases, 80 bases, 81 bases, 82 bases, 83 bases, 84 bases, 85 bases, 86 bases, 87 bases, 88 bases, 89 bases, 90 bases, 91 bases, 92 bases, 93 bases, 94 bases, 95 bases, 96 bases, 97 bases, 98 bases, 99 bases, 100 bases or more bases in length.

3. Sequence A

In another embodiment of the device, product sequence Y comprises an additional sequence A which is not identical to priming sequence P. The extended target molecule has a 3' terminal sequence that is complementary to additional sequence A (5'-cA-3'). In this embodiment, only a single copy of the sequence cA is added to the target molecule in a single reaction mixture in the absence of another device in the same reaction mixture which has a primer sequence P that is identical to additional sequence A.

In certain aspects, the additional sequence A is from X bases to Y bases in length, wherein X is 1, 2, 3, 4, 5, 6, 7, 8, 9, 10, 11, 12, 13, 14, 15, 16, 17, 18, 19, 20, 21, 22, 23, 24, or 25 and Y is about 20, about 25, about 30, about 35 about 40, about 45, about 50, about 55, about 60, about 65, about 70, about 75, about 80, about 85 about 90, about 95 or about 100. In other aspects, additional sequence A is about 20 bases to about 30 bases in length. In other embodiments, the added sequence A is 5 bases, 6 bases, 7 bases, 8 bases, 9 bases, 10 bases, 11 bases, 12 bases, 13 bases, 14 bases, 15 bases, 16 bases, 17 bases, 18 bases, 19 bases, 20 bases, 21 bases, 22 bases, 23 bases, 24 bases, 25 bases, 26 bases, 27 bases, 28 bases, 29 bases, 30 bases, 31 bases, 32 bases, 33 bases, 34 bases, 35 bases, 36 bases, 37 bases, 38 bases, 39 bases, 40 bases, 41 bases, 42 bases, 43 bases, 44 bases, 45 bases, 46 bases, 47 bases, 48 bases, 49 bases, 50 bases, 51 bases, 52 bases, 53 bases, 54 bases, 55 bases, 56 bases, 57 bases, 58 bases, 59 bases, 60 bases, 61 bases, 62 bases, 63 bases, 64 bases, 65 bases, 66 bases, 67 bases, 68 bases, 69 bases, 70 bases, 71 bases, 72 bases, 73 bases, 74 bases, 75 bases, 76 bases, 77 bases, 78 bases, 79 bases, 80 bases, 81 bases, 82 bases, 83 bases, 84 bases, 85 bases, 86 bases, 87 bases, 88 bases, 89 bases, 90 bases, 91 bases, 92 bases, 93 bases, 94 bases, 95 bases, 96 bases, 97 bases, 98 bases, 99 bases, 100 bases or more bases in length.

C. Internal Blocking Group R

The device further includes an internal replication blocking group R which, in various embodiments and without limitation, is an abasic site, a modified base, or a base (or bases) that is (are) absent from product sequence Y, and the corresponding complementary deoxynucleotide triphosphate R' is present in a reaction mixture at a limiting concentration or is absent from the reaction mixture. The worker of ordinary skill in the art will appreciate that any replication blocking group is contemplated for use as an R group as long as the blocking group is capable of being incorporated into the structure of the device. In aspects wherein the blocking group R is a modified base, the modified base comprises, in one aspect, a chemical moiety which sterically hinders binding of a polymerase to blocking group R. Alternatively, the modified base is a base which is cross-linked to another base of the oligonucleotide, and in certain aspects, the modified base is cross-linked to a base of S'. In aspects, wherein blocking group R is an abasic site, this abasic site does not specifically bind to a base of S' or Y'.

D. Stem Sequence S

The device further comprises a stem sequence S which is part of a double stranded portion of the device. Stem sequence S is complementary to all or part of sequence S' in the duplex portion of the device.

In various aspects, stem sequence S is from X bases to Y bases in length, wherein X is 1, 2, 3, 4, 5, 6, 7, 8, 9, 10, 11, 12, 13, 14, 15, 16, 17, 18, 19, 20, 21, 22, 23, 24, or 25 and Y is about 20, about 25, about 30, about 35 about 40, about 45, about 50, about 55, about 60, about 65, about 70, about 75, about 80, about 85 about 90, about 95 or about 100. In other aspects, stem sequence S is from about 5 bases to about 25 bases in length, about 5 bases to about 20 bases in length, or about 5 bass to about 15 bases in length. In other aspects, stem sequence S is 5 bases, 6 bases, 7 bases, 8 bases, 9 bases, 10 bases, 11 bases, 12 bases, 13 bases, 14 bases, 15 bases, 16 bases, 17 bases, 18 bases, 19 bases, 20 bases, 21 bases, 22 bases, 23 bases, 24 bases, 25 bases, 26 bases, 27 bases, 28 bases, 29 bases, 30 bases, 31 bases, 32 bases, 33 bases, 34 bases, 35 bases, 36 bases, 37 bases, 38 bases, 39 bases, 40 bases, 41 bases, 42 bases, 43 bases, 44 bases, 45 bases, 46 bases, 47 bases, 48 bases, 49 bases, 50 bases, 51 bases, 52 bases, 53 bases, 54 bases, 55 bases, 56 bases, 57 bases, 58 bases, 59 bases, 60 bases, 61 bases, 62 bases, 63 bases, 64 bases, 65 bases, 66 bases, 67 bases, 68 bases, 69 bases, 70 bases, 71 bases, 72 bases, 73 bases, 74 bases, 75 bases, 76 bases, 77 bases, 78 bases, 79 bases, 80 bases, 81 bases, 82 bases, 83 bases, 84 bases, 85 bases, 86 bases, 87 bases, 88 bases, 89 bases, 90 bases, 91 bases, 92 bases, 93 bases, 94 bases, 95 bases, 96 bases, 97 bases, 98 bases, 99 bases, 100 bases or more bases in length.

E. Loop Sequence L

In aspects of the invention wherein the device is a single nucleic acid molecule, loop sequence L is present. Loop sequence L is of sufficient length to allow the single nucleic acid device to fold over on itself and give rise to a hairpin secondary structure wherein stem sequence S is able to hybridize to sequence S' and product sequence Y is able to hybridize to sequence Y'.

In various aspects, loop sequence L is about 1 base to about 15 bases in length, about 1 base to about 14 bases in length, about 1 base to about 13 bases in length, about 1 base to about 12 bases in length, about 1 base to about 11 bases in length, about 1 base to about 10 bases in length, about 1 base to about 9 bases in length, about 1 base to about 8 bases in length, about 1 base to about 7 bases in length about 1 base to about 6 bases in length, or about 1 base to about 5 bases in length. Alternatively, loop sequence L is 5 bases, 6 bases, 7 bases, 8 bases, 9 bases, 10 bases, 11 bases, 12 bases, 13 bases, 14 bases, 15 bases, 16 bases, 17 bases, 18 bases, 19 bases, 20 bases, 21 bases, 22 bases, 23 bases, 24 bases, 25 bases, 26 bases, 27 bases, 28 bases, 29 bases, 30 bases, 31 bases, 32 bases, 33 bases, 34 bases, 35 bases, 36 bases, 37 bases, 38 bases, 39 bases, 40 bases, 41 bases, 42 bases, 43 bases, 44 bases, 45 bases, 46 bases, 47 bases, 48 bases, 49 bases, 50 bases, 51 bases, 52 bases, 53 bases, 54 bases, 55 bases, 56 bases, 57 bases, 58 bases, 59 bases, 60 bases, 61 bases, 62 bases, 63 bases, 64 bases, 65 bases, 66 bases, 67 bases, 68 bases, 69 bases, 70 bases, 71 bases, 72 bases, 73 bases, 74 bases, 75 bases, 76 bases, 77 bases, 78 bases, 79 bases, 80 bases, 81 bases, 82 bases, 83 bases, 84 bases, 85 bases, 86 bases, 87 bases, 88 bases, 89 bases, 90 bases, 91 bases, 92 bases, 93 bases, 94 bases, 95 bases, 96 bases, 97 bases, 98 bases, 99 bases, 100 bases or more bases in length.

F. Stem Sequence S'

The device further comprises stem sequence S' which, as discussed above, is all or in part complementary to stem sequence S and is part of a duplex region of the device.

In various aspects, stem sequence S is from X bases to Y bases in length, wherein X is 1, 2, 3, 4, 5, 6, 7, 8, 9, 10, 11, 12, 13, 14, 15, 16, 17, 18, 19, 20, 21, 22, 23, 24, or 25 and Y is about 20, about 25, about 30, about 35 about 40, about 45, about 50, about 55, about 60, about 65, about 70, about 75, about 80, about 85 about 90, about 95 or about 100. In other aspects, sequence S' is from about 5 bases to about 25 bases in length, about 5 bases to about 20 bases in length, or about 5 bass to about 15 bases in length. In other aspects, sequence S' is 5 bases, 6 bases, 7 bases, 8 bases, 9 bases, 10 bases, 11 bases, 12 bases, 13 bases, 14 bases, 15 bases, 16 bases, 17 bases, 18 bases, 19 bases, 20 bases, 21 bases, 22 bases, 23 bases, 24 bases, 25 bases, 26 bases, 27 bases, 28 bases, 29 bases, 30 bases, 31 bases, 32 bases, 33 bases, 34 bases, 35 bases, 36 bases, 37 bases, 38 bases, 39 bases, 40 bases, 41 bases, 42 bases, 43 bases, 44 bases, 45 bases, 46 bases, 47 bases, 48 bases, 49 bases, 50 bases, 51 bases, 52 bases, 53 bases, 54 bases, 55 bases, 56 bases, 57 bases, 58 bases, 59 bases, 60 bases, 61 bases, 62 bases, 63 bases, 64 bases, 65 bases, 66 bases, 67 bases, 68 bases, 69 bases, 70 bases, 71 bases, 72 bases, 73 bases, 74 bases, 75 bases, 76 bases, 77 bases, 78 bases, 79 bases, 80 bases, 81 bases, 82 bases, 83 bases, 84 bases, 85 bases, 86 bases, 87 bases, 88 bases, 89 bases, 90 bases, 91 bases, 92 bases, 93 bases, 94 bases, 95 bases, 96 bases, 97 bases, 98 bases, 99 bases, 100 bases or more bases in length.

G. Sequence Y'

The device also includes sequence Y' which in certain aspects is complementary to product sequence Y. Hybridization of Y' to Y gives rise to a duplex region of the device. In certain aspects, sequence Y' complementary to product sequence Y over its entire length. In other aspects, sequence Y' is complementary to product sequence Y over only a partial length of sequence Y'.

Sequence Y', in certain aspects, is from X bases to Y bases in length, wherein X is 1, 2, 3, 4, 5, 6, 7, 8, 9, 10, 11, 12, 13, 14, 15, 16, 17, 18, 19, 20, 21, 22, 23, 24, or 25 and Y is about 30, about 35 about 40, about 45, about 50, about 55, about 60, about 65, about 70, about 75, about 80, about 85 about 90, about 95 or about 100. In other aspects, product sequence Y is about 10 bases to about 75 bases in length. Alternatively, sequence Y' is about 10 bases to about 70 bases, about 10 bases to about 65 bases, about 10 bases to about 60 bases, about 10 bases to 55 bases, about 10 bases to about 50 bases in length, about 10 bases to about 45 bases in length, about 10 bases to about 40 bases in length, about 10 bases to about 35 bases in length, about 10 bases to about 30 bases in length, about 10 bases to about 25 bases in length, about 10 bases to about 20 bases in length or about 10 bases to about 15 bases in length. In various other embodiments, the sequence Y' is 5 bases, 6 bases, 7 bases, 8 bases, 9 bases, 10 bases, 11 bases, 12 bases, 13 bases, 14 bases, 15 bases, 16 bases, 17 bases, 18 bases, 19 bases, 20 bases, 21 bases, 22 bases, 23 bases, 24 bases, 25 bases, 26 bases, 27 bases, 28 bases, 29 bases, 30 bases, 31 bases, 32 bases, 33 bases, 34 bases, 35 bases, 36 bases, 37 bases, 38 bases, 39 bases, 40 bases, 41 bases, 42 bases, 43 bases, 44 bases, 45 bases, 46 bases, 47 bases, 48 bases, 49 bases, 50 bases, 51 bases, 52 bases, 53 bases, 54 bases, 55 bases, 56 bases, 57 bases, 58 bases, 59 bases, 60 bases, 61 bases, 62 bases, 63 bases, 64 bases, 65 bases, 66 bases, 67 bases, 68 bases, 69 bases, 70 bases, 71 bases, 72 bases, 73 bases, 74 bases, 75 bases, 76 bases, 77 bases, 78 bases, 79 bases, 80 bases, 81 bases, 82 bases, 83 bases, 84 bases, 85 bases, 86 bases, 87 bases, 88 bases, 89 bases, 90 bases, 91 bases, 92 bases, 93 bases, 94 bases, 95 bases, 96 bases, 97 bases, 98 bases, 99 bases, 100 bases or more bases in length.

H. Sequence X

In another embodiment, the device optionally comprises a sequence X which hybridizes to a portion of priming sequence P. When in the device, sequence X is positioned 5' to sequence Y'. Without being bound by a specific mechanism, it is postulated that the presence of sequence X increases specificity with which the target sequence hybridizes to the primer sequence P. Alternatively, or in addition, the presence of the sequence X increases the rate and/or degree of dissociation of the extended target sequence from the device once extension of the target sequence is completed. In certain aspects, sequence X hybridizes to the 5' end of P. In various embodiments, sequence X does not hybridize to any sequence in the device. In another aspect, sequence X hybridizes to at least a portion of primer sequence P. In still another embodiment, sequence X hybridizes to at least a portion of primer sequence P and to at least a portion of product sequence Y.

In various embodiments, sequence X is from X bases to Y bases in length, wherein X is 1, 2, 3, 4, or 5 and X is 6, 7, 8, 9, 10, 11, 12, 13, 14, 15, 16, 17, 18, 19, 20 or more. In other aspects, sequence X is about 1 base to about 20 bases, about 1 base to about 15 bases, or about 1 base to about 10 bases. In certain aspects, sequence X is 1, base, 2 bases, 3 bases, 4 bases, 5 bases, 6 bases, 7 bases, 8 bases, 9 bases, 10 bases, 11 bases, 12 bases, 13 bases, 14 bases, 15 bases, 16 bases, 17 bases, 18 bases, 19 bases, 20 bases, 21 bases, 22 bases, 23 bases, 24 bases, 25 bases, or more bases in length.

I. Blocking Group F

The device of the invention optionally includes a blocking group F positioned 3' to the primer sequence P. Blocking group F blocks polymerase activity on primer sequence P, i.e., precludes increasing length of the primer sequence P. When present, the blocking group F in certain aspects is a 3" amino group, a 3' phosphate, or a dideoxynucleotide, a six carbon glycol spacer (and in one aspect the six carbon glycol spacer is hexanediol) and inverted deoxythymidine (dT). The person of ordinary skill in the art will appreciate that any polymerase blocking group can be positioned 3' to priming sequence P. For example, inasmuch as a 3' hydroxyl group is necessary for polymerase activity, the worker of ordinary skill will appreciate that any group other than a 3' hydroxyl at the 3' terminus of primer sequence P will be a useful blocking group.

III. Physical Properties

In certain aspects, the double stranded region between sequence S and sequence S' is maintained without dissociation during an extension reaction. Alternatively, the double stranded region between sequence S and sequence S' is not maintained without dissociation, but at any instance in time, it is more likely than not that sequence S and sequence S' are in a duplex conformation. The worker of ordinary skill in the art will readily appreciate how to design and synthesize sequence S and sequence S' in order to either maintain double stranded conformation or to insure that the double stranded conformation is more likely to exist at any instance in time over the course of an extension reaction.

For example and without limitation, stability of a duplex region formed between sequence S and sequence S' is increased with a high GC content. Thus, in certain aspects, sequence S and sequence S' have a GC content between about 80% and about 100%.

In another example, and with respect to a device of the invention comprising two polynucleotides as set out above, the two polynucleotides are driven toward hybridization in mixtures wherein one polynucleotide is present in a molar excess of the other polynucleotide. In various aspects, the polynucleotide as set out in Structure 3 is present in a 2×, 3,×, 4×, 5×, 6×, 7×, 8×, 9×, 10, 20×, 30×, 40×, 50×, 60×, 70×, 80×, 90×, 100×, 200×, 300×, 400×, 500×, 600×, 700×, 800×, 900×, 1000× or greater molar excess compared to the concentration of the polynucleotide set out ion Structure 2 above.

The worker of ordinary skill in the art will appreciate that, in certain aspects, reaction conditions in an extension reaction are modified so as to enhance the likelihood that double strands regions in a device of the invention are stabilized. Reaction condition parameters that are subject to modification include, for example, salt concentration and pH. In view of the requirement that an extension product eventually will be displaced, or dehybridized, from a device in the reaction mixture and double stranded regions of the device are reformed prior to any further extension reaction, a balance is achieved with respect to temperature of the reaction mixture and stability of either a double stranded region formed between primer sequence P with a target molecule, primer sequence P and product sequence Y with an extension product, product sequence Y with sequence Y', stem sequence S with sequence S', product sequence Y and stem sequence S with sequence Y' and sequence S'.

IV. Polynucleotides of the Devices

As used herein, the term "polynucleotide" as a target molecule, is used interchangeably with the term oligonucleotide. The term "nucleotide" or its plural as used herein is interchangeable with modified forms as discussed herein and otherwise known in the art. In certain instances, the art uses the term "nucleobase" which embraces naturally-occurring nucleotides as well as modifications of nucleotides that can be polymerized.

Methods of making polynucleotides for a device having a predetermined sequence are well-known in the art. See, e.g., Sambrook et al., Molecular Cloning: A Laboratory Manual (2nd ed. 1989) and F. Eckstein (ed.) Oligonucleotides and Analogues, 1st Ed. (Oxford University Press, New York, 1991). Solid-phase synthesis methods are preferred for both oligoribonucleotides and oligodeoxyribonucleotides (the well-known methods of synthesizing DNA are also useful for synthesizing RNA). Oligoribonucleotides and oligodeoxyribonucleotides can also be prepared enzymatically.

In various aspects, methods provided include use of polynucleotides which are DNA, modified DNA, RNA, modified RNA or combinations of the two types. Modified forms of polynucleotides are also contemplated for devices of the invention which include those having at least one modified internucleotide linkage.

VI. Target Molecules

In various aspects, a target molecule for use with a device of the invention is a single stranded polynucleotide. In another aspect, the target molecule is a double stranded molecule that has an overhanging 3' sequence. In either embodiment, the 3' single strand terminus of the target molecule is sufficiently complementary to a primer sequence P of a device to allow for hybridization to the primer sequence P. In various aspects, the 3' single strand terminus of the target molecule is 100% complementary to primer sequence P of the device, or alternatively, the 3' single strand terminus of the target molecule is less than 100% complementary to primer sequence P of the device.

In various aspects, the target molecule is bound to a support in a way that the 3' terminus of the target molecule is free to hybridize to the primer sequence P of a device.

VII. Compositions and Uses

Compositions are provided comprising one or more devices as described herein. In one aspect, compositions of the invention comprise two or more devices wherein all of the devices are the same, i.e., the product sequence Y in all of the devices in the composition are the same and all devices extend the target molecule to have the same added sequence.

In another aspect, compositions are provided wherein at least two devices in the composition are not the same, i.e., product sequence Y in one device is different from product sequence Y in a second device such that at least two devices in the composition extend the target molecule to have difference added sequences.

In one aspect of this type of composition, it is contemplated that the two devices in the composition extend the same target molecule consecutively, wherein the product of the first extension reaction results in a 3' extension sequence which makes this first extension product amenable to further extension with a second device in the composition.

The worker of ordinary skill in the art will readily appreciate that any number of different devices can be provided in a composition such that the extension product of a first extension reaction can be rendered amenable to further extension by a second device, the extension product from a second extension reaction with a second device can be rendered amendable to further extension by a third device, and so forth. Any number of devices is contemplated for compositions of the invention.

---

What is claimed is:

1. A method of isolating a double-stranded target polynucleotide molecule, said double-stranded target polynucleotide molecule having an internal destabilized region, wherein the destabilized region comprises (i) one intact polynucleotide strand in the double-stranded target polynucleotide and (ii) another strand substantially complementary to the intact strand and with a plurality of abasic sites or mismatches, said method comprising the steps of:
   (a) contacting the internal destabilized region with a single-stranded polynucleotide under appropriate conditions, thereby forming a mixture, said single-stranded polynucleotide comprising a linker portion and a capture portion, said linker portion having a sequence sufficiently complementary to the intact polynucleotide strand of the destabilized region of the double-stranded target polynucleotide molecule such that the linker portion hybridizes to the intact polynucleotide strand of the destabilized region of the double-stranded target polynucleotide molecule, and said capture portion has a sequence sufficiently complementary to a nucleotide sequence of a capture substance and does not hybridize to the destabilized region of the double-stranded target polynucleotide molecule, wherein the capture substance comprises a polynucleotide probe having a sequence sufficiently complementary to the capture portion of the single-stranded polynucleotide;
   (b) adding the capture substance into the mixture so that the capture substance hybridizes with the capture portion of the single-stranded polynucleotide; and
   (c) isolating the double-stranded target polynucleotide molecule after step (b).

2. The method of claim 1, wherein the single-stranded polynucleotide is allele-specific.

3. The method of claim 1, wherein the single-stranded polynucleotide is haplotype-specific.

4. The method of claim 1, further comprising the step of extending the capture portion of the single-stranded polynucleotide after step (a).

5. The method of claim 4, wherein the extending step adds a specific sequence to the capture portion of the single-stranded polynucleotide.

6. The method of claim 5, wherein the capture portion of the single-stranded polynucleotide is extended by rolling circle amplification.

7. The method of claim 5, wherein the polynucleotide probe hybridizes to the specific sequence.

8. The method of claims 4, wherein the extending step adds a sequence to the capture portion.

9. The method of claim 1, further comprising a step of cleaving a phosphodiester bond of the double-stranded target polynucleotide molecule after step c).

10. The method of claim 9, wherein the phosphodiester bond is cleaved by a nicking endonuclease.

11. The method of claim 10 wherein the nicking endonuclease is selected from the group consisting of Nb.BbvCI, Nb.BsmI, Nb.BsrDI, Nb.BtsI, Nt.AlwI, Nt.BbvCI, Nt.BsmAI, Nt.BspQI, Nt.BstNBI and Nt.CviPII.

12. The method of claim 1, further comprising a step of generating the single-stranded region in the double-stranded target polynucleotide molecule by cleaving a phosphodiester bond of the double-stranded target polynucleotide molecule and removing one or more bases in a single strand of the double-stranded target polynucleotide molecule adjacent the phosphodiester bond after step c).

13. The method of claim 1, further comprising a step of generating the double-stranded target polynucleotide molecule before step a) by cleaving a phosphodiester bond in a double-stranded polynucleotide molecule with a nicking endonuclease, producing a nicked double-stranded target polynucleotide molecule, incubating the nicked double-stranded polynucleotide molecule with dGTP, dATP, dCTP, and dUTP nucleotides and a DNA polymerase with 5' to 3' exonuclease activity thereby synthesizing a new double-stranded polynucleotide molecule, and treating the synthesized double-stranded polynucleotide molecule with Uracil-DNA glycosylase (UDG).

14. The method of claim 1, wherein the double-stranded target polynucleotide molecule is released from the capture substance during step (c).

15. The method of claim 14 wherein the target double-stranded polynucleotide molecule is released by enzymatic degradation of the capture portion and capture substance.

16. The method of claim 1, wherein the polynucleotide probe is covalently attached to a bead.

17. The method of claim 1, wherein the polynucleotide probe is covalently attached to a first binding partner and a second binding partner.

* * * * *